(12) United States Patent
Fujii et al.

(10) Patent No.: US 7,423,007 B2
(45) Date of Patent: Sep. 9, 2008

(54) CXCR4 ANTAGONIST AND USE THEREOF

(75) Inventors: Nobutaka Fujii, Shiga (JP); Hirokazu Tamamura, Kyoto (JP); Akira Hori, Hyogo (JP)

(73) Assignee: Biokine Therapeutics Ltd., Rehovot (IL)

( * ) Notice: Subject to any disclaimer, the term of this patent is extended or adjusted under 35 U.S.C. 154(b) by 0 days.

(21) Appl. No.: 10/525,838

(22) PCT Filed: Aug. 26, 2003

(86) PCT No.: PCT/JP03/10753

§ 371 (c)(1),
(2), (4) Date: Oct. 14, 2005

(87) PCT Pub. No.: WO2004/020462

PCT Pub. Date: Mar. 11, 2004

(65) Prior Publication Data

US 2006/0264378 A1 Nov. 23, 2006

(30) Foreign Application Priority Data

Aug. 27, 2002 (JP) ............................. 2002-247843

(51) Int. Cl.
*A61K 38/00* (2006.01)
*A61K 38/04* (2006.01)
*A61K 38/10* (2006.01)
*C07K 5/00* (2006.01)
*C07K 7/08* (2006.01)

(52) U.S. Cl. .......................... 512/14; 512/2; 530/326; 530/327; 530/333

(58) Field of Classification Search ....................... None
See application file for complete search history.

(56) References Cited

U.S. PATENT DOCUMENTS 7,138,488 B2 * 11/2006 Fujii ........................... 530/326

FOREIGN PATENT DOCUMENTS

| WO | WO 95/10534 | 4/1995 |
|---|---|---|
| WO | WO 99/47158 | 9/1999 |
| WO | WO 01/38352 | 5/2001 |
| WO | WO 01/85196 | 11/2001 |
| WO | WO 02/20561 A1 * | 2/2002 |

OTHER PUBLICATIONS

Tamamura H, Arakaki R, Funakoshi H, Imai M, Otaka A, Ibuka T, Nakashima H, Murakami T, Waki M, Matsumoto A,, Yamamoto N and Fujii N, Effective lowly cytotoxic analgos of an HIV-cell fusion inhibitor, T22([Tyr 5, 12, Lys7]-polyphemusin II), Bioorg Med Chem, 1998, 6: 231-238.*
Tamamura H, Xu Y, Hattori T, Zhang X, Arakaki R, Kanbara K, Omagari A, Otaka A, Ibuka T, Yamamoto N, Nakashima H and Fujii N, A Low-Molecular-Weight Inhibitor against the Chemokine Receptor CXCR4: A Strong Anti-HIV Peptide T140, BBRC, 1998, 253: 877-882.*
Introduction to Cancer from the Merck manual.*
Clinical Aspects of Cancer from the Merck manual.*
Auerbach R, Akhtar N, Lewis RL, Shinners BL, Angiogenesis assays: Problems and pitfalls, Cancer and Metastasis Reviews, 2000, 19: 167-172.*
Gura T, Cancer Models: Systems for Identifying New Drugs Are Often Faulty, Science, 1997, 278(5340): 1041-1042, enclosed pp. 1-5.*
Jain RK, Barriers to Drug Delivery in Solid Tumors, Scientific American, Jul. 1994, 58-65.*
Rheumatoid Arthritis from the Merck Manual.*
Tamamura H, Xu Younong, Hattori T, Zhang X, Arakaki R, Kanbara K, Omagari A, Otaka A, Ibuka T, Yamamoto N, Nakashima H, Fujii N, A Low-Molecular-Weight Inhibitor against chemokine receptor CXCR4: A strong Anti-HIV Peptide T140, Biochemical and Biophysical Research Communications, 1998, 253: 877-882.*
Hatse et al., CXC-chemokine receptor 4 as a potential new therapeutic target for neuroblastoma and breast cancer, *International Journal of Canc. Suppl*, 2002;13:349.
Hiramatsu et al., Synthesis of CXCR4 antagonists, T140 derivatives with improved biostability,and their SAR study. *Peptide Science* 203;2002: 213-216 (Yamada, T, ed.).
Mori et al., Involvement of Stromal cell-Derived Factor 1 and CXCR4 receptor system in pancreatic cancer. *Gastroenterology,* 2002;122(4), Suppl 1:A490. (Abstract T1608).
Tamamura et al., Downsizing of an HIV-cell fusion inhibitor, T22 ([Tyr5,12,Lys7]-polyphemusin II), with the maintenance of anti-HIV activity and solution structure. *Bioorg Med Chem.* 1998, 6:473-9.
Tamamura et al., T140 analogs as CXCR4 antagonists identified as anti-metastatic agents in the treatment of breast cancer. *FEBS Lett.* (Aug. 28, 2003) 550:79-83.

* cited by examiner

*Primary Examiner*—Anish Gupta
*Assistant Examiner*—Julie Ha
(74) *Attorney, Agent, or Firm*—Browdy and Neimark

(57) ABSTRACT

The present invention provides preventive and/or therapeutic drugs for cancer and chronic rheumatoid arthritis which contain a peptide having a CXCR4 antagonism, its amide, its ester or its salt. Also, the present invention provides a novel peptide having a CXCR4 antagonism, its amide, its ester and its salt.

23 Claims, 7 Drawing Sheets

CXCR4 ANTAGONIST AND USE THEREOF

TECHNICAL FIELD

The present invention relates to compounds having CXCR4 antagonistic action, and to preventive and/or therapeutic medicines containing such compounds for cancers and chronic rheumatoid arthritis.

BACKGROUND ART

Many hormones and neurotransmitters regulate vital functions through specific receptors existing in cell membranes.

Many of these receptors conduct intracellular signaling through the activation of coupled guanine nucleotide-binding protein (as may be hereafter abbreviated to "G-protein"). Also, these receptors are collectively called G-protein-coupled receptors (GPCR) or 7 trans-membrane receptors (7TMR), as they have common structures having seven trans-cytomembrane domains.

As one of such G-protein-coupled receptors, a human receptor protein coded by CXCR4 gene is known [Journal of biological chemistry, Vol. 273, 4754 (1998)].

Also, CXCL12/SDF-1α, which is a physiologically active peptide functioning as a ligand of the above-mentioned CXCR4, is known [Science, Vol. 261, 600-603 (1993)].

Certain peptidic compounds having antagonistic action against CXCR4 are disclosed and their anti-HIV activity is described in Fujii, International Publication WO02/20561 Mar. 14, 2003.

Cancer metastasis is one of the critical factors affecting the life expectancy of patients. It is reported that the expression of CXCR4 is enhanced in breast cancer cells, etc., and that the expression of CXCL12/SDF-1α which is a ligand of CXCR4 is enhanced in cancer-metastasized organs (lymph nodes, lungs, livers and bones) [Nature, Vol. 410, 50-56 (2001)]. Also, in chronic rheumatoid arthritis, the infiltration of CD4 positive memrory T-cells into articular cavity fluids affects the progression of the conditions. It is reported that in CD4 positive T-cells in articular cavity fluids of patients suffering from chronic rheumatoid arthritis, the expression of CXCR4 genes is enhanced, and that the expression of CXCL12/SDF-1α genes is enhanced in articular synovial membrane tissues [Journal of Immunology, Vol. 165, 6590-98 (2000)].

The present invention aims at providing novel means using CXCR4 antagonistic compounds for the prevention and/or therapy of cancers and chronic rheumatoid arthritis. Also, the present invention provides novel compounds, in particular, various oligopeptides with common structures, which have preventive and/or therapeutic activity for cancers and chronic rheumatoid arthritis.

DISCLOSURE OF THE INVENTION

The inventors of the present invention were dedicated to studying possibilities of solving the above-mentioned problem, and as a result, have discovered that CXCR4 antagonistic compounds previously considered effective as chemotherapeutics for AIDS are effective for the prevention and/or therapy of cancers, including metastatic cancers, and chronic rheumatoid arthritis, and have completed the present invention through further research efforts.

That is, the present invention relates to the followings:

(1) Preventive and/or therapeutic medicines for cancers and chronic rheumatoid arthritis, containing a peptide indicated by the following formula (Ia) or a salt thereof:

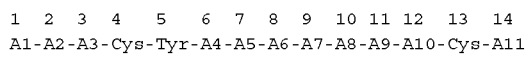

In this formula:

A1 is an arginine, lysine, ornithine, citrulline, alanine or glutamic acid residue which may be derivatized at N-terminal, or A1 is deleted;

A2 represents an arginine or glutamic acid residue if A1 is an arginine, lysine, ornithine, citrulline, alanine or glutamic acid residue which may be derivatized at N-terminal, or A2 represents an arginine or glutamic acid residue which may be derivatized at N-terminal if A1 is deleted;

A3 represents an aromatic amino acid residue;

A4, A5 and A9 each independently represents an arginine, lysine, ornithine, citrulline, alanine or glutamic acid residue;

A6 represents a proline, glycine, ornithine, lysine, alanine, citrulline, arginine or glutamic acid residue;

A7 represents a proline, glycine, ornithine, lysine, alanine, citrulline or arginine residue;

A8 represents a tyrosine, phenylalanine, alanine, naphthylalanine, citrulline or glutamic acid residue;

A10 represents a citrulline, glutamic acid, arginine or lysine residue;

A11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(2) Preventive and/or therapeutic medicines stated in (1).

In the above formula (Ia):

A1 is an arginine, citrulline, alanine or glutamic acid residue which may be derivatized at N-terminal, or A1 is deleted;

A2 represents an arginine or glutamic acid residue if A1 is an arginine, citrulline, alanine or glutamic acid residue which may be derivatized at N-terminal, or A2 represents an arginine or glutamic acid residue which may be derivatized at N-terminal if A1 is deleted;

A4 represents an arginine, citrulline, alanine or glutamic acid residue;

A5 represents an arginine, citrulline, alanine, lysine or glutamic acid residue;

A6 represents a lysine, alanine, citrulline or glutamic acid residue;

A7 represents a proline or alanine residue;

A8 represents a tyrosine, alanine or glutamic acid residue;

A9 represents an arginine, citrulline or glutamic acid residue;

A10 represents a citrulline or glutamic acid residue;

A11 represents an arginine or glutamic acid residue which may be derivatized at C-terminal.

(3) Peptide represented by the following formula (Ib) or a salt thereof:

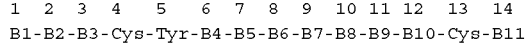

In this formula:

B1 is a glutamic acid residue which may be derivatized at N-terminal, or B1 is deleted;

B2 represents an arginine or glutamic acid residue if B1 is a glutamic acid residue which may be derivatized at N-terminal, or B2 represents an arginine or glutamic acid residue which may be derivatized at N-terminal if B1 is deleted;

B3 represents an aromatic amino acid residue;

B4, B5 and B9 each independently represents an arginine, lysine, ornithine, citrulline, alanine or glutamic acid residue;

B6 represents a proline, glycine, ornithine, lysine, alanine, citrulline, arginine or glutamic acid residue;

B7 represents a proline, glycine, ornithine, lysine, alanine, citrulline or arginine residue;

B8 represents a tyrosine, phenylalanine, alanine, naphthylalanine, citrulline or glutamic acid residue;

B10 represents a citrulline, glutamic acid, arginine or lysine residue;

B11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(4) Peptide or its salt stated in (3).

Bib 1 is a glutamic acid residue which may be derivatized at N-terminal.

(5) Peptide indicated by the following formula (Ic) or a salt thereof:

(Ic)

1  2  3  4   5  6  7  8  9  10 11 12  13  14
C1-C2-C3-Cys-Tyr-C4-C5-C6-C7-C8-C9-C10-Cys-C11

In this formula:

C1 is an ariginine, lysine, ornithin, citrulline, alanine or glutamic acid residue which may be derivatized at N-terminal, or C1 is deleted;

C2 represents a glutamic acid residue if C1 is an ariginine, lysine, ornithine, citrulline, alanine or glutamic acid residue which may be derivatized at N-terminal, or C2 represents a glutamic acid residue which may be derivatized at N-terminal if C1 is deleted;

C3 represents an aromatic amino acid residue;

C4, C5 and C9 each independently represents an arginine, lysine, ornithine, citrulline, alanine or glutamic acid residue;

C6 represents a proline, glycine, ornithine, lysine, alanine, citrulline, arginine or glutamic acid residue;

C7 represents a proline, glycine, ornithine, lysine, alanine, citrulline or arginine residue;

C8 represents a tyrosine, phenylalanine, alanine, naphthylalanine, citrulline or glutamic acid residue;

C10 represents a citrulline, glutamic acid, arginine or lysine residue;

C11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(6) Peptide represented by the following formula (Id) or a salt thereof:

(Id)

1  2  3  4   5  6  7  8  9  10 11 12  13  14
D1-D2-D3-Cys-Tyr-D4-D5-D6-D7-D8-D9-D10-Cys-D11

In this formula:

D1 is an arginine, lysine, ornithine, citrulline, alanine or glutamic acid residue which may be derivatized at N-terminal, or D1 is deleted;

D2 represents an arginine or glutamic acid residue if D1 is an arginine, lysine, ornithine, citrulline, alanine or glutamic acid residue which may be derivatized at N-terminal, or D2 represents an arginine or glutamic acid residue which may be derivatized at N-terminal if D1 is deleted;

D3 represents an aromatic amino acid residue;

D4 represents a glutamic acid residue;

D5 and D9 each independently represents an arginine, lysine, ornithine, citrulline, alanine or glutamic acid residue;

D6 represents a proline, glycine, ornithine, lysine, alanine, citrulline, arginine or glutamic acid residue;

D7 represents a proline, glycine, ornithine, lysine, alanine, citrulline or arginine residue;

D8 represents a tyrosine, phenylalanine, alanine, naphthylalanine, citrulline or glutamic acid residue;

D10 represents a citrulline, glutamic acid, arginine or lysine residue;

D11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(7) Peptide indicated by the following formula (Ie) or a salt thereof:

(Ie)

1  2  3  4   5  6  7   8  9  10 11 12  13  14
E1-E2-E3-Cys-Tyr-E4-E5-E6-E7-E8-E9-E10-Cys-E11

In this formula:

E1 is an arginine, lysine, ornithine, citrulline, alanine or glutamic acid residue which may be derivatized at N-terminal, or E1 is deleted;

E2 represents an arginine or glutamic acid residue if E1 is an arginine, lysine, ornithine, citrulline, alanine or glutamic acid residue which may be derivatized at N-terminal, or E2 represents an arginine or glutamic acid residue which may be derivatized at N-terminal if E1 is deleted;

E3 represents an aromatic amino acid residue;

E4 and E9 each independently represents an arginine, lysine, ornithine, citrulline, alanine or glutamic acid residue;

E5 represents an arginine or glutamic acid residue;

E6 represents a proline, glycine, ornithine, lysine, alanine, citrulline, arginine or glutamic acid residue;

E7 represents a proline, glycine, ornithine, lysine, alanine, citrulline or arginine residue;

E8 represents a tyrosine, phenylalanine, alanine, naphthylalanine, citrulline or glutamic acid residue;

E10 represents a citrulline, glutamic acid, arginine or lysine residue;

E11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(8) Peptide or its salt stated in (7).

E5 represents a glutamic acid residue.

(9) Peptide represented by the following formula (If) or a salt thereof:

```
    1  2  3  4   5  6  7  8  9 10 11 12  13  14
    F1-F2-F3-Cys-Tyr-F4-F5-F6-F7-F8-F9-F10-Cys-F11
```
(If)

In this formula:

F1 is an arginine, lysine, ornithine, citrulline, alanine or glutamic acid residue which may be derivatized at N-terminal, or F1 is deleted;

F2 represents an arginine or glutamic acid residue if F1 is an arginine, lysine, ornithine, citrulline, alanine or glutamic acid residue which may be derivatized at N-terminal, or F2 represents an arginine or glutamic acid residue which may be derivatized at N-terminal if F1 is deleted;

F3 represents an aromatic amino acid residue;

F4, F5 and F9 each independently represents an arginine, lysine, ornithine, citrulline, alanine or glutamic acid residue;

F6 represents a glutamic acid residue;

F7 represents a proline, glycine, ornithine, lysine, alanine, citrulline or arginine residue;

F8 represents a tyrosine, phenylalanine, alanine, naphthylalanine, citrulline or glutamic acid residue;

F10 represents a citrulline, glutamic acid, arginine or lysine residue;

F11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(10) Peptide represented by the following formula (Ig) or a salt thereof:

```
    1  2  3  4   5  6  7  8  9 10 11 12  13  14
    G1-G2-G3-Cys-Tyr-G4-G5-G6-G7-G8-G9-G10-Cys-G11
```
(Ig)

In this formula:

G1 is an arginine, lysine, ornithine, citrulline, alanine or glutamic acid residue which may be derivatized at N-terminal, or G1 is deleted;

G2 represents an arginine or glutamic acid residue if G1 is an arginine, lysine, ornithine, citrulline, alanine or glutamic acid residue which may be derivatized at N-terminal, or G2 represents an arginine or glutamic acid residue which may be derivatized at N-terminal if G1 is deleted;

G3 represents an aromatic amino acid residue;

G4, G5 and G9 each independently represents an arginine, lysine, ornithine, citrulline, alanine or glutamic acid residue;

G6 represents a proline, glycine, ornithine, lysine, alanine, citrulline, arginine or glutamic acid residue;

G7 represents a proline, glycine, ornithine, lysine, alanine, citrulline or arginine residue;

G8 represents a glutamic acid residue;

G10 represents a citrulline, glutamic acid, arginine or lysine residue;

G11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(11) Peptide represented by the following formula (Ih) or a salt thereof:

```
    1  2  3  4   5  6  7  8  9 10 11 12  13  14
    H1-H2-H3-Cys-Tyr-H4-H5-H6-H7-H8-H9-H10-Cys-H11
```
(Ih)

In this formula:

H1 is an arginine, lysine, ornithine, citrulline, alanine or glutamic acid residue which may be derivatized at N-terminal, or H1 is deleted;

H2 represents an arginine or glutamic acid residue if H1 is an arginine, lysine, ornithine, citrulline, alanine or glutamic acid residue which may be derivatized at N-terminal, or H2 represents an arginine or glutamic acid residue which may be derivatized at N-terminal if H1 is deleted;

H3 represents an aromatic amino acid residue;

H4 and H5 each independently represents an arginine, lysine, ornithine, citrulline, alanine or glutamic acid residue;

H6 represents a proline, glycine, ornithine, lysine, alanine, citrulline, arginine or glutamic acid residue;

H7 represents a proline, glycine, ornithine, lysine, alanine, citrulline or arginine residue;

H8 represents a tyrosine, phenylalanine, alanine, naphthylalanine, citrulline or glutamic acid residue;

H9 represents a glutamic acid residue;

H10 represents a citrulline, glutamic acid, arginine or lysine residue;

H11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(12) Peptide represented by the following formula (Ii) or a salt thereof:

```
    1  2  3  4   5  6  7  8  9 10 11 12  13  14
    I1-I2-I3-Cys-Tyr-I4-I5-I6-I7-I8-I9-I10-Cys-I11
```
(Ii)

In this formula:

I1 is an arginine, lysine, ornithine, citrulline, alanine or glutamic acid residue which may be derivatized at N-terminal, or I1 is deleted;

I2 represents an arginine or glutamic acid residue if I1 is an arginine, lysine, ornithine, citrulline, alanine or glutamic acid residue which may be derivatized at N-terminal, or I2 represents an arginine or glutamic acid residue which may be derivatized at N-terminal if I1 is deleted;

I3 represents an aromatic amino acid residue;

I4, I5 and I9 each independently represents an arginine, lysine, ornithine, citrulline, alanine or glutamic acid residue;

I6 represents a proline, glycine, ornithine, lysine, alanine, citrulline, arginine or glutamic acid residue;

I7 represents a proline, glycine, ornithine, lysine, alanine, citrulline or arginine residue;

I8 represents a tyrosine, phenylalanine, alanine, naphthylalanine, citrulline or glutamic acid residue;

I10 represents a glutamic acid, arginine or lysine residue;

I11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(13) Peptide represented by the following formula (Ij) or a salt thereof:

$$\begin{array}{cccccccccccccc}1&2&3&4&5&6&7&8&9&10&11&12&13&14\\ \text{J1-J2-J3-Cys-Tyr-J4-J5-J6-J7-J8-J9-J10-Cys-J11}\end{array} \quad (Ij)$$

In this formula:

J1 is an arginine, lysine, ornithine, citrulline, alanine or glutamic acid residue which may be derivatized at N-terminal, or J1 is deleted;

J2 represents an arginine or glutamic acid residue if J1 is an arginine, lysine, ornithine, citrulline, alanine or glutamic acid residue which may be derivatized at N-terminal, or J2 represents an arginine or glutamic acid residue which may be derivatized at N-terminal if J1 is deleted;

J3 represents an aromatic amino acid residue;

J4, J5 and J9 each independently represents an arginine, lysine, ornithine, citrulline, alanine or glutamic acid residue;

J6 represents a proline, glycine, ornithine, lysine, alanine, citrulline, arginine or glutamic acid residue;

J7 represents a proline, glycine, ornithine, lysine, alanine, citrulline or arginine residue;

J8 represents a tyrosine, phenylalanine, alanine, naphthylalanine, citrulline or glutamic acid residue;

J10 represents a citrulline, glutamic acid, arginine or lysine residue;

J11 represents a glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(14) Peptide indicated in any of the following items (1)-(58) or a salt thereof:

(1) Ac-Arg-Arg-Nal-Cys-Tyr-Cit-Lys-DLys-Pro-Tyr-Arg-Cit-Cys-Arg-OH;

(2) Ac-Arg-Arg-Nal-Cys-Tyr-Arg-Lys-DCit-Pro-Tyr-Arg-Cit-Cys-Arg-OH;

(3) Ac-Arg-Arg-Nal-Cys-Tyr-Cit-Lys-DCit-Pro-Tyr-Arg-Cit-Cys-Arg-OH;

(4) Ac-Arg-Arg-Nal-Cys-Tyr-Cit-Lys-DLys-Pro-Tyr-Cit-Cit-Cys-Arg-OH;

(5) Ac-Cit-Arg-Nal-Cys-Tyr-Cit-Lys-DLys-Pro-Tyr-Arg-Cit-Cys-Arg-OH;

(6) Ac-Cit-Arg-Nal-Cys-Tyr-Arg-Lys-DCit-Pro-Tyr-Arg-Cit-Cys-Arg-OH;

(7) Ac-Arg-Arg-Nal-Cys-Tyr-Arg-Lys-DCit-Pro-Tyr-Cit-Cit-Cys-Arg-OH;

(8) Ac-Cit-Arg-Nal-Cys-Tyr-Arg-Lys-DLys-Pro-Tyr-Cit-Cit-Cys-Arg-OH;

(9) Ac-Arg-Arg-Nal-Cys-Tyr-Cit-Lys-DCit-Pro-Tyr-Arg-Cit-Cys-Arg-NH$_2$;

(10) Ac-Arg-Arg-Nal-Cys-Tyr-Cit-Lys-DLys-Pro-Tyr-Cit-Cit-Cys-Arg-NH$_2$;

(11) Ac-Cit-Arg-Nal-Cys-Tyr-Cit-Lys-DLys-Pro-Tyr-Arg-Cit-Cys-Arg-NH$_2$;

(12) Ac-Cit-Arg-Nal-Cys-Tyr-Arg-Lys-DCit-Pro-Tyr-Arg-Cit-Cys-Arg-NH$_2$;

(13) Ac-Arg-Arg-Nal-Cys-Tyr-Arg-Lys-DCit-Pro-Tyr-Cit-Cit-Cys-Arg-NH$_2$;

(14) Ac-Cit-Arg-Nal-Cys-Tyr-Arg-Lys-DLys-Pro-Tyr-Cit-Cit-Cys-Arg-NH$_2$;

(15) H-DGlu-Arg-Nal-Cys-Tyr-Arg-Lys-DLys-Pro-Tyr-Arg-Cit-Cys-Arg-OH;

(16) H-Arg-Glu-Nal-Cys-Tyr-Arg-Lys-DLys-Pro-Tyr-Arg-Cit-Cys-Arg-OH;

(17) H-Arg-Arg-Nal-Cys-Tyr-Glu-Lys-DLys-Pro-Tyr-Arg-Cit-Cys-Arg-OH;

(18) H-Arg-Arg-Nal-Cys-Tyr-Arg-Glu-DLys-Pro-Tyr-Arg-Cit-Cys-Arg-OH;

(19) H-Arg-Arg-Nal-Cys-Tyr-Arg-Lys-DGlu-Pro-Tyr-Arg-Cit-Cys-Arg-OH;

(20) H-Arg-Arg-Nal-Cys-Tyr-Arg-Lys-DLys-Pro-Tyr-Glu-Cit-Cys-Arg-OH;

(21) H-Arg-Arg-Nal-Cys-Tyr-Arg-Lys-DLys-Pro-Tyr-Arg-Cit-Cys-Glu-OH;

(22) H-Arg-Arg-Nal-Cys-Tyr-Cit-Lys-DGlu-Pro-Tyr-Arg-Cit-Cys-Arg-NH$_2$;

(23) H-Arg-Arg-Nal-Cys-Tyr-DGlu-Lys-DCit-Pro-Tyr-Arg-Cit-Cys-Arg-NH$_2$;

(24) H-Arg-Arg-Nal-Cys-Tyr-DGlu-Lys-DGlu-Pro-Tyr-Arg-Cit-Cys-Arg-NH$_2$;

(25) H-DGlu-Arg-Nal-Cys-Tyr-Cit-Lys-DGlu-Pro-Tyr-Arg-Cit-Cys-Arg-NH$_2$;

(26) H-Arg-Arg-Nal-Cys-Tyr-Cit-Lys-DGlu-Pro-DGlu-Arg-Cit-Cys-Arg-NH$_2$;

(27) H-Arg-Arg-Nal-Cys-Tyr-Cit-Lys-DGlu-Pro-Tyr-Arg-DGlu-Cys-Arg-NH$_2$;

(28) Ac-DGlu-Arg-Nal-Cys-Tyr-Cit-Lys-DGlu-Pro-Tyr-Arg-Cit-Cys-Arg-NH$_2$;

(29) Ac-Arg-Arg-Nal-Cys-Tyr-Cit-Lys-DGlu-Pro-DGlu-Arg-Cit-Cys-Arg-NH$_2$;

(30) Ac-Arg-Arg-Nal-Cys-Tyr-Cit-Lys-DGlu-Pro-Tyr-Arg-DGlu-Cys-Arg-NH$_2$;

(31) Ac-Arg-Arg-Nal-Cys-Tyr-Cit-Lys-DGlu-Pro-Tyr-Arg-Cit-Cys-Arg-NH$_2$;

(32) guanyl-Arg-Arg-Nal-Cys-Tyr-Cit-Lys-DGlu-Pro-Tyr-Arg-Cit-Cys-Arg-NH$_2$;

(33) TMguanyl-Arg-Arg-Nal-Cys-Tyr-Cit-Lys-DGlu-Pro-Tyr-Arg-Cit-Cys-Arg-NH$_2$;

(34) TMguanyl-Arg-Nal-Cys-Tyr-Cit-Lys-DGlu-Pro-Tyr-Arg-Cit-Cys-Arg-NH$_2$;

(35) 4F-benzoyl-Arg-Arg-Nal-Cys-Tyr-Cit-Lys-DGlu-Pro-Tyr-Arg-Cit-Cys-Arg-NH$_2$;

(36) 2F-benzoyl-Arg-Arg-Nal-Cys-Tyr-Cit-Lys-DGlu-Pro-Tyr-Arg-Cit-Cys-Arg-NH$_2$;

(37) APA-Arg-Nal-Cys-Tyr-Cit-Lys-DGlu-Pro-Tyr-Arg-Cit-Cys-Arg-NH$_2$;

(38) desamino-R-Arg-Nal-Cys-Tyr-Cit-Lys-DGlu-Pro-Tyr-Arg-Cit-Cys-Arg-NH$_2$;

(39) guanyl-Arg-Arg-Nal-Cys-Tyr-Cit-Lys-DGlu-Pro-Tyr-Arg-Cit-Cys-Arg-NH$_2$;

(40) succinyl-Arg-Nal-Cys-Tyr-Cit-Lys-DGlu-Pro-Tyr-Arg-Cit-Cys-Arg-NH₂;
(41) glutaryl-Arg-Nal-Cys-Tyr-Cit-Lys-DGlu-Pro-Tyr-Arg-Cit-Cys-Arg-NH₂;
(42) deaminoTMG-APA-Arg-Nal-Cys-Tyr-Cit-Lys-DGlu-Pro-Tyr-Arg-Cit-Cys-Arg-NH₂;
(43) nelfinaviryl-succinyl-Arg-Nal-Cys-Tyr-Cit-Lys-DGlu-Pro-Tyr-Arg-Cit-Cys-Arg-NH₂;
(44) AZT-glutaryl-Arg-Nal-Cys-Tyr-Cit-Lys-DGlu-Pro-Tyr-Arg-Cit-Cys-Arg-NH₂;
(45) R—CH2-Arg-Nal-Cys-Tyr-Cit-Lys-DGlu-Pro-Tyr-Arg-Cit-Cys-Arg-NH₂;
(46) H-Arg-Nal-Cys-Tyr-Cit-Lys-DGlu-Pro-Tyr-Arg-Cit-Cys-Arg-NH₂;
(47) TMguanyl-Arg-Arg-Nal-Cys-Tyr-Cit-Lys-DCit-Pro-Tyr-Arg-Cit-Cys-Arg-NH₂;
(48) ACA-Arg-Arg-Nal-Cys-Tyr-Cit-Lys-DCit-Pro-Tyr-Arg-Cit-Cys-Arg-NH₂;
(49) ACA-Arg-Arg-Nal-Cys-Tyr-Arg-Lys-DLys-Pro-Tyr-Arg-Cit-Cys-Arg-OH;
(50) H-Arg-Arg-Nal-Cys-Tyr-Cit-Arg-DLys-Pro-Tyr-Arg-Cit-Cys-Arg-NH₂;
(51) Ac-Arg-Arg-Nal-Cys-Tyr-Cit-Arg-DLys-Pro-Tyr-Arg-Cit-Cys-Arg-NH₂;
(52) Ac-Arg-Arg-Nal-Cys-Tyr-Cit-Lys-DLys-Pro-Tyr-Arg-Cit-Cys-Arg-NH₂;
(53) Ac-Arg-Arg-Nal-Cys-Tyr-Arg-Lys-DCit-Pro-Tyr-Arg-Cit-Cys-Arg-NH₂;
(54) 4F-benzoyl-Arg-Arg-Nal-Cys-Tyr-Cit-Lys-DLys-Pro-Tyr-Arg-Cit-Cys-Arg-NH₂
(55) 4F-benzoyl-Arg-Arg-Nal-Cys-Tyr-Cit-Lys-DGlu-Pro-Tyr-Arg-Cit-Cys-Arg-NHMe
(56) 4F-benzoyl-Arg-Arg-Nal-Cys-Tyr-Cit-Lys-DGlu-Pro-Tyr-Arg-Cit-Cys-Arg-NHEt
(57) 4F-benzoyl-Arg-Arg-Nal-Cys-Tyr-Cit-Lys-DGlu-Pro-Tyr-Arg-Cit-Cys-Arg-NHiPr
(58) 4F-benzoyl-Arg-Arg-Nal-Cys-Tyr-Cit-Lys-DGlu-Pro-Tyr-Arg-Cit-Cys-Arg-tyramine In each sequence, the symbol put in the left part of N-terminal amino acid shows derivatization or non-derivatization of amino group; H shows non-derivatization, Ac shows acetyl group, guanyl shows guanyl group, succinyl shows succinyl group, glutaryl shows glutaryl group, TMguanyl shows tetramethyl guanyl group, 2F-beozoyl shows 2-fluorobenzoyl group, 4F-benzoyl shows 4-fluorobenzoly group, APA shows 5-amino-pentanoyl group, ACA shows 6-amino-hexanoyl group, desamino-R shows 2-desamino-arginyl group, deaminoTMG-APA shows the following formula (II),

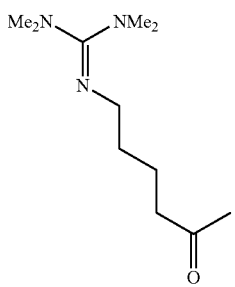

(II)

nelfinaviryl-succinyl shows the following formula (III)

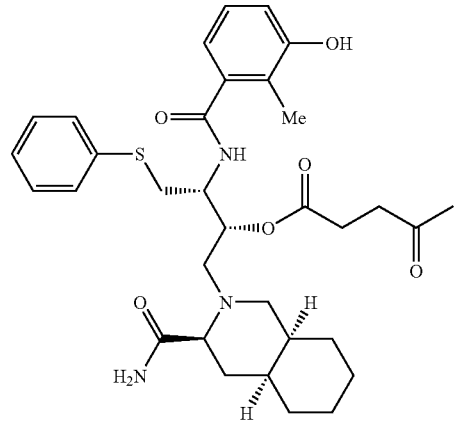

(III)

AZT-glutaryl shows the following formula (IV)

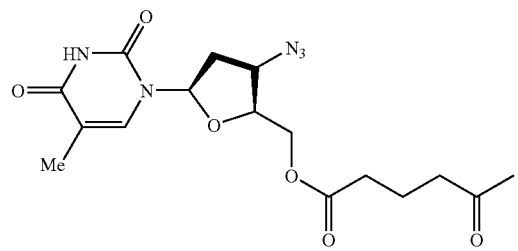

(IV)

R—CH2 shows the following formula (V)

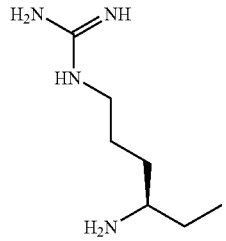

(V)

Arg shows L-arginine residue, Nal show L-3-2(2-naphtyl) alanine residue, Cys shows L-cysteine residue, Tyr shows L-tyrosine residue, Cit shows L-citrulline residue, Lys shows L-lysine residue, DLys shows D-lysine residue, Pro shows L-proline residue, DCit shows D-citrulline residue, DGlu shows D-glutamic acid residue, Glu shows L-glutamic acid residue, 2 cysteine residues are combined by intramolecular disulfide bond, the symbol attached to the right part of C-terminal amino acid shows derivatization or non-derivatization of carboxyl group, OH shows non-derivatization, NH₂ shows amidation by amino group, NHMe shows amidation by methyamino group, NHEt shows amidation by ethylamino group, NHiPr shows amidation by isopropylamino group, tyramine shows amidation by p-hydroxy phenyl ethylamino group.

(15) Pharmaceutical products containing any of the peptides stated in any of (3) to (14) or any salt of the peptide.
(16) CXCR4 antagonists belonging to the pharmaceutical products stated in (15).

(17) Preventive and/or therapeutic medicines for cancers or chronic rheumatoid arthritis belonging to the pharmaceutical products stated in (15).

(18) Medicines stated in (17) usable for breast cancer or pancreas cancer.

(19) Preventive and/or therapeutic methods for cancers or chronic rheumatoid arthritis by administration to mammalians of effective doses of a peptide stated in any of (3) to (14) or a salt thereof.

(20) Use of a peptide stated in any of (3) to (14) or a salt thereof for the manufacturing of preventive and/or therapeutic medicines for cancers or chronic rheumatoid arthritis.

(21) Preventive and/or therapeutic methods for cancers or chronic rheumatoid arthritis by administration to mammalians of effective doses of a peptide represented by the following formula (Ia) or a salt thereof:

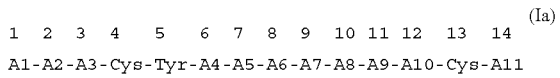

In this formula:

A1 is an arginine, lysine, ornithine, citrulline, alanine or glutamic acid residue which may be derivatized at N-terminal, or A1 is deleted;

A2 represents an arginine or glutamic acid residue if A1 are an arginine, lysine, ornithine, citrulline, alanine or glutamic acid residue which may be derivatized at N-terminal, or A2 represents an arginine or glutamic acid residue which may be derivatized at N-terminal if A1 is deleted;

A3 represents an aromatic amino acid residue;

A4, A5 and A9 each independently represents an arginine, lysine, ornithine, citrulline, alanine or glutamic acid residue;

A6 represents a proline, glycine, ornithine, lysine, alanine, citrulline, arginine or glutamic acid residue;

A7 represents a proline, glycine, ornithine, lysine, alanine, citrulline or arginine residue;

A8 represents a tyrosine, phenylalanine, alanine, naphthylalanine, citrulline or glutamic acid residue;

A10 represents a citrulline, glutamic acid, arginine or lysine residue;

A11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(22) Use of a peptide represented by the following formula (Ia) or a salt thereof for the manufacturing of preventive and/or therapeutic medicines for cancers or chronic rheumatoid arthritis:

In this formula:

A1 is an arginine, lysine, ornithine, citrulline, alanine or glutamic acid residue which may be derivatized at N-terminal, or A1 is deleted;

A2 represents an arginine or glutamic acid residue if A1 is an arginine, lysine, ornithine, citrulline, alanine or glutamic acid residue which may be derivatized at N-terminal, or A2 represents an arginine or glutamic acid residue which may be derivatized at N-terminal if A1 is deleted;

A3 represents an aromatic amino acid residue;

A4, A5 and A9 each independently represents an arginine, lysine, ornithine, citrulline, alanine or glutamic acid residue;

A6 represents a proline, glycine, ornithine, lysine, alanine, citrulline, arginine or glutamic acid residue;

A7 represents a proline, glycine, ornithine, lysine, alanine, citrulline or arginine residue;

A8 represents a tyrosine, phenylalanine, alanine, naphthylalanine, citrulline or glutamic acid residue;

A10 represents a citrulline, glutamic acid, arginine or lysine residue;

A11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

The peptidic compounds of the present invention have potent CXCR4 antagonistic activity, and show therapeutic effects for cancers and chronic rheumatoid arthritis by inhibiting the interaction of CXCR4 and CXCL12/SDF-1.

BRIEF DESCRIPTION OF THE DRAWINGS

FIG. 5A displays the lungs of the control group (saline administration group).

FIG. 5B is the pictures of the lungs of 4Fbenzoyl-TN-14003 administration group.

FIG. 9A shows fluctuations in body weight [vertical axis: body weight gain (g) (mean value±standard margin of error, n=8), horizontal axis: post-booster days];

FIG. 9B shows fluctuations of the incidence of the disease [vertical axis: incidence (%) (n=8), horizontal axis: post-booster days];

FIG. 9C shows fluctuations of arthritis score [vertical axis: arthritis score (mean value±standard margin of error, n=8), horizontal axis: post-booster days];

FIG. 9D shows fluctuations of ankle thickness [vertical axis: ankle thickness (mm) (mean value±standard margin of error, n=8), horizontal axis: post-booster days]. : normal mouse group, : drug non-administration (control) group, Δ: indomethacin administration group, : ethotrexate administration group, : FK506 administration group;

FIG. 9E shows each drug's effect on hindlimb swelling 2 weeks after the booster [vertical axis: hindlimb weight (mg) (average amount±standard margin of error, n=8)]; and FIG. 9F shows each drug's effect on anti-bovine II collagen IgG2a antibody value 2 weeks after the booster [vertical axis: antibody value (A450) (mean value±standard margin of error, n=8)] [from the left, it shows normal mouse group, drug non-administration (control) group, indomethacin (IND) administration group, methotrexate (MTX) administration group, FK506 administration group]. ## is P 0.01 (comparison with normal mice group; t-test), * and ** respectively show P 0.05 and P 0.01 (comparison with drug non-administration group; Dunnett's test).

FIG. 10 shows the activity of 4Fbenzoyl-TN-14003 on mouse collagen-induced arthritis.

BEST MODE FOR CARRYING OUT THE INVENTION

Figure 1:
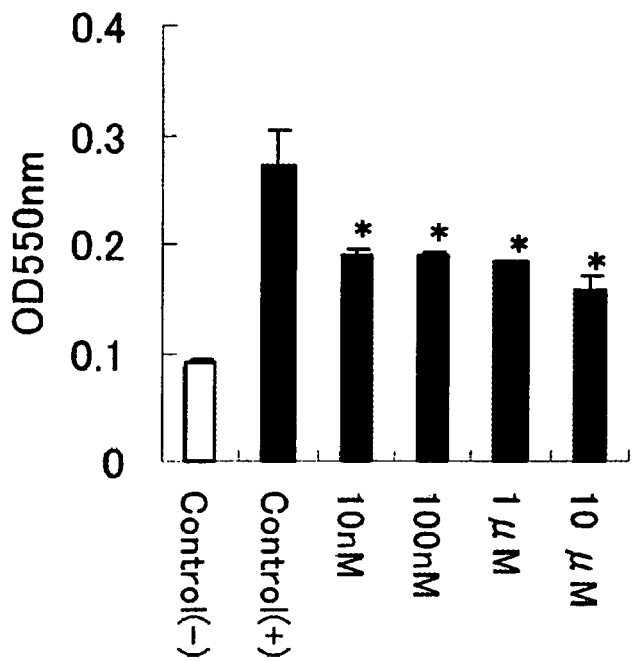
FIG. 1 shows the inhibitory activity of TE-14005 against the migration of breast cancer cells induced by CXCL12. The vertical axis shows the migration of cells (absorption of light: OD550 nm). From the left, it shows the result (mean value±standard deviation, n=2) obtained respectively when CXCL12 was not added (negative control), when CXCL12 was added (positive control), when CXCL12 and TE-14005 10 nM were added, when CXCL12 and TE-14005 100 nM were added, when CXCL12 and TE-14005 1 µM were added, and when CXCL12 and TE-14005 10 µM were added. * indicates the significance of each TE-14005 added group compared with the positive control group (Williams' test, p 0.025).

The peptides described in this specification have N-terminal (amino-terminal) at the left extremity and C-terminal (carboxyl-terminal at the right extremity in accordance with the customary practice of peptide notations.

In this specification and drawings, the representations of amino acids, etc. by brevity codes are made by the use of the codes prescribed by IUPAC-IUB Commission on Biochemical Nomenclature or by the codes customarily used in the relevant art. Examples of such codes are shown as below. If an optical isomer exists with respect to an amino acid, it represents L form unless otherwise expressly specified.

| | |
|---|---|
| Gly or G: | glycine |
| Ala or A: | alanine |
| Val or V: | valine |
| Leu or L: | leucine |
| Ile or I: | isoleucine |
| Ser or S: | serine |
| Thr or T: | threonine |
| Cys or C: | cysteine |
| Met or M: | methionine |
| Glu or E: | glutamic acid |
| Asp or D: | aspartic acid |
| Lys or K: | lysine |
| Arg or R: | arginine |
| His or H: | histidine |
| Phe or F: | phenylalanine |
| Tyr or Y: | tyrosine |
| Trp or W: | tryptophan |
| Pro or P: | proline |
| Asn or N: | asparagine |
| Gln or Q: | glutamine |
| pGlu: | pyroglutamic acid |
| Nal: | 3-(2-naphthyl) alanine |
| Cit: | citrulline |
| DLys: | D-lysine |
| DCit: | D-citrulline |
| DGlu: | D-glutamic acid |
| Me: | methyl group |
| Et: | ethyl group |
| Bu: | butyl group |
| Ph: | phenyl group |

The substituents, protective group and reagents often used in this specification are indicated by the following codes.

| | |
|---|---|
| BHA: | benzhydrylamine |
| pMBHA: | p-methylbenzhydrylamine |
| Tos: | p-toluenesulphonyl |
| CHO: | formyl |
| HONB: | N-hydroxy-5-norbornene-2,3-dicarboximide |
| OcHex: | cyclohexyl ester |
| Bzl: | benzyl |
| Cl2-Bzl: | dichloro-benzyl |
| Bom: | benzyloxymethyl |
| Z: | benzyloxycarbonyl |
| Br-Z: | 2-bromobenzyloxycarbonyl |
| Boc: | t-butyloxycarbonyl |
| DCM: | dichloromethane |
| HOBt: | 1-hydroxybenzotriazole |
| DCC: | N,N'-dicyclohexylcarbodiimide |
| TFA: | trifluoroacetic acid |
| DIEA: | diisopropylethylamine |
| Fmoc: | N-9-fluorenylmethoxycarbony |
| DNP: | dinitrophenyl |
| Bum: | tertiarybutoxymethyl |
| Trt: | trityl |
| Ac: | acetyl |
| Guanyl: | guanyl |
| Succinyl: | succinyl |
| glutaryl: | glutaryl |
| TMguanyl: | tetramethylguanyl |
| 2F-benzoyl: | 2-fluorobenzoyl |
| 4F-benzoyl: | 4-fluorobenzoyl |
| APA: | 5-aminopentanoyl |
| ACA: | 6-aminohexanoyl |
| desamino-Arg: | 2-desamino-arginyl | deamino TMG-APA: the following formula (II)

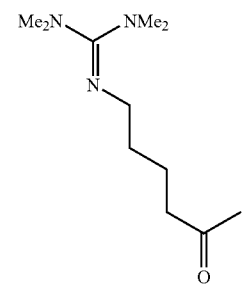

nelfinaviryl-succinyl: the following formula (III)

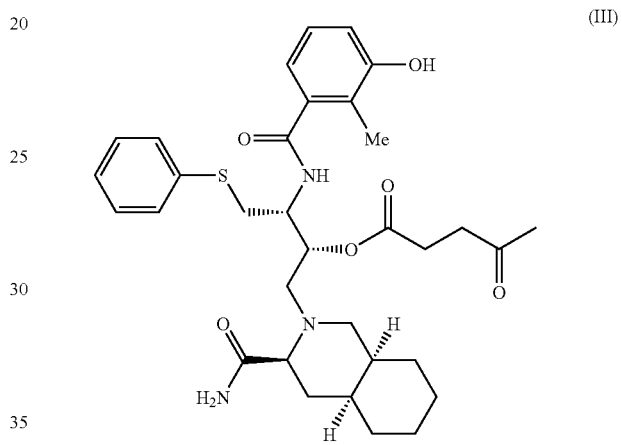

AZT-glutaryl: the following formula (IV)

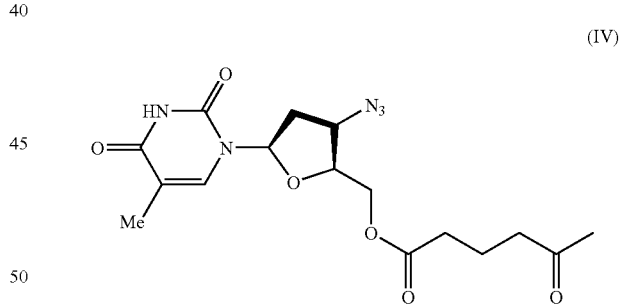

R—CH: the following formula (V)

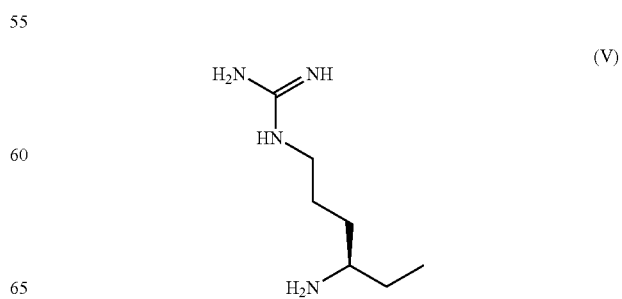

In amino acids of N-terminal peptide, [H—] indicates that terminalamino group is not derivatized, and in amino acids of C-terminal peptide, [—OH] indicates that terminal carboxyl group is not derivatized.

The present invention provides preventive and/or therapeutic medicines containing CXCR4 antagonistic compounds for cancers and chronic rheumatoid arthritis. The "CXCR4 antagonistic compounds" show anti-cancer activity antagonistically inhibiting the interaction of CXCR4 and its physiological ligand CXCL12/SDF-1α (e.g. migration inhibitory activity, invasion inhibitory activity, and anti-metastasis activity, etc.) or anti-chronic rheumatoid arthritis activity (e.g. migration inhibitory activity), and more particularly, they include the peptide represented by the following formula (Ia), an amide thereof, an ester thereof or a salt thereof (hereinafter as may be collectively referred to as "peptide(s) of the present invention"):

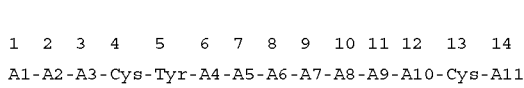

(Ia)

In this formula:
A1 is an arginine, lysine, ornithine, citrulline, alanine or glutamic acid residue which may be derivatized at N-terminal, or A1 is deleted;
A2 represents an arginine or glutamic acid residue if A1 is an arginine, lysine, ornithine, citrulline, alanine or glutamic acid residue which may be derivatized at N-terminal, or A2 represents an arginine or glutamic acid residue which may be derivatized at N-terminal if A1 is deleted;
A3 represents an aromatic amino acid residue;
A4, A5 and A9 each independently represents an arginine, lysine, ornithine, citrulline, alanine or glutamic acid residue;
A6 represents a proline, glycine, ornithine, lysine, alanine, citrulline, arginine or glutamic acid residue;
A7 represents a proline, glycine, ornithine, lysine, alanine, citrulline or arginine residue;
A8 represents a tyrosine, phenylalanine, alanine, naphthylalanine, citrulline or glutamic acid residue;
A10 represents a citrulline, glutamic acid, arginine or lysine residue;
A11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

A1 in the above-mentioned formula (Ia) represents an arginine, lysine, ornithine, citrulline, alanine or glutamic acid residue (either L or D form) which may be derivatized at N-terminal, or A1 is deleted, or it is preferable that A1 is an arginine, citrulline, alanine or D-glutamic acid residue, or A1 is deleted.

Examples of "peptides derivatized at N-terminal" include, but are not limited to, those protected by formyl group; acyl group, e.g., acetyl group, propionyl group, butyryl group, pentanoyl group, C2-6alkanoyl group such as hexanoyl group, benzoyl group, arylcarbonyl group such as substituted benzoyl group (e.g.: 2-fluorobenzoyl, 3-fluorobenzoyl group, 4-fluorobenzoyl group, 2-bromobenzoyl group, 3-bromobenzoyl group, 4-bromobenzoyl group, 2-nitrobenzoyl group, 3-nitrobezoyl group, 4-nirtobenzoyl group), succinyl group, glutaryl group; nicotinyl group; isonicotinyl group; alkylsulfonyl group (e.g.: methanesulfonyl group, ethanesulfonyl group, propanesulfonyl group, camphorsulfonyl group); arylsulfonyl group (e.g.: p-toluenesulfonyl group, 4-fluorobenzenesufonyl group, mesitylenesulfonyl group, 4-aminobenzenesulfonyl group, dansyl group, 4-bromobenzenesulfonyl group) etc. Or, the amino acid group of N-terminal may be deleted.

A2 in the above-mentioned formula (Ia) represents an arginine or glutamic acid residue (either L or D form) if A1 is an arginine, lysine, ornithine, citrulline, alanine or glutamic acid residue (either L or D form) which may be derivatized at N-terminal, or A2 represents an arginine or glutamic acid residue (either L or D form) which may be derivatized at N-terminal if A1 is deleted, or it is preferable that A2 is an arginine or glutamic acid residue if A1 is an arginine, citrulline, alanine or glutamic acid residue which may be derivatized at N-terminal, or A2 is an arginine or glutamic acid residue which may be derivatized at N-terminal if A1 is deleted.

Examples of "peptides derivatized at N-terminal" include, but are not limited to, the same ones as those mentioned in A1.

A3 in the above-mentioned formula (Ia) represents an aromatic amino acid residue (e.g., phenylalanine, tryptophan, 3-(2-naphthyl)alanine, tyrosine, 4-fluorophenylalanine, 3-(1-naphthyl)alanine (either L or D form), or preferably, A3 represents phenylalanine, tryptophan or 3-(2-naphthyl)alanine.

A4 in the above-mentioned formula (Ia) represents an arginine, lysine, ornithine, citrulline, alanine or glutamic acid residue (either L or D form), or it is preferable that A4 is an arginine, citrulline, alanine or L- or D-glutamic acid residue.

A5 in the above-mentioned formula (Ia) represents an arginine, lysine, ornithine, citrulline, alanine or glutamic acid residue, or it is preferable that A5 is an arginine, citrulline, alanine, lysine or glutamic acid residue.

A6 in the above-mentioned formula (Ia) represents a proline, glycine, ornithine, lysine, alanine, citrulline, arginine or glutamic acid residue (either L or D form), or it is preferable that A6 is a D-lysine, D-alanine, D-citrulline or D-glutamic acid residue.

A7 in the above-mentioned formula (Ia) represents a proline, glycine, ornithine, lysine, alanine, citrulline or arginine residue (either L or D form), or it is preferable that A7 is a proline or alanine residue.

A8 in the above-mentioned formula (Ia) represents a tyrosine, phenylalanine, alanine, naphthylalanine, citrulline or glutamic acid residue (either L or D form), or it is preferable that A8 is a tyrosine, alanine or D-glutamic acid residue.

A9 in the above-mentioned formula (Ia) represents an arginine, lysine, ornithine, citrulline, alanine or glutamic acid residue (either L or D form), or it is preferable that A9 is an arginine, citrulline or glutamic acid residue.

A10 in the above-mentioned formula (Ia) represents a citrulline, glutamic acid, arginine or lysine residue (either L or D form), or it is preferable that A10 is a citrulline or D-glutamic acid residue.

A11 in the above-mentioned formula (Ia) represents an arginine, glutamic acid, lysine or citrulline residue (either L or D form) which may be derivatized at C-terminal, or it is preferable that A11 is an arginine or glutamic acid residue which may be derivatized at C-terminal.

"Derivatization at C-terminal" includes, without limitation, amidation (—CONH$_2$, —CONHR, —CONRR') and esterification (—COOR). Herein, R and R' in amides and esters include, for example, C1-6 alkyl group such as methyl, ethyl, n-propyl, isopropyl, or n-butyl, C3-8 cycloalkyl group such as cyclopentyl, cyclohexyl, C6-12 aryl group such as phenyl and α-naphthyl, phenyl-C1-2 alkyl group such as benzyl, phenethyl or C7-14 aralkyl group such as C1-2 alkyl group such as α-naphthyl methyl group, and additionally, pivaloyloxymethyl group which is generally used as an oral bioavailable ester.

If a peptide of the present invention has carboxy groups (or carboxylates) at side-chain terminals other than C-terminal, the peptide having amidated or esterificated carboxy groups at side-chain terminals is included in the peptides of the present invention. As the amides and esters in this case, for example, the amides and esters exemplified in A11 are similarly used. Also, the peptides of the present invention include peptides in which substituents (e.g. —OH, —SH, amino group, imidazole group, indole group, guanidino group, etc.) on the intramolecular amino acid side chains are protected by suitable protective group (e.g. C1-6 acyl group, C2-6 alkanoyl such as formyl group, acetyl group, etc.), or complex peptides such as glycopeptides combined with sugar chain in the above-mentioned peptides.

Salts of the peptides of the present invention include physiologically acceptable salts of acids or bases and particularly, physiologically acceptable acid addition salts are preferable. Such salts are exemplified by salts of inorganic acids (e.g. hydrochloric acid, phosphoric acid, hydrobromic acid, sulfuric acid), or salts of organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

A peptide of the present invention is a new peptide if any one of A1 to A11 indicated in the above-mentioned formula (Ia) is the following:
(i) If A1 is a glutamic acid residue or is deleted (i.e. the same as the above-mentioned formula (Ib));
(ii) If any one of A2, A4, A6, A8 and A9 is a glutamic acid residue (i.e. the same as any of the above-mentioned formula (Ic) to (Ig)):
(iii) If A5 is an arginine or glutamic acid residue (i.e. the same as the above-mentioned formula (Ih)):
(iv) If A10 is a glutamic acid, arginine or lysine residue (i.e. the same as the above-mentioned formula (Ii)):
(v) If A11 is a glutamic acid, lysine or citrulline residue (i.e. the same as the above-mentioned formula (Ij)).

The above-mentioned amino acid residues may be either L or D form.

As the peptides of the present invention, preferably the peptides having the amino acid sequences of the following (1) to (58) (in each sequence, two cysteine residues are coupled by the disulfide bond) are exemplified.

(1) Ac-Arg-Arg-Nal-Cys-Tyr-Cit-Lys-DLys-Pro-Tyr-Arg-Cit-Cys-Arg-OH (AcTC14003)
(2) Ac-Arg-Arg-Nal-Cys-Tyr-Arg-Lys-DCit-Pro-Tyr-Arg-Cit-Cys-Arg-OH (AcTC14005)
(3) Ac-Arg-Arg-Nal-Cys-Tyr-Cit-Lys-DCit-Pro-Tyr-Arg-Cit-Cys-Arg-OH (AcTC14011)
(4) Ac-Arg-Arg-Nal-Cys-Tyr-Cit-Lys-DLys-Pro-Tyr-Cit-Cit-Cys-Arg-OH (AcTC14013)
(5) Ac-Cit-Arg-Nal-Cys-Tyr-Cit-Lys-DLys-Pro-Tyr-Arg-Cit-Cys-Arg-OH (AcTC14015)
(6) Ac-Cit-Arg-Nal-Cys-Tyr-Arg-Lys-DCit-Pro-Tyr-Arg-Cit-Cys-Arg-OH (AcTC14017)
(7) Ac-Arg-Arg-Nal-Cys-Tyr-Arg-Lys-DCit-Pro-Tyr-Cit-Cit-Cys-Arg-OH (AcTC14019)
(8) Ac-Cit-Arg-Nal-Cys-Tyr-Arg-Lys-DLys-Pro-Tyr-Cit-Cit-Cys-Arg-OH (AcTC14021)
(9) Ac-Arg-Arg-Nal-Cys-Tyr-Cit-Lys-DCit-Pro-Tyr-Arg-Cit-Cys-Arg-NH$_2$ (AcTC14012)
(10) Ac-Arg-Arg-Nal-Cys-Tyr-Cit-Lys-DLys-Pro-Tyr-Cit-Cit-Cys-Arg-NH$_2$ (AcTC14014)
(11) Ac-Cit-Arg-Nal-Cys-Tyr-Cit-Lys-DLys-Pro-Tyr-Arg-Cit-Cys-Arg-NH$_2$ (AcTC14016)
(12) Ac-Cit-Arg-Nal-Cys-Tyr-Arg-Lys-DCit-Pro-Tyr-Arg-Cit-Cys-Arg-NH$_2$ (AcTC14018)
(13) Ac-Arg-Arg-Nal-Cys-Tyr-Arg-Lys-DCit-Pro-Tyr-Cit-Cit-Cys-Arg-NH$_2$ (AcTC14020)
(14) Ac-Cit-Arg-Nal-Cys-Tyr-Arg-Lys-DLys-Pro-Tyr-Cit-Cit-Cys-Arg-NH$_2$ (AcTC14022)
(15) H-DGlu-Arg-Nal-Cys-Tyr-Arg-Lys-DLys-Pro-Tyr-Arg-Cit-Cys-Arg-OH (TE14001)
(16) H-Arg-Glu-Nal-Cys-Tyr-Arg-Lys-DLys-Pro-Tyr-Arg-Cit-Cys-Arg-OH (TE14002)
(17) H-Arg-Arg-Nal-Cys-Tyr-Glu-Lys-DLys-Pro-Tyr-Arg-Cit-Cys-Arg-OH (TE14003)
(18) H-Arg-Arg-Nal-Cys-Tyr-Arg-Glu-DLys-Pro-Tyr-Arg-Cit-Cys-Arg-OH (TE14004)
(19) H-Arg-Arg-Nal-Cys-Tyr-Arg-Lys-DGlu-Pro-Tyr-Arg-Cit-Cys-Arg-OH (TE14005)
(20) H-Arg-Arg-Nal-Cys-Tyr-Arg-Lys-DLys-Pro-Tyr-Glu-Cit-Cys-Arg-OH (TE14006)
(21) H-Arg-Arg-Nal-Cys-Tyr-Arg-Lys-DLys-Pro-Tyr-Arg-Cit-Cys-Glu-OH (TE14007)
(22) H-Arg-Arg-Nal-Cys-Tyr-Cit-Lys-DGlu-Pro-Tyr-Arg-Cit-Cys-Arg-NH$_2$ (TE14011)
(23) H-Arg-Arg-Nal-Cys-Tyr-DGlu-Lys-DCit-Pro-Tyr-Arg-Cit-Cys-Arg-NH$_2$ (TE14012)
(24) H-Arg-Arg-Nal-Cys-Tyr-DGlu-Lys-DGlu-Pro-Tyr-Arg-Cit-Cys-Arg-NH$_2$ (TE14013)
(25) H-DGlu-Arg-Nal-Cys-Tyr-Cit-Lys-DGlu-Pro-Tyr-Arg-Cit-Cys-Arg-NH$_2$ (TE14014)
(26) H-Arg-Arg-Nal-Cys-Tyr-Cit-Lys-DGlu-Pro-DGlu-Arg-Cit-Cys-Arg-NH$_2$ (TE14015)
(27) H-Arg-Arg-Nal-Cys-Tyr-Cit-Lys-DGlu-Pro-Tyr-Arg-DGlu-Cys-Arg-NH$_2$ (TE14016)
(28) Ac-DGlu-Arg-Nal-Cys-Tyr-Cit-Lys-DGlu-Pro-Tyr-Arg-Cit-Cys-Arg-NH$_2$ (AcTE14014)
(29) Ac-Arg-Arg-Nal-Cys-Tyr-Cit-Lys-DGlu-Pro-DGlu-Arg-Cit-Cys-Arg-NH$_2$ (AcTE14015)
(30) Ac-Arg-Arg-Nal-Cys-Tyr-Cit-Lys-DGlu-Pro-Tyr-Arg-DGlu-Cys-Arg-NH$_2$ (AcTE14016)
(31) Ac-Arg-Arg-Nal-Cys-Tyr-Cit-Lys-DGlu-Pro-Tyr-Arg-Cit-Cys-Arg-NH$_2$ (TF1: AcTE14011)
(32) guanyl-Arg-Arg-Nal-Cys-Tyr-Cit-Lys-DGlu-Pro-Tyr-Arg-Cit-Cys-Arg-NH$_2$ (TF2: guanyl-TE14011)
(33) TMguanyl-Arg-Arg-Nal-Cys-Tyr-Cit-Lys-DGlu-Pro-Tyr-Arg-Cit-Cys-Arg-NH$_2$ (TF3: TMguanyl-TE14011)
(34) TMguanyl-Arg-Nal-Cys-Tyr-Cit-Lys-DGlu-Pro-Tyr-Arg-Cit-Cys-Arg-NH$_2$ (TF4: TMguanyl-TE14011 (2-14))
(35) 4F-benzoyl-Arg-Arg-Nal-Cys-Tyr-Cit-Lys-DGlu-Pro-Tyr-Arg-Cit-Cys-Arg-NH$_2$ (TF5: 4F-benzoyl-TE14011)
(36) 2F-benzoyl-Arg-Arg-Nal-Cys-Tyr-Cit-Lys-DGlu-Pro-Tyr-Arg-Cit-Cys-Arg-NH$_2$ (TF6: 2F-benzoyl-TE14011)
(37) APA-Arg-Nal-Cys-Tyr-Cit-Lys-DGlu-Pro-Tyr-Arg-Cit-Cys-Arg-NH$_2$ (TF7: APA-TE14011 (2-14))
(38) desamino-R-Arg-Nal-Cys-Tyr-Cit-Lys-DGlu-Pro-Tyr-Arg-Cit-Cys-Arg-NH$_2$ (TF8: desamino-R-TE14011 (2-14))
(39) guanyl-Arg-Nal-Cys-Tyr-Cit-Lys-DGlu-Pro-Tyr-Arg-Cit-Cys-Arg-NH$_2$ (TF9: guanyl-TE14011 (2-14))
(40) succinyl-Arg-Nal-Cys-Tyr-Cit-Lys-DGlu-Pro-Tyr-Arg-Cit-Cys-Arg-NH$_2$ (TF10: succinyl-TE14011 (2-14))
(41) glutaryl-Arg-Nal-Cys-Tyr-Cit-Lys-DGlu-Pro-Tyr-Arg-Cit-Cys-Arg-NH$_2$ (TF11: glutaryl-TE14011 (2-14))

(42) deaminoTMG-APA-Arg-Nal-Cys-Tyr-Cit-Lys-DGlu-Pro-Tyr-Arg-Cit-Cys-Arg-NH$_2$ (TF12: deaminoTMG-APA-TE14011 (2-14))
(43) nelfinaviryl-succinyl-Arg-Nal-Cys-Tyr-Cit-Lys-DGlu-Pro-Tyr-Arg-Cit-Cys-Arg-NH$_2$ (TF13: nelfinaviryl-succinyl-TE14011 (2-14))
(44) AZT-glutaryl-Arg-Nal-Cys-Tyr-Cit-Lys-DGlu-Pro-Tyr-Arg-Cit-Cys-Arg-NH$_2$ (TF14: AZT-glutaryl-TE14011 (2-14))
(45) R—CH2-Arg-Nal-Cys-Tyr-Cit-Lys-DGlu-Pro-Tyr-Arg-Cit-Cys-Arg-NH$_2$ (TF15: H-Arg-CH2NH-RTE14011 (2-14))
(46) H-Arg-Nal-Cys-Tyr-Cit-Lys-DGlu-Pro-Tyr-Arg-Cit-Cys-Arg-NH$_2$ (TF17: TE14011 (2-14))
(47) TMguanyl-Arg-Arg-Nal-Cys-Tyr-Cit-Lys-DCit-Pro-Tyr-Arg-Cit-Cys-Arg-NH$_2$ (TF18: TMguanyl-TC14012)
(48) ACA-Arg-Arg-Nal-Cys-Tyr-Cit-Lys-DCit-Pro-Tyr-Arg-Cit-Cys-Arg-NH$_2$ (TF19: ACA-TC14012)
(49) ACA-Arg-Arg-Nal-Cys-Tyr-Arg-Lys-DLys-Pro-Tyr-Arg-Cit-Cys-Arg-OH (TF20: ACA-T140)
(50) H-Arg-Arg-Nal-Cys-Tyr-Cit-Arg-DLys-Pro-Tyr-Arg-Cit-Cys-Arg-NH$_2$ (TZ14011)
(51) Ac-Arg-Arg-Nal-Cys-Tyr-Cit-Arg-DLys-Pro-Tyr-Arg-Cit-Cys-Arg-NH$_2$ (AcTZ14011)
(52) Ac-Arg-Arg-Nal-Cys-Tyr-Cit-Lys-DLys-Pro-Tyr-Arg-Cit-Cys-Arg-NH$_2$ (AcTN14003)
(53) Ac-Arg-Arg-Nal-Cys-Tyr-Arg-Lys-DCit-Pro-Tyr-Arg-Cit-Cys-Arg-NH$_2$ (AcTN14005)
(54) 4F-benzoyl-Arg-Arg-Nal-Cys-Tyr-Cit-Lys-DLys-Pro-Tyr-Arg-Cit-Cys-Arg-NH$_2$ (4F-benzoyl-TN14003)
(55) 4F-benzoyl-Arg-Arg-Nal-Cys-Tyr-Cit-Lys-DGlu-Pro-Tyr-Arg-Cit-Cys-Arg-NHMe (4F-benzoyl-TN 14011-Me)
(56) 4F-benzoyl-Arg-Arg-Nal-Cys-Tyr-Cit-Lys-DGlu-Pro-Tyr-Arg-Cit-Cys-Arg-NHEt (4F-benzoyl-TN 14011-Et)
(57) 4F-benzoyl-Arg-Arg-Nal-Cys-Tyr-Cit-Lys-DGlu-Pro-Tyr-Arg-Cit-Cys-Arg-NHiPr (4F-benzoyl-TN 14011-iPr)
(58) 4F-benzoyl-Arg-Arg-Nal-Cys-Tyr-Cit-Lys-DGlu-Pro-Tyr-Arg-Cit-Cys-Arg-tyramine (4F-benzoyl-TN14011-tyramine)

A peptide of the present invention includes a peptide or its amide, ester or salt containing the amino acid sequence which is the substantially same amino acid sequence as the sequence of any of the above-mentioned peptides. Here, "the substantially same amino acid sequence" means the amino acid sequence qualitatively identical in the activity of the peptide (e.g. the inhibitory activity on the interaction of a ligand and a receptor) or the anti-cancer activity of the peptide (e.g. migration inhibitory activity, invasion inhibitory activity and anti-metastasis activity) or the anti-rheumatoid arthritis activity (e.g. migration inhibitory activity) or the like. Accordingly, quantitative variances are acceptable to some extent (e.g. about 0.01 to 100 times, preferably 0.5 to 20 times, or more preferably 0.5 to 2 times). Therefore, one or more of the amino acids in the amino acid sequences indicated in any of the above-mentioned formula (Ia) to (Ij) and (1) to (58) can have variances, so far as they have any of the above-mentioned properties. That is to say, in the present invention, any peptide (variant peptide) resulting from the variance in the amino acid sequence such as substitution, deletion or insertion (addition) etc. which brings about any serious (significant) change (i.e. a qualitatively different change, or a qualitatively identical but quantitatively significantly different change) in the physiological property or chemical property of the original (non-variant) peptide is deemed as substantially same as the original (non-variant) peptide having no such variance, and, the amino acid sequence of such variant peptide is deemed as substantially same as the amino acid sequence of the original (non-variant) peptide.

It is a well-known fact that generally, the change such as substitution, deletion or insertion (addition) of an amino acid in a peptide sequence often does not make a great (notable) change to physiological property or chemical property of such peptide. Such substitution is exemplified by the substitution of a certain amino acid by another amino acid of similar nature (property), and generally, it is considered that if the substitution is made between amino acids having greater similarity in their properties, so much smaller the changes caused by such substitution is in the properties of pre-substituted peptides.

Amino acids are classified, using the similarity of their properties as to one of the criteria, into the following classes, for example: (i) nonpolar (hydrophobic) amino acids (examples: alanine, leucine, isoleucine, valine, proline, phenylalanine, tryptophan, methionine, etc.); (ii) polar (neutral) amino acids (examples: glycine, serine, threonine, cysteine, tyrosine, asparagine, glutamine, etc.); (iii) (basic) amino acids carrying positive electric charge (examples: arginine, lysine, histidine, etc.); (iv)) (acidic) amino acids carrying negative electric charge (examples: asparatic acid, glutamic acid, etc.), and accordingly, amino acid substitution within each class can be conservative with regard to the property of a peptide (namely, substitution generating "substantially same" amino acid sequences).

In other words, "substantially same amino acid sequences" may include:

(i) amino acid sequences wherein 1 or more, preferably 1 to 10, more preferably 1 to 5 amino acids were substituted by other amino acids in the amino acid sequences indicated in the above-mentioned formula (Ia) to (Ij) and (1) to (58);

(ii) amino acid sequences wherein 1 to 7, preferably 1 to 5, more preferably 1 to 3 amino acids were deleted in the amino acid sequences indicated in the above-mentioned formula (Ia) to (Ij) and (1) to (58);

(iii) amino acid sequences wherein 1 to 15, preferably 1 to 10, more preferably 1 to 5 amino acids were added (inserted) in the amino acid sequences indicated in the above-mentioned formula (Ia) to (Ij) and (1) to (58); or (iv) peptides including modifications to constitutive amino acids (particularly, the side chains thereof) among the peptides having the amino acid sequences indicated in above (i), (ii) or (iii), or esters thereof or salts thereof.

A peptide of the present invention, if and when the substitution, deletion, insertion (addition), modification, etc. of above (i) to (iv) is intentionally or incidentally provided in the amino acid sequence thereof, can be varied to a stable peptide against heat or protease or a high-activity peptide having more enhanced inhibitory activity. The peptides of the present invention include also these variant peptides or amides thereof, esters thereof or salts thereof.

Furthermore, among the peptides of the present invention are the peptide consisting of the amino acid sequence indicated in any of the above-mentioned formula (Ia to Ij) and (1) to (58), and the peptide containing the amino acid sequence sharing the homology of about 50 to 99.9% (preferably, 70 to 99.9%, more preferably 90 to 99.9%) with the foregoing amino acid sequence and having the activities of substantially same nature as the peptide consisting of the amino acid sequence indicated in any of the above-mentioned formula (Ia to Ij) and (1) to (58), or amides thereof, esters thereof or salts thereof. Such activities include, for example, inhibitory activities of the peptides such as an inhibitory activity on the binding of a ligand to its receptor, a signaling inhibitory activity. The inhibitory activities of "substantially same nature" mean that the properties such as the inhibitory activity on the ligand binding to the receptor are of the same nature. Therefore, it is acceptable even if non-significant effectiveness levels of the inhibitory activity on the ligand binding to the receptor are found, and it is not matter even if there are differences in molecular weights.

The amides, esters or salts of the peptide having the amino acid sequence indicated in any of the above-mentioned formula (1) to (58) include the same ones as are exemplified for the peptide indicated in the above-mentioned formula (Ia). Preferably, the peptide having the amino acid sequence indicated in any of the above-mentioned formula (1) to (58) is better if the carboxyl group of the C-terminal amino acid residue is amidated.

The peptides of the present invention including the peptide containing the amino acid sequence indicated in any of the above-mentioned formula (1) to (58) can be produced by conventionally known methods of synthesizing peptides. For the syntheses of peptides, either solid phase peptide synthesis or liquid phase synthesis may be utilized. Namely, an expected peptide can be produced by condensing a partial peptide able to constitute a peptide or an amino acid with remaining portions, and if the product has a protecting group, by eliminating the protecting group. As the known condensation methods and elimination of protecting groups, the following examples (1) to (5) are included:
(1) M. Bodanszky and M. A. Ondetti, Peptide Synthesis, Interscience Publishers, New York (1966).
(2) Schroeder and Luebke, The Peptide, Academic Press, New York (1965).
(3) N. Izumiya, et. al., Peptide Synthesis, Basics and Practice, Maruzen, Tokyo (1975).
(4) H. Yajima and S. Sakakibara, Seikagaku-Jikken-Koza I, Protein Chemistry IV, Tokyo Kagakudojin, Tokyo, pp 205 (1977).
(5) H. Yajima, Zoku-Iyakuhin-no-Kaihatsu, Vol. 14, Peptide Synthesis, Hirokawa Publishing Co., Tokyo (1991).

As practical methods for syntheses of peptides, the following examples can be given: Generally, commercially available resins for synthesis of polypeptides can be used. Such resins include, for example, chloromethyl resin, hydroxymethyl resin, benzhydroxylamine resin, aminomethyl resin, 4-hydroxybenzylalcohol resin, 4-methylbenzhydroxylamine resin, PAM resin, 4-hydroxymethylmethylphenylacetoamidomethyl resin, polyacrylamide resin, 4-(2',4'-dimetoxyphenyl-hydroxymethyl)phenoxy resin, 4-2',4'-dimetoxyphenyl-Fmoc aminoethylphenoxy resin, etc. Using such resin, an amino acid with suitably protected α-amino group and side chain functional group is condensed on the resin to the sequence of the expected polypeptide in accordance with conventionally known condensation methods. In the last stage of the reaction, the polypeptide is cleared from the resin and simultaneously various protective groups are removed, and then, by carrying out intramolecular disulfide bond-forming reaction in highly diluted solution, the expected polypeptide or amide thereof is obtained. For the above-mentioned condensation of the protected amino acid, various activated reagents usable for the syntheses of polypeptides can be used, but, it is particularly better to use carboxyimides. Among such carboxyimides are DCC, N,N'-diisopropylcarbodiimide, N-ethyl-N'-(3-dimethylaminopropyl)cabodiimde, etc. For the activation by these, together with racemization inhibitory additives (for example, HOBt, HOOBt), a protected amino acid is added directly to the resin, or after activating the protected amino acid as symmetric acid anhydride or HOBt ester or HOOBt ester, it can be added to ester resin.

Solvents used for the activation of protected amino acids and the condensation with resins can be chosen from among the solvents known to be usable for polypeptide condensation reactions. For example, acid amides such as N,N-dimethylformamide, N,N-dimethylacetoamide and N-methylpyrrolidone, halogenated hydrocarbons such as methylene chloride and chloroform, alcohols such as trifluoroethanol, sulfoxides such as methyl sulfoxide, ethers such as pyridine, dioxane and tetrahydrofuran, nitriles such as acetonitrile and propionitrile, esters such as methyl acetate and ethyl acetate, or appropriated mixtures of the foregoings are used. A solvent used for activation of a protected amino acid or its condensation with resin can be selected from among the solvents known to be usable for condensing reactions of polypeptides. The reaction temperature is appropriately set within the scope known to be applicable to polypeptide bond forming reactions, usually, at −20° C. to 50° C. Activated amino acid derivatives are usually used at 1.5 to 4 times excess. According to the result of tests adopting ninhydrin reaction, if the condensation is insufficient, the repetition of condensation reactions without eliminating protective groups can lead to sufficient condensation. If sufficient condensation is attained by the repetition of reactions, unreacted amino acids can be acetylated by the use of acetic anhydride or acetylimidazole.

The protective group of the amino group used as ingredients include, for example, Z, Boc, tertialypentyloxycarbony, isobornyloxycarbonyl, 4-methoxybenzyloxycabonyl, Cl-Z, Br-Z, adamantyloxycabonyl, trifluoroacetyl, phtaloyl, formyl, 2-nitrophenylsulphenyl, diphenylphosphinothioyl, Fmoc, etc. Carboxyl group can be protected, for example, by alkyl esterification (e.g. straight-chain, branching or circular alkyl esterification of methyl, ethyl, propyl, butyl, tertialbutyl, cyclopentyl, cyclohexyl, cycloheptyl, cyclooctyl, 2-adamantyl, etc.), aralkyl esterification (e.g. benzylester, 4-nitrobenzylester, 4-methoxybenzylester, 4-chlorbenzylester, benzhydryl esterification), phenacylesterification, benzylcarbonylhydrazidation, tertialybutoxycarbonylhydrazidation, tritylhydrazidation, etc. The hydroxyl group of serine can be protected, for example, by esterification or etherification. The groups suitable for this eterification include, for example, groups derivatized from carboxylic acid such as lower alkanoyl group such as acetyl group, aroyl group such as benzoyl group, benzyloxycarbonyl group, ethoxycarbonyl group. The groups suitable for etherification include, for example, benzyl group, tetrahydropiranyl group, tertiarybutyl group, etc. As the protective groups of phenolic OH group of tyrosine, for example, Bzl, C12-Bzl, 2-nitrobenzyl, Br-Z, tertiarlybutyl, etc. are used. As the protective groups of imidazole of histidine, for example, Tos, 4-methoxy-2,3,6-trimethylbenzenesulfonyl, DNP, benzyloxymethyl, Bum, Boc, Trt, Fmoc etc. are used.

Ingredients with activated carboxyl groups include, for example, corresponding acid anhydride, azide, active ester [ester of alcohol (e.g. pentachlorophenol, 2,4,5-trichlorophenol, 2,4-dinitrophenol, cyanomethylalcohol, p-nitrophenol, HONB, N-hydroxysuccimide, N-hydroxyphtalimide, HOBt)] are used. Ingredients with activated amino group include, for example, corresponding phosphoric amide. As the methods to remove (elimiate) protective groups, for example, catalytic reduction in hydrogen airstream in the presence of a catalyst such as Pd-black or Pd-carbon, acid treatment by anhydrous hydrogen fluoride, methanesulfonic acid, trifluoromethanesulfonic acid, trifluoroacetic acid or a mixture thereof, etc, base treatment by diisopropylethylamine, triethylamine, piperidine, piperadine, etc., and reduction by natrium in liquid ammonia are used. Elimination reaction by the above-mentioned acid treatment is done generally at the temperature of about −20° C. to 40° C., but in the acid treatment, it is effective to add a cation trapping agent such as anisole, phenol, thioanisole, m-cresol, p-cresol, dimethylsulfide, 1,4-butanedithiol, 1,2-ethanedithiol. 2,4-dinitrophenyl group used as the protective group of imidazole of histidine is removed by thiophenol treatment. Formyl group used as the protective group of indole of tryptophan is removed by elimination of protection by the above-mentioned acid treatment in the presence of 1,2-ethanedithiol, 1,4-butanedithiol, etc. and also is removed by alkaline treatment by dilute sodium hydroxide solution, dilute ammonia, etc.

Protection and protective group of functional groups not to be involved in the reaction of ingredients, and elimination of such protective group, and activation of functional groups to be involved in the reaction, etc. can be appropriately selected from among conventionally known groups or conventionally known measures. As alternative methods to obtain amides of polypeptides, there is, for example, a method to manufacture, after amidating and protecting α-carboxyl group of carboxy-terminal amino acid and then extending the peptide chain to the desired chain length on the side of amino group, a polypeptide eliminating the protective group of α-amino group of N-terminal of such peptide chain and a polypeptide eliminating the protective group of carboxyl group of C-terminal, and then these two peptides are condensed in the above-mentioned mixed solvent. The details of the condensation reaction are the same as described above. After purifying the protected polypeptide obtained by the condensation, the desired raw polypeptide can be obtained by eliminating all the protective groups by the above-mentioned method. Having purified this raw polypeptide using various known purification methods, if the main fraction is freeze-dried, an amide type of the desired polypeptide can be obtained. To get an ester type of the polypeptide, for example, make an amino acid ester by condensing α-carboxyl group of carboxy-terminal amino acid with the desired alcohols, and then, the ester type of the desired polypeptide can be obtained in the same way as the amide type of the polypeptide.

After the reaction, the peptides of the present invention can be purified and isolated by combining usual purification methods such as solvent extraction, distillation, column chromatography, liquid chromatography, re-crystallization, etc. If a peptide obtained by the above-mentioned methods is a salt-free type, it can be converted to a suitable salt by known methods, or if such peptide is a salt, it can be converted to a salt-free type by known methods.

Preferably, the new peptides of the present invention having the amino acid sequences indicated in the above-mentioned formula (1) to (58) can be manufactured by the methods described in the below-mentioned practical examples or similar methods. Also, the peptides of the present invention can be manufactured by the methods described in the International Publication No. 02/20561 Pamphlet or similar methods.

In the event that the peptides of the present invention are used as human drugs or veterinary drugs, usual usages may be applied. For example, according to need, they may be used by the oral route in the forms of sugar-coated tablets, capsules, elixirs, micro-capsulated formulations, etc. or by the parenteral route in the injectable forms of sterile solutions made of water or other pharmacologically acceptable liquid, suspensions, etc. For example, the peptides of the present invention can be manufactured as drugs by incorporating physiologically acceptable carriers, flavoring compound, excipients, vehicles, preservatives, stabilizers, binding agents in the unit dosage formulation forms required for the generally accepted pharmaceutical manufacturing. The quantity of any active ingredient in such drugs should be the optimal amount within the instructed scope.

Additives which can be incorporated into tablets, capsules, etc. include, for example, binding agents such as gelatin, cornstarch, tragacanth gum and gum Arabic, diluting agents such as crystalline cellulose, swelling agents such as cornstarch, gelatin and alginic acid, lubricant agents such as magnesium stearate, sweetening agents such as sucrose, lactose or saccharine, and flavoring agents such as peppermint, akamono oil or cherry. If the preparation form is capsules, it can contain a liquid carrier such as oil in addition to the above-mentioned materials. Sterile composition for injection can be formulated in accordance with usual pharmaceutical manufacturing practices, by dissolving or suspending active ingredients or natural vegetable oils such as sesame oil and copra oil in the vehicles such as injection solvents.

As watery solutions for injections, for example, isotonic solutions containing physiological saline, glucose and other adjunctive agents (e.g., D-sorbitol, D-mannitol, sodium chloride, etc.) can be used, and also can be used together with a suitable solubilizing agent such as alcohol (e.g., ethanol), polyalcohol (e.g., propylene glycohol, polyethylene glycohol), nonionic surfactant (e.g., Polysorbate 80™, (HCO-50) etc. Oily solutions include sesame oil, soybean oil, etc. and can be used together with solubilizing agents such as benzyl benzoate and benzylalcohol. They can also be combined with a buffering agent (e.g., phosphate buffer solution, sodium acetate buffer solution), a soothing agent (e.g., benzalkonium chloride, procaine hydrochloride, etc.), a stabilizer (e.g., human serum albumine, polyethylene glycohol, etc.), a preservative (e.g., benzylalcohol, phenol, etc.), an antioxidant, etc. A prepared injection is sterilely filled into an ampoule.

The pharmaceutical preparations manufactured as above are safe and low-toxic, and accordingly, can be administered to, for example, humans and mammals (e.g., mice, rats, guinea pigs, rabbits, sheep, swines, cows, cats, dogs, monkeys, hamadryas, chimpanzees, etc.).

The dose of a peptide of the present invention differs depending on the disease condition, etc. The dose in oral administration is usually about 0.1 to 1000 mg per one time per 60 kg of the body weight, preferably about 1.0 to 500 mg, and more preferably about 1.0 to 200 mg. The single dose in parenteral administration per 60 kg of the body weight differs depending on the administration subject, disease condition, administration method, etc.; for example, in case of injection, usually about 0.01 to 300 mg, preferably about 0.1 to 200 mg, and more preferably about 0.1 to 100 mg per one time may be administered intravenously. For other animals, the dose based on 60 kg of the body weight can be administered.

The peptides of the present invention have an anti-cancer activity, i.e. an activity for inhibiting movement of cancer cells and a cancer metastasis inhibitory activity. That is to say, the peptides of the present invention, as clearly seen in the below-mentioned practical examples, can be used as drugs for prevention and therapy of cancers, especially cancer metastasis, since they have a cancer metastasis inhibitory activity. Accordingly, the peptides of the present invention as anti-cancer drugs are useful for the amelioration, prevention and therapy of oral cancer, throat cancer, lip cancer, lingual cancer, gingival cancer, nasopharyngeal cancer, esophageal cancer, gastric cancer, small intestinal cancer, large intestinal cancer including colorectal cancer, liver cancer, gallbladder cancer, pancreatic cancer, nasal cancer, lung cancer, bone cancer, soft tissue cancer, skin cancer, melanoma, breast cancer, uterine cancer, ovarian cancer, prostate cancer, testicular cancer, penile cancer, bladder cancer, kidney cancer, brain cancer, thyroid cancer, lymphoma, leukemia, etc. Also, the peptides of the present invention have an anti-chronic rheumatoid arthritis activity, i.e., an inhibitory effect on T-cell movement. In other words, the peptides of the present invention, as clearly seen in the below-mentioned practical examples, can be used as drugs for the prevention and therapy of chronic rheumatoid arthritis, since they have an inhibitory action on T-cell movement. Thus, the peptides of the present invention are useful as drugs for the amelioration, prevention and therapy of chronic rheumatoid arthritis.

It is well-known that CXCR4 antagonistic compounds have an anti-viral activity. Accordingly, it would be obvious to the concerned industry that the peptides of the present invention can be used as preventive and therapeutic drugs for viral infectious disease (e.g. AIDS, SARS, etc.).

The use of the peptides of the present invention as anti-cancer drugs can be made concomitantly with other anti-cancer drugs (for example, chemotherapeutic drugs, immunotherapeutic drugs, or drugs inhibiting the activity of cell growth factors and their receptors) etc. (hereafter referred to as "concomitant drugs").

A peptide of the present invention exhibits a beneficial anti-cancer activity when used in a single preparation form, but, the activity can be further enhanced when used together with one or more of the above-mentioned concomitant drugs (concomitant use of multiple drugs).

As the said "chemotherapeutic drugs", alkylating drugs, antimetabolites, anticancer antibiotics and plant-derived anticancer drugs can be exemplified.

Included in the examples of "alkylating drugs" are nitrogen mustard, nitrogen mustard-N-oxide hydrochloride, chlorambutyl, cyclophosphamide, ifosfamide, thiotepa, carboquone, improsulfan tosylte, busulfan, nimustine hydrochloride, mitobronitol, melphalan, dacarbazine, ranimustine, estramustine sodium phosphate, triethylenmelamine, carmustine, lomustine, streptozocin, pipobroman, etoglucide, altretamine, ambamustin, dibrospidium hydrochloride, fotemustin, prednimustin, pumitepa, ribomustin, temozolomide, treosulphan, trophosphamide, zinostatin stimalamer, carboquone, adzelecin, systemstin, bizelesin, platinum complex (carboplatin, cisplatin, miboplatin, nedaplatin, oxaliplatin, etc.).

"Antimetabolites" include, for example, mercaptopurine, 6-mercaptopurine riboside, thioinosine, methotrexate, enocitabine, cytarabine, cytarabine ocfosfate, ancitabine hydrochloride, 5-FU agents (e.g. fluorouracil, tegafur, UFT, doxifluridine, carmofur, galocitabine, emitefur, etc.), aminopterin, calcium leucovorin, tabloid, butocin, calcium folinate, calcium levofolinate, cladribine, emitefur, fludarabine, gemcitabine, hydroxycarbamide, pentostatin, piritrexim, idoxuridine, mitoguzaon, thiazofurin, ambamustin and gemicitabine.

"Anticancer antibiotics" include, for example, antracycline anti-cancer agents (doxorubicine hydrochloride, daunorubicin hydrochloride, aclarubicin hydrochloride, pirarubicin hydrochloride, epirubicin hydrochloride, etc.), actinomycin D, actinomycin C, mitomycin C, chromomycin A3, bleomycin hydrochloride, bleomycin sulfate, pleomycin sulfate, neocarzinostatin, mithramycin, sarcomycin, carzinophilin, mitotane, zorbicin hydrochloride, mitoxantrone hydrochloride and idarubicin hydrochloride.

"Plant-derived anti-cancer agents" include, for example, vinca alkaloid anti-cancer agents (vinblastine sulfate, vincristine sulfate, vindesin sulfate, vinorelbine, etc.), taxan anti-cancer agents (paclitaxel, docetaxel, etc.), etoposide, etoposide phosphate, teniposide and vinorelbine.

The "cell growth factors" in the said "drugs inhibiting the activity of cell growth factors and their receptors" can be any material that promotes the growth of cells, and include a factor exhibiting its activity at low concentration by the interaction with its receptor in the peptide of less than 20,000 molecular weight. Specifically, they include (1) EGF (epidermal growth factor) or a material having substantially the same activity as EGF (e.g., EGF, HER2 ligand, etc.), (2) insulin or a material having substantially the same activity as insulin [e.g., insulin, IGF (insulin-like growth factor)-1, IGF-2, etc.], (3) FGF (fibroblast growth factor) a material having substantially the same activity as FGF [e.g., acidic FGF, basic FGF, KGF (keratinocyte growth factor), FGF-10, etc.], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factorβ), HGF (hepatocyte growth factor), VEGF (vascular endothelial growth factor), etc.].

The said "receptors of cell growth factors can be any receptor that has binding capacity with the above-mentioned cell growth factors. Specifically, they include EGF receptor, HER2, insulin receptor, IGF receptor, FGF receptor-1 or FGF receptor-2, HGF receptor (c-met), VEG receptor, SCF receptor (c-kit).

The said "drugs inhibiting the activity of cell growth factors" include Herceptin (HER2 anti-body), GLEEVEC (c-met, c-kit, ab1 inhibitor), Iressa (EGF receptor inhibitor) etc.

Besides the above-mentioned drugs, topoisomerase I inhibitor (e.g., irinotecan, topotecan, etc.), topoisomerase II inhibitor (e.g., sobuzoxane, etc.), angiogenesis inhibitor, etc. can be used.

In the case of use of a peptide of the present invention as a preventive and/or therapeutic drug, it may be used concomitantly with other preventive and/or therapeutic drug(s) for rheumatoid arthritis. Drugs of such concomitant use include, for example, anti-inflammatory steroids (e.g., prednisolone, hydrocortisone, methyl-prednisolone, dexamethasone, betamethasone, etc.), nonsteroidal anti-inflammatory and analgesic drugs (e.g., indometacin, diclofenac, loxoprofen, ibuprofen, aspirin, piroxicam, sulindac, etc.) or hyaluronic acid formulations (e.g., sodium hyaluronate, etc.), COX-II inhibitors, etc.

The peptides of the present invention exhibit an effective anti-chronic rheumatoid arthritis activity in the single preparation form, but the effect can be further enhanced by the concomitant use (multi-drug use) together with one or more of the above-mentioned concomitant drugs.

In the concomitant use of the peptides of the present invention and concomitant drugs, the administration time of the peptides of the present invention and a concomitant drug is not limited, and a peptide of the present invention and a concomitant drug can be administered to the subject at the same time or at different times. The dose of a concomitant drug can follow the usual dose clinically adopted, and can be determined appropriately depending on the administration subject, administration route, disease conditions, combination, etc.

The administration mode of a peptide of the present invention and a concomitant drug is not particularly limited, and it is acceptable if a polypeptide of the present invention or a salt thereof and a concomitant drug are combined at the time of administration. Such administration mode may be, for example, (1) the administration of a single preparation formulated by the simultaneous combination of a peptide of the present invention and a concomitant drug, (2) the simultaneous administration by the same administration route of two different drugs—one being a drug formulated using a peptide of the present invention and the other being a concomitant drug, (3) the administration by the same route at different times of two different drugs—one being a drug formulated using a peptide of the present invention and the other being a concomitant drug, (4) the simultaneous administration by different routes of two different drugs—one being a drug formulated using a peptide of the present invention and the other being a concomitant drug, (5) the administration by different routes at different times of two different drugs—one being a drug formulated using a peptide of the present invention and the other being a concomitant drug (for example, the administration of a peptide of the present invention followed by a concomitant drug, or vice versa), etc. These administration modes are hereafter collectively referred to as "concomitant drug(s) of the present invention".

Any concomitant drug of the present invention has low toxicity, and accordingly, can be safely administered orally or parenterally (e.g., local, rectum, vein, etc.) in the form of pharmaceutical compositions prepared by mixing a peptide of the present invention and/or the above-mentioned concomitant drug with a pharmacologically acceptable carrier in accordance with a method known in the art. Such pharmaceutical compositions include, without limitation, tablets (including sugar-coated tablets and film-coated tablets), powders, granules, capsules (including soft capsules), solutions, injections, suppositories, sustained-release formulations, etc. An injection can be administered to the interior or proximal site of a tumor or directly to the lesion by intraveneous, intramuscular, subcutaneous, intraorgan, intranasal, intradermal, eye dropping, intracerebral, intrarectal, intravaginal or intraperitoneal administration.

Pharmacogically acceptable carriers identical to those used for the above-mentioned pharmaceutical compositions of the present invention can be used in the manufacturing of the concomitant drugs of the present invention.

The combination ratio of any of the peptides of the present invention and a concomitant drug belonging to the concomitant drugs of the present invention can be determined appropriately depending on the subject to be administered, routes for administration, disease conditions, etc.

The content of a concomitant drug belonging to the concomitant drugs of the present invention varies depending on the drug preparation forms. It is usually about 0.01 to 100% by weight in the whole preparation, or preferably about 0.1 to 50% by weight, or most preferably about 0.5 to 20% by weight.

The content of an additive such as a carrier in the concomitant drugs of the present invention varies depending on the drug preparation forms. It is usually about 1 to 99.9% by weight in the whole preparation, or preferably about 10 to 90% by weight.

The present invention is described in further details by the following practical examples, which, however, will not limit the range of the present invention.

MANUFACTURING EXAMPLE 1

Manufacturing of Polypeptide TC14003

H-Arg-Arg-Nal-Cys-Tyr-Cit-Lys-DLys-Pro-Tyr-Arg-Cit-Cys-Arg-OH (TC14003)

1. Synthesis of TC14003 Protected Polypeptide Resin:

After removing Fmoc group from Alko resin attached with the first arginine of the 14-position (Fmoc-Arg(Pbf)-Alko-resin) by 20% piperidine/DMF, Fmoc-Cys(Trt)-OH (2.5 eq) of the 13-position was added, and condensation reaction by DIPCDI-HOBt method was conducted in DMF. The progress of the condensation reaction was monitered by ninhydrin test of Kaiser, E. et al. (Anal. Biochem., 34: 595 (1970)).

2. Introduction of Amino Acids of the 12-Position to 1-Position:

Similarly to the foregoing, Cit, Arg(Pbf), Tyr(t-Bu), Pro, DLys(Boc), Lys(Boc), Cit, Tyr(t-Bu), Cys(Trt), Nal, Arg(Pbf), Arg(Pbf) residues were sequentially introduced into the resin to yield the protected polypeptide resin.

3. Deprotection and Clearage of Polypeptide from the Resin and Purification:

After removing Fmoc group from the protected polypeptide resin by 20% piperidine/DMF treatment, the resulting polypeptide resin was treated by 1 M TMSBr-thioanisole/TFA(trifluoroacetic acid) mixture (in the presence of m-cresol (100 eq), ethanedithiol (300 eq)) at 25° C. for 2 hours. The resin was separated by filtration from the reaction mixture, washed with TFA twice, the mixture of the filtrate and wash solution was subjected to concentration in vacuo, the remaining residue was added with water-cooled dry ether, the resultant precipitation was separated from supernatant liquid by centrifugal sedimentation and decantation. The obtained residue was washed with cold ether, dissolved into 1 N acetic acid, and diluted by distilled water.

4. Cyclization by Air Oxidation:

Diluted water solution of the above-mentioned polypeptide was adjusted to pH7.5 by concentrated ammonia water, and was cyclized by ventilated air oxidation. This water solution was purified by preparative HPLC (COSMOSIL 5C18 AR-II column: acetonitrile-water) and gel filtration chromatography (Sephadex G-15, eluate: 0.1 N AcOH), a polypeptide of a single peak was obtained and freeze-dried. The purity was confirmed by HPLC.

MANUFACTURING EXAMPLE 2

Manufacturing of TC14005

H-Arg-Arg-Nal-Cys-Tyr-Arg-Lys-DCit-Pro-Tyr-Arg-Cit-Cys-Arg-OH (TC14005)

TC14005 was manufactured by the same method as Manufacturing Example 1. However, DCit replaced DLys(Boc) of the 8-position and Arg(Pbf) replaced Cit of the 6-position respectively during the introduction of the amino acids from the 12-postion through the 1-position.

MANUFACTURING EXAMPLE 3

Manufacturing of TC14011

H-Arg-Arg-Nal-Cys-Tyr-Cit-Lys-DCit-Pro-Tyr-Arg-Cit-Cys-Arg-OH (TC14011)

TC14011 was manufactured by the same method as Manufacturing Example 1. However, DCit replaced Dlys(Boc) of the 8-position during the introduction of the amino acids from the 12-postion through the 1-position.

MANUFACTURING EXAMPLE 4

Manufacturing of TC14013

H-Arg-Arg-Nal-Cys-Tyr-Cit-Lys-DLys-Pro-Tyr-Cit-Cit-Cys-Arg-OH (TC14013)

TC14013 was manufactured by the same method as Manufacturing Example 1. However, Cit replaced Arg(Pbf) of the 11-position during the introduction of the amino acids from the 12-postion through the 1-position.

MANUFACTURING EXAMPLE 5

Manufacturing of TC14015

H-Cit-Arg-Nal-Cys-Tyr-Cit-Lys-DLys-Pro-Tyr-Arg-Cit-Cys-Arg-OH (TC14015)

TC14015 was manufactured by the same method as Manufacturing Example 1. However, Cit replaced Arg(Pbf) of the 1-position during the introduction of the amino acids from the 12-postion through the 1-position.

MANUFACTURING EXAMPLE 6

Manufacturing of TC14017

H-Cit-Arg-Nal-Cys-Tyr-Arg-Lys-DCit-Pro-Tyr-Arg-Cit-Cys-Arg-OH (TC14017)

TC14017 was manufactured by the same method as Manufacturing Example 1. However, DCit replaced DLys(Boc) of the 8-position, Arg(Pbf) replaced Cit of the 6-position and Cit replaced Arg(Pbf) of the 1-position respectively during the introduction of the amino acids from the 12-postion through the 1-position.

MANUFACTURING EXAMPLE 7

Manufacturing of TC14019

H-Arg-Arg-Nal-Cys-Tyr-Arg-Lys-DCit-Pro-Tyr-Cit-Cit-Cys-Arg-OH (TC14019)

TC14019 was manufactured by the same method as Manufacturing Example 1. However, Cit replaced Arg(Pbf) of the 11-position, DCit replaced DLys(Boc) of the 8-position, and Arg(Pbf) replaced Cit of the 6-position during the introduction of the amino acids from the 12-postion through the 1-position.

MANUFACTURING EXAMPLE 8

Manufacturing of TC14021

H-Cit-Arg-Nal-Cys-Tyr-Arg-Lys-DLys-Pro-Tyr-Cit-Cit-Cys-Arg-OH (TC14021)

TC14021 was manufactured by the same method as Manufacturing Example 1. However, Cit replaced Arg(Pbf) of the 11-position, Arg(Pbf) replaced Cit of the 6-position and Cit replaced Arg(Pbf) of the 1-position respectively during introduction of the amino acids from the 12-postion through the 1-position.

MANUFACTURING EXAMPLE 9

Manufacturing of TC14012

H-Arg-Arg-Nal-Cys-Tyr-Cit-Lys-DCit-Pro-Tyr-Arg-Cit-Cys-Arg-NH$_2$ (TC14012)

1. Synthesis of TC14012 Protected Polypeptide Resin:

After removing Fmoc group from Fmoc-Rink amide resin by 20% piperidine/DMF, Fmoc-Arg(Pbf)-OH (2.5 eq) corresponding to the 14-position was added, and condensation reaction by DIPCDI-HOBt method was conducted in DMF. The progress of the condensation reaction was monitored by ninhydrin test of Kaiser, E. et al. (Anal. Biochem., 34: 595 (1970)).

2. Introduction of Amino Acids of the 13-Position to 1 Position:

Similarly to the foregoing, Cys(Trt), Cit, Arg(Pbf), Tyr(t-Bu), Pro, DCit, Lys(Boc), Cit, Tyr(t-Bu), Cys(Trt), Nal, Arg(Pbf), Arg(Pbf) residues were sequentially introduced into the Rink amide resin, and the protected polypeptide resin was obtained.

3. Deprotection and Clearage of Polypeptide from the Resin and Purification:

After removing Fmoc group from the protected polypeptide resin by 20% piperidine/DMF treatment, the resulting polypeptide resin was treated by 1 M TMSBr-thioanisole/TFA(trifluoroacetic acid) mixture (in the presence of m-cresol (100 eq), ethanedithiol (300 eq)) at 25° C. for 3 hours. The resin was separated by filtration from the reaction mixture, washed by TFA twice, the mixture of the filtrate and the wash solution was subjected to concentration in vacuo, the remaining residue was added with water-cooled dry ether, the resulting precipitation was separated from supernatant liquid by centrifugal sedimentation and decantation. The obtained residue was washed with cold ether, dissolved into 1 N acetic acid, and diluted by distilled water.

4. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC (COSMOSIL 5C18 AR-II column: acetonitrile-water) and gel filtration chromatography (Sephadex G-15, eluate: 0.1 N AcOH), a polypeptide of a single peak was obtained and freeze-dried. The purity was confirmed by HPLC.

MANUFACTURING EXAMPLE 10

Manufacturing of TC14014

H-Arg-Arg-Nal-Cys-Tyr-Cit-Lys-DLys-Pro-Tyr-Cit-Cit-Cys-Arg-NH$_2$ (TC14014)

TC14014 was manufactured by the same method as Manufacturing Example 9. However, Cit replaced Arg(Pbf) of the 11-position and DLys(Boc) replaced DCit of the 8-position respectively during the introduction of the amino acids from the 13-postion through the 1-position.

MANUFACTURING EXAMPLE 11

Manufacturing of TC14016

H-Cit-Arg-Nal-Cys-Tyr-Cit-Lys-DLys-Pro-Tyr-Arg-Cit-Cys-Arg-NH$_2$ (TC14016)

TC14016 was manufactured by the same method as Manufacturing Example 9. However, Dlys(Boc) replaced DCit of the 8-position and Cit replaced Arg(Pbf) of the 1-position respectively during the introduction of the amino acids from the 13-postion through the 1-position.

MANUFACTURING EXAMPLE 12

Manufacturing of TC14018

H-Cit-Arg-Nal-Cys-Tyr-Arg-Lys-DCit-Pro-Tyr-Arg-Cit-Cys-Arg-NH$_2$ (TC14018)

TC14018 was manufactured by the same method as Manufacturing Example 9. However, Arg(Pbf) replaced Cit of the 6-position and Cit replaced Arg(Pbf) of the 1-position respectively during the introduction of the amino acids from the 13-postion through the 1-position.

MANUFACTURING EXAMPLE 13

Manufacturing of TC14020

H-Arg-Arg-Nal-Cys-Tyr-Arg-Lys-DCit-Pro-Tyr-Cit-Cit-Cys-Arg-NH$_2$ (TC14020)

TC14020 was manufactured by the same method as Manufacturing Example 9. However, Cit replaced Arg(Pbf) of the 11-position and Arg(Pbf) replaced Cit of the 6-position respectively during the introduction of the amino acids from the 13-postion through the 1-position.

MANUFACTURING EXAMPLE 14

Manufacturing of TC14022

H-Cit-Arg-Nal-Cys-Tyr-Arg-Lys-DLys-Pro-Tyr-Cit-Cit-Cys-Arg-NH$_2$ (TC14022)

TC14022 was manufactured by the same method as Manufacturing Example 9. However, Cit replaced Arg(Pbf) of the 11-position, DLys(Boc) replaced DCit of the 8-position, Arg(Pbf) replaced Cit of the 6-position and Cit replaced Arg(Pbf) of the 1-position respectively during the introduction of the amino acids from the 13-postion through the 1-position.

MANUFACTURING EXAMPLE 15

Manufacturing of TA14001, TA14005-TA14009, TC14001 and TC14004

H-Ala-Arg-Nal-Cys-Tyr-Arg-Lys-DLys-Pro-Tyr-Arg-Cit-Cys-Arg-OH (TA14001)

H-Arg-Arg-Nal-Cys-Tyr-Ala-Lys-DLys-Pro-Tyr-Arg-Cit-Cys-Arg-OH (TA14005)

H-Arg-Arg-Nal-Cys-Tyr-Arg-Ala-DLys-Pro-Tyr-Arg-Cit-Cys-Arg-OH (TA14006)

H-Arg-Arg-Nal-Cys-Tyr-Arg-Lys-DAla-Pro-Tyr-Arg-Cit-Cys-Arg-OH (TA14007)

H-Arg-Arg-Nal-Cys-Tyr-Arg-Lys-DLys-Ala-Tyr-Arg-Cit-Cys-Arg-OH (TA14008)

H-Arg-Arg-Nal-Cys-Tyr-Arg-Lys-DLys-Pro-Ala-Arg-Cit-Cys-Arg-OH (TA14009)

H-Cit-Arg-Nal-Cys-Tyr-Arg-Lys-DLys-Pro-Tyr-Arg-Cit-Cys-Arg-OH (TC14001)

H-Arg-Arg-Nal-Cys-Tyr-Arg-Cit-DLys-Pro-Tyr-Arg-Cit-Cys-Arg-NH$_2$ (TC14004)

The above-listed TA14001, TA14005-TA14009, TC14001 and TC14004 can be manufactured by the same method as Manufacturing Example 1 or 9 with replacements of amino acids.

MANUFACTURING EXAMPLE 16

Manufacturing of AcTC14003, AcTC14005, AcTC14011-AcTC14022

Ac-Arg-Arg-Nal-Cys-Tyr-Cit-Lys-DLys-Pro-Tyr-Arg-Cit-Cys-Arg-OH (AcTC14003)

Ac-Arg-Arg-Nal-Cys-Tyr-Arg-Lys-DCit-Pro-Tyr-Arg-Cit-Cys-Arg-OH (AcTC14005)

Ac-Arg-Arg-Nal-Cys-Tyr-Cit-Lys-DCit-Pro-Tyr-Arg-Cit-Cys-Arg-OH (AcTC14011)

Ac-Arg-Arg-Nal-Cys-Tyr-Cit-Lys-DLys-Pro-Tyr-Cit-Cit-Cys-Arg-OH (AcTC14013)

Ac-Cit-Arg-Nal-Cys-Tyr-Cit-Lys-DLys-Pro-Tyr-Arg-Cit-Cys-Arg-OH (AcTC14015)

Ac-Cit-Arg-Nal-Cys-Tyr-Arg-Lys-DCit-Pro-Tyr-Arg-Cit-Cys-Arg-OH (AcTC14017)

Ac-Arg-Arg-Nal-Cys-Tyr-Arg-Lys-DCit-Pro-Tyr-Cit-Cit-Cys-Arg-OH (AcTC14019)

Ac-Cit-Arg-Nal-Cys-Tyr-Arg-Lys-DLys-Pro-Tyr-Cit-Cit-Cys-Arg-OH (AcTC14021)

Ac-Arg-Arg-Nal-Cys-Tyr-Cit-Lys-DCit-Pro-Tyr-Arg-Cit-Cys-Arg-NH$_2$ (AcTC14012)

Ac-Arg-Arg-Nal-Cys-Tyr-Cit-Lys-DLys-Pro-Tyr-Cit-Cit-Cys-Arg-NH$_2$ (AcTC14014)

Ac-Cit-Arg-Nal-Cys-Tyr-Cit-Lys-DLys-Pro-Tyr-Arg-Cit-Cys-Arg-NH$_2$ (AcTC14016)

Ac-Cit-Arg-Nal-Cys-Tyr-Arg-Lys-DCit-Pro-Tyr-Arg-Cit-Cys-Arg-NH$_2$ (AcTC14018)

Ac-Arg-Arg-Nal-Cys-Tyr-Arg-Lys-DCit-Pro-Tyr-Cit-Cit-Cys-Arg-NH$_2$ (AcTC14020)

Ac-Cit-Arg-Nal-Cys-Tyr-Arg-Lys-DLys-Pro-Tyr-Cit-Cit-Cys-Arg-NH$_2$ (AcTC14022)

Acetylated TC14003, TC14005, TC14011-TC14022 were manufactured by the same method as Manufacturing Example 1 to 14. However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1M TMSBr-thioanisole/TFA(trifluoroacetic acid) mixture (in the presence of m-cresol (100 eq), ethanedithiol (300 eq)) at 25° C. for 2 hours (in case of C-terminal being carboxylic acid) or for 3 hours (in case of C-terminal being amide).

MANUFACTURING EXAMPLE 17

Manufacturing of Polypeptide TE14005

H-Arg-Arg-Nal-Cys-Tyr-Arg-Lys-DGlu-Pro-Tyr-Arg-Cit-Cys-Arg-OH (TE14005)

1. Synthesis of TE14005 Protected Polypeptide Resin:

After removing Fmoc group from Fmoc-Arg(Pbf)-Alko resin (0.74 mmol/g) 270 mg (0.2 mmol) attached with the first arginine of the 14-position by 20% piperidine/DMF, Fmoc-Cys(Trt)-OH (2.5 eq) corresponding to the 13-position was added, and condensation reaction by DIPCDI-HOBt method was conducted in DMF. The progress of the condensation reaction was monitored by ninhydrin test of Kaiser, E. et al. (Anal. Biochem., 34: 595 (1970)).

2. Introduction of Amino Acids of the 12-Position to 1 Position:

Similarly to the foregoing, Cit, Arg(Pbf), Tyr(t-Bu), Pro, DGlu(O-t-Bu), Lys(Boc), Arg(Pbf), Tyr(t-Bu), Cys(Trt), Nal, Arg(Pbf), Arg(Pbf) residue was sequentially introduced into the resin, and protected polypeptide resin was obtained.

3. Deprotection and Clearage of Polypeptide from Resin and Purification:

After removing Fmoc group from the protected polypeptide resin (200 mg) by 20% piperidine/DMF treatment, the resulting polypeptide resin was treated by 10 mL of 1 M TMSBr-thioanisole/TFA(trifluoroacetic acid) mixture (in the presence of m-cresol(100 eq), ethandithiol (300 eq)) at 25° C. for 2 hours. The resin was separated by filtration from the reaction mixture, was washed with TFA 1 mL twice, the mixture of the filtrate and the wash solution was subjected to concentration in vacuo, the remaining residue was added with 30 mL of water-cooled dry ether, the resultant sediment was separated from supernatant liquid by centrifugal sedimentation and decantation. The obtained residue was cleansed by cold ether, dissolved into 50 mL of 1 N acetic acid, and diluted to 250 mL by distilled water.

4. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC (COSMOSIL 5C18 AR-II column: acetonitrile water) and gel filtration chromatography (Sephadex G-15, eluate: 0.1 N AcOH), a polypeptide of a single peak was obtained and freeze-dried. The purity was confirmed by HPLC.

Yield: 24.1 mg (7 AcOh salt) (21.3%) [α]D23.6=−5.36 (c 1.12, H2O) Ionspray mass spectrum (IS-MS): $C_{89}H_{136}N_{32}O_{20}S_2$ Calculated Value: 2038.38 Actual Measurement Value: 2038 (triple stage quadrupole mass spectrometry API-IIIE (Sciex))

MANUFACTURING EXAMPLE 18

Manufacturing of Polypeptide TE14001

H-DGlu-Arg-Nal-Cys-Tyr-Arg-Lys-DLys-Pro-Tyr-Arg-Cit-Cys-Arg-OH (TE14001)

TE14001 was manufactured by the same method as Manufacturing Example 17. However, DLys(Boc) replaced DGlu (O-t-Bu) of the 8-position, and DGlu(O-t-Bu) replaced Arg (Pbf) of the 1-position respectively during the introduction of the amino acids from the 12-postion through the 1-position.

MANUFACTURING EXAMPLE 19

Manufacturing of Polypeptide TE14002

H-Arg-Glu-Nal-Cys-Tyr-Arg-Lys-DLys-Pro-Tyr-Arg-Cit-Cys-Arg-OH (TE14002)

TE14002 was manufactured by the same method as Manufacturing Example 17. However, DLys(Boc) replaced DGlu (O-t-Bu) of the 8-position, and Glu(O-t-Bu) replaced Arg (Pbf) of the 2-position respectively during the introduction of the amino acids from the 12-postion through the 1-position.

MANUFACTURING EXAMPLE 20

Manufacturing of Polypeptide TC14003

H-Arg-Arg-Nal-Cys-Tyr-Glu-Lys-DLys-Pro-Tyr-Arg-Cit-Cys-Arg-OH (TE14003)

TE14003 was manufactured by the same method as Manufacturing Example 17. However, DLys(Boc) replaced DGlu (O-t-Bu) of the 8-position, and DGlu(O-t-Bu) replaced Arg (Pbf) of the 6-position respectively during the introduction of the amino acids from the 12-postion through the 1-position.

MANUFACTURING EXAMPLE 21

Manufacturing of Polypeptide TE14004

H-Arg-Arg-Nal-Cys-Tyr-Arg-Glu-DLys-Pro-Tyr-Arg-Cit-Cys-Arg-OH (TE14004)

TE14004 was manufactured by the same method as Manufacturing Example 17. However, Dlys(Boc) replaced DGlu (O-t-Bu) of the 8-position, and DGlu(O-t-Bu) replaced Lys (Boc) of the 7-position respectively during the introduction of the amino acids from the 12-postion through the 1-position.

MANUFACTURING EXAMPLE 22

Manufacturing of Polypeptide TE14006

H-Arg-Arg-Nal-Cys-Tyr-Arg-Lys-DLys-Pro-Tyr-Glu-Cit-Cys-Arg-OH (TE14006)

TE14006 was manufactured by the same method as Manufacturing Example 17. However, DLys (Boc) replaced DGlu (O-t-Bu) of the 8-position, and DGlu(O-t-Bu) replaced Arg (Pbf) of the 11-position respectively during the introduction of the amino acids from the 12-postion through the 1-position.

MANUFACTURING EXAMPLE 23

Manufacturing of Polypeptide TE14007

H-Arg-Arg-Nal-Cys-Tyr-Arg-Lys-DLys-Pro-Tyr-Arg-Cit-Cys-Glu-OH (TE14007)

TE14007 was manufactured by the same method as Manufacturing Example 17. However, instead of Fmoc-Arg(Pbf)-Alko resin attached with the first arginine of the 14-position, Fmoc-Glu(O-t-Bu)-Alko resin attached with glutamic acid of the 14-position was used, and also, DLys(Boc) replaced DGlu(O-t-Bu) of the 8-position during the introduction of the amino acids from the 12-postion through the 1-position.

MANUFACTURING EXAMPLE 24

Manufacturing of Polypeptide TE14011

H-Arg-Arg-Nal-Cys-Tyr-Cit-Lys-DGlu-Pro-Tyr-Arg-Cit-Cys-Arg-NH$_2$ (TE14011)

1. Synthesis of TE14011 Protected Polypeptide Resin:

Ale;2qfter removing Fmoc group from Fmoc-Rink amide resin by 20% piperidine/DMF, Fmoc-Arg(Pbf)-OH (2.5 eq) corresponding to the 14-position was added, and condensation reaction by DIPCDI-HOBt method was conducted in DMF. The progress of the condensation reaction was monitored by ninhydrin test of Kaiser, E. et al. (Anal. Biochem. 34: 595 (1970)).

2. Introduction of Amino Acids of the 13-Position to the 1-Position:

Similarly to the foregoing, Cys(Trt), Cit, Arg(Pbf), Tyr(t-Bu), Pro, DGlu(O-t-Bu), Lys(Boc), Cit, Tyr(t-Bu), Cys(Trt), Nal, Arg(Pbf), Arg(Pbf) residue was sequentially introduced into the Rink amide resin, and the protected polypeptide resin was obtained.

3. Deprotection and Cleavage of Polypeptide from Resin and Purification:

After removing Fmoc group from the protected polypeptide resin by 20% piperidine/DMF treatment, the resulting polypeptide resin was treated by 1 M TMSBr-thioanisole/TFA(trifluoroacetic acid) mixture (in the presence of m-cresol (100 eq), ethanedithiol (300 eq)) at 25° C. for 3 hours. The resin was separated by filtration from the reaction mixture, washed with TFA twice, the mixture of the filtrate and the wash solution was subjected to concentration in vacuo, the remaining residue was added with water-cooled dry ether, the resulting precipitation was separated from supernatant liquid by centrifugal sedimentation and decantation. The obtained residue was cleansed by cold ether, dissolved into 1 N acetic acid, and diluted by distilled water.

4. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC (COSMOSIL 5C18 AR-II column: acetonitrile water) and gel filtration chromatography (Sephadex G-15, eluate: 0.1N AcOH), a polypeptide of a single peak was obtained and freeze-dried. The purity was confirmed by HPLC.

MANUFACTURING EXAMPLE 25

Manufacturing of Polypeptide TE14012

H-Arg-Arg-Nal-Cys-Tyr-DGlu-Lys-DCit-Pro-Tyr-Arg-Cit-Cys-Arg-NH$_2$ (TE14012)

TE14012 was manufactured by the same method as Manufacturing Example 24. However, DCit replaced DGlu(O-t-Bu) of the 8-position, and DGlu(O-t-Bu) replaced Cit of the 6-position respectively during the introduction of the amino acids from the 13-postion through the 1-position.

MANUFACTURING EXAMPLE 26

Manufacturing of Polypeptide TE14013

H-Arg-Arg-Nal-Cys-Tyr-DGlu-Lys-DGlu-Pro-Tyr-Arg-Cit-Cys-Arg-NH$_2$ (TE14013)

TE14013 was manufactured by the same method as Manufacturing Example 24. However, DGlu(O-t-Bu) replaced Cit of the 6-position during the introduction of the amino acids from the 13-postion through the 1-position.

MANUFACTURING EXAMPLE 27

Manufacturing of Polypeptide TE14014

H-DGlu-Arg-Nal-Cys-Tyr-Cit-Lys-DGlu-Pro-Tyr-Arg-Cit-Cys-Arg-NH$_2$ (TE14014)

TE14014 was manufactured by the same method as Manufacturing Example 24. However, DGlu(O-t-Bu) replaced Arg(Pbf) of the 1-position during the introduction of the amino acids from the 13-postion through the 1-position.

MANUFACTURING EXAMPLE 28

Manufacturing of Polypeptide TE14015

H-Arg-Arg-Nal-Cys-Tyr-Cit-Lys-DGlu-Pro-DGlu-Arg-Cit-Cys-Arg-NH$_2$ (TE14015)

TE14015 was manufactured by the same method as Manufacturing Example 24. However, DGlu(O-t-Bu) replaced Tyr(t-Bu) of the 10-position during the introduction of the amino acids from the 13-postion through the 1-position.

MANUFACTURING EXAMPLE 29

Manufacturing of Polypeptide TE14016

H-Arg-Arg-Nal-Cys-Tyr-Cit-Lys-DGlu-Pro-Tyr-Arg-DGlu-Cys-Arg-NH$_2$ (TE14016)

TE14016 was manufactured by the same method as Manufacturing Example 24. However, DGlu(O-t-Bu) replaced Cit of the 12-position during the introduction of the amino acids from the 13-postion through the 1-position.

MANUFACTURING EXAMPLE 30

Manufacturing of Polypeptide AcTE14014-AcTE14016

Ac-DGlu-Arg-Nal-Cys-Tyr-Cit-Lys-DGlu-Pro-Tyr-Arg-Cit-Cys-Arg-NH$_2$ (AcTE14014)

Ac-Arg-Arg-Nal-Cys-Tyr-Cit-Lys-DGlu-Pro-DGlu-Arg-Cit-Cys-Arg-NH$_2$ (AcTE14015)

Ac-Arg-Arg-Nal-Cys-Tyr-Cit-Lys-DGlu-Pro-Tyr-Arg-DGlu-Cys-Arg-NH$_2$ (AcTE14016)

Acetylated TE14014-TE14016 were manufactured by the same method as Manufacturing Example 27-29. However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1 M TMSBr-thioanisole/TFA(trifluoroacetic acid) mixture (in the presence of m-cresol (100 eq), ethanedithiol (300 eq)) at 25° C. for 3 hours.

MANUFACTURING EXAMPLE 31

Manufacturing of Polypeptide TF1

Ac-Arg-Arg-Nal-Cys-Tyr-Cit-Lys-DGlu-Pro-Tyr-Arg-Cit-Cys-Arg-NH$_2$ (TF1: AcTE14011)

TF1 was manufactured by the same method as Manufacturing Example 24.

However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1 M TMSBr-thioanisole/TFA(trifluoroacetic acid) mixture (in the presence of m-cresol (100 eq), ethanedithiol (300 eq)) at 25° C. for 2 hours (in case of C-terminal being carboxylic acid) or for 3 hours (in case of C-terminal being amide).

MANUFACTURING EXAMPLE 32

Manufacturing of Polypeptide TF2 guanyl-Arg-Arg-Nal-Cys-Tyr-Cit-Lys-DGlu-Pro-Tyr-Arg-Cit-Cys-Arg-NH$_2$ (TF2: guanyl-TE14011)

TF2 was manufactured by the same method as Manufacturing Example 24.

However, after removing Fmoc group from the protected polypeptide resin by 20% piperidine/DMF treatment, the resulting polypeptide resin was guanylated by 1H-pyrazole-1-carboxamidine (5 eq)-N,N-diisopropylethylamine (10 eq)/DMF treatment, and treated by 1M TMSBr-thioanisole/TFA(trifluoroacetic acid) mixture (in the presence of m-cresol (100 eq), ethandithiol (300 eq)) at 25° C. for 3 hours.

MANUFACTURING EXAMPLE 33

Manufacturing of Polypeptide TF3

TMguanyl-Arg-Arg-Nal-Cys-Tyr-Cit-Lys-DGlu-Pro-Tyr-Arg-Cit-Cys-Arg-NH$_2$ (TF3: TMguanyl-TE14011)

TF3 was manufactured by the same method as Manufacturing Example 24.

However, after removing Fmoc group from the protected polypeptide resin by 20% piperidine/DMF treatment, the resulting polypeptide resin was tetramethylguanylated by 2-(1H-benzotriazole-1-yl)-1,1,3,3-tetramethyluronium tetrafluoroborate (5 eq)/DMF treatment, and treated with 1 M TMSBr-thioanisole/TFA(trifluoroacetic acid) mixture (in the presence of m-cresol (100 eq), ethanedithiol (300 eq)) at 25° C. for 3 hours.

MANUFACTURING EXAMPLE 34

Manufacturing of Polypeptide TF4

TMguanyl-Arg-Nal-Cys-Tyr-Cit-Lys-DGlu-Pro-Tyr-Arg-Cit-Cys-Arg-NH$_2$ (TF4: TMguanyl-TE14011 (2-14))

TF4 was manufactured by the same method as Manufacturing Example 24.

However, arginine of the 1-position was not condensed.

MANUFACTURING EXAMPLE 35

Manufacturing of Polypeptide TF5

4F-benzoyl-Arg-Arg-Nal-Cys-Tyr-Cit-Lys-DGlu-Pro-Tyr-Arg-Cit-Cys-Arg-NH$_2$ (TF5: 4F-benzoyl-TE14011)

TF5 was manufactured by the same method as Manufacturing Example 24.

However, after removing Fmoc group from the protected polypeptide resin by 20% piperidine/DMF treatment, the resulting polypeptide resin was condensed with 4-fluorobenzoic acid (2.5 eq) by DIPCDI-HOBt method, and treated with 1 M TMSBr-thioanisole/TFA(trifluoroacetic acid) mixture (in the presence of m-cresol (100 eq), ethanedithiol (300 eq)) at 25° C. for 3 hours.

MANUFACTURING EXAMPLE 36

Manufacturing of Polypeptide TF6

2F-benzoyl-Arg-Arg-Nal-Cys-Tyr-Cit-Lys-DGlu-Pro-Tyr-Arg-Cit-Cys-Arg-NH$_2$ (TF6: 2F-benzoyl-TE 14011)

TF6 was manufactured by the same method as Manufacturing Example 24.

However, after removing Fmoc group from the polypeptide resin protected by protecting group by 20% piperidine/DMF treatment, the resulting polypeptide resin was condensed with 2-fluorobenzoic acid (2.5 eq) by DIPCDI-HOBt method, and treated with 1M TMSBr-thioanisole/TFA(trifluoroacetic acid) mixture (in the presence of m-cresol (100 eq), ethanedithiol (300 eq)) at 25° C. for 3 hours.

MANUFACTURING EXAMPLE 37

Manufacturing of Polypeptide TF7

APA-Arg-Nal-Cys-Tyr-Cit-Lys-DGlu-Pro-Tyr-Arg-Cit-Cys-Arg-NH$_2$ (TF7: APA-TE14011 (2-14))

TF7 was manufactured by the same method as Manufacturing Example 24.

However, instead of Arg(Pbf) of the 1-position, Fmoc-aminopentanoic acid was introduced after the introduction of the amino acids from the 13-postion through the 1-position.

MANUFACTURING EXAMPLE 38

Manufacturing of Polypeptide TF8 desamino-R-Arg-Nal-Cys-Tyr-Cit-Lys-DGlu-Pro-Tyr-Arg-Cit-Cys-Arg-NH$_2$ (TF8: desamino-R-TE14011 (2-14))

TF8 was manufactured by the same method as Manufacturing Example 24.

However, instead of Arg(Pbf) of the 1-position, Fmoc-5-aminopentanic acid was introduced after the introduction of the amino acids from the 13-postion through the 1-position.

Furthermore, after removing Fmoc group from the protected polypeptide resin by 20% piperidine/DMF treatment, the resulting polypeptide resin was guanylated by 1H-pyrazole-1-carboxamidine (5 eq)/DMF treatment, and treated by 1 M TMSBr-thioanisole/TFA(trifluoroacetic acid) mixture (in the presence of m-cresol (100 eq), ethanedithiol (300 eq)) at 25° C. for 3 hours.

MANUFACTURING EXAMPLE 39

Manufacturing of Polypeptide TF9 guanyl-Arg-Nal-Cys-Tyr-Cit-Lys-DGlu-Pro-Tyr-Arg-Cit-Cys-Arg-NH$_2$ (TF9: guanyl-TE14011 (2-14))

TF9 was manufactured by the same method as Manufacturing Example 32.

However, arginine of the 1-position was not condensed.

Furthermore, after removing Fmoc group from the protected polypeptide resin by 20% piperidine/DMF treatment, the resulting polypeptide resin was guanylated by 1H-pyrazole-1-carboxamidine (5 eq)/DMF treatment, and treated by 1 M TMSBr-thioanisole/TFA(trifluoroacetic acid) mixture (in the presence of m-cresol (100 eq), ethanedithiol (300 eq)) at 25° C. for 3 hours.

MANUFACTURING EXAMPLE 40

Manufacturing of Polypeptide TF10 succinyl-Arg-Nal-Cys-Tyr-Cit-Lys-DGlu-Pro-Tyr-Arg-Cit-Cys-Arg-NH$_2$ (TF10: succinyl-TE14011 (2-14))

TF10 was manufactured by the same method as Manufacturing Example 24.

However, arginine of the 1-position was not condensed.

Also, after removing Fmoc group from the protected polypeptide resin by 20% piperidine/DMF treatment, the resulting polypeptide resin was hemisuccinylated by succinic anhydride (5 eq)/pyridine treatment, and treated by 1 M TMSBr-thioanisole/TFA(trifluoroacetic acid) mixture (in the presence of m-cresol (100 eq), ethanedithiol (300 eq)) at 25° C. for 3 hours.

MANUFACTURING EXAMPLE 41

Manufacturing of Polypeptide TF11 glutaryl-Arg-Nal-Cys-Tyr-Cit-Lys-DGlu-Pro-Tyr-Arg-Cit-Cys-Arg-NH$_2$ (TF11: glutaryl-TE14011 (2-14))

TF11 was manufactured by the same method as Manufacturing Example 40.

However, after removing Fmoc group from the protected polypeptide resin by 20% piperidine/DMF treatment, the resulting polypeptide resin was hemiglutarylated by glutaric anhydride (5 eq)/pyridine treatment, and treated by 1 M TMSBr-thioanisole/TFA(trifluoroacetic acid) mixture (in the presence of m-cresol (100 eq), ethanedithiol (300 eq)) at 25° C. for 3 hours.

MANUFACTURING EXAMPLE 42

Manufacturing of Polypeptide TF12 deaminoTMG-APA-Arg-Nal-Cys-Tyr-Cit-Lys-DGlu-Pro-Tyr-Arg-Cit-Cys-Arg-NH$_2$ (TF12: deaminoTMG-APA-TE14011 (2-14))

TF12 was manufactured by the same method as Manufacturing Example 24.

However, instead of Arg(Pbf) of the I-position, Fmoc-5-aminopentanoic acid was introduced after the introduction of the amino acids from the 13-postion through the 1-position.

Furthermore, after removing Fmoc group from the protected polypeptide resin by 20% piperidine/DMF treatment, the resulting polypeptide resin was tetramethylguanylated by 2-(1H-benzotriazole-1-yl)-1,1,3,3-tetramethyluronium tetrafluoroborate (5 eq)/DMF treatment, and treated by 1 M TMSBr-thioanisole/TFA(trifluoroacetic acid) mixture (in the presence of m-cresol (100 eq), ethanedithiol (300 eq)) at 25° C. for 3 hours.

MANUFACTURING EXAMPLE 43

Manufacturing of Polypeptide TF15

R—CH2-Arg-Nal-Cys-Tyr-Cit-Lys-DGlu-Pro-Tyr-Arg-Cit-Cys-Arg-NH$_2$ (TF15: R—CH2NH-RTE14011)

TF15 was manufactured by the same method as Manufacturing Example 24.

However, at the I-position, Fmoc-Arg(Pbf)-H (aldehyde) was condensed by reductive amidation (NaB(CN)H3 (3 eq), AcOH (1 eq)/DMF) instead of the condensation of Fmoc-Arg(Pbf)-OH after the introduction of the amino acids from the 13-postion through the 2-position.

MANUFACTURING EXAMPLE 44

Manufacturing of Polypeptide TF17

H-Arg-Nal-Cys-Tyr-Cit-Lys-DGlu-Pro-Tyr-Arg-Cit-Cys-Arg-NH$_2$ (TF17) (TF17: TE14011 (2-14))

TF17 was manufactured by the same method as Manufacturing Example 24.
However, arginine of the 1-position was not condensed.

MANUFACTURING EXAMPLE 45

Manufacturing of Polypeptide TF18

TMguanyl-Arg-Arg-Nal-Cys-Tyr-Cit-Lys-DCit-Pro-Tyr-Arg-Cit-Cys-Arg-NH$_2$ (TF18: TMguanyl-TC14012)

TF18 was manufactured by the same method as Manufacturing Example 9.
However, after removing Fmoc group from the protected polypeptide resin by 20% piperidine/DMF treatment, the resulting polypeptide resin was tetramethylguanylated by 2-(1H-benzotriazole-1-yl)-1,1,3,3-tetramethyluronium tetrafluoroborate (5 eq)/DMF treatment, and treated by 1 M TMSBr-thioanisole/TFA (trifluoroacetic acid) mixture (in the presence of m-cresol (100 eq), ethanedithiol (300 eq)) at 25° C. for 3 hours.

MANUFACTURING EXAMPLE 46

Manufacturing of Polypeptide TF19

ACA-Arg-Arg-Nal-Cys-Tyr-Cit-Lys-DCit-Pro-Tyr-Arg-Cit-Cys-Arg-NH$_2$ (TF19: ACA-TC14012)

TF19 was manufactured by the same method as Manufacturing Example 9.
However, next to Arg(Pbf) of the 1-position, Fmoc-6-aminohexanoic acid was introduced after the introduction of the amino acids from the 13-postion through the 1-position.

MANUFACTURING EXAMPLE 47

Manufacturing of Polypeptide TF20

ACA-Arg-Arg-Nal-Cys-Tyr-Arg-Lys-DLys-Pro-Tyr-Arg-Cit-Cys-Arg-OH (TF20: ACA-T140)

TF20 was manufactured by the same method as Manufacturing Example 17.
However, DLys(Boc) replaced DGlu(O-t-Bu) of the 8-position, and Fmoc-6-aminohexanoic acid replaced Arg (Pbf) of the 1-position respectively after the introduction of the amino acids from the 12-postion through the 1-position.

MANUFACTURING EXAMPLE 48

Manufacturing of Polypeptide TZ14011

H-Arg-Arg-Nal-Cys-Tyr-Cit-Arg-DLys-Pro-Tyr-Arg-Cit-Cys-Arg-NH$_2$ (TZ14011)

TZ14011 was manufactured by the same method as Manufacturing Example 24.
However, DLys(Boc) replaced DGlu(O-t-Bu) of the 8-position, and Arg (Pbf) replaced Lys (Boc) of the 7-position respectively during the introduction of the amino acids from the 13-postion through the 1-position.

MANUFACTURING EXAMPLE 49

Manufacturing of Polypeptide AcTZ14011

Ac-Arg-Arg-Nal-Cys-Tyr-Cit-Arg-DLys-Pro-Tyr-Arg-Cit-Cys-Arg-NH$_2$ (AcTZ14011)

AcTZ14011 was manufactured by the same method as Manufacturing Example 48. However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1M TMSBr-thioanisole/TFA (trifluoroacetic acid) mixture (in the presence of m-cresol (100 eq), ethanedithiol (300 eq)) at 25° C. for 3 hours.

MANUFACTURING EXAMPLE 50

Manufacturing of Polypeptide TN14003

H-Arg-Arg-Nal-Cys-Tyr-Cit-Lys-DLys-Pro-Tyr-Arg-Cit-Cys-Arg-NH$_2$ (TN14003)

TN14003 was manufactured by the same method as Manufacturing Example 9. However, DLys(Boc) replaced DCit of the 8-position during the introduction of the amino acids from the 13-postion through the 1-position.

MANUFACTURING EXAMPLE 51

Manufacturing of Polypeptide TN14005

H-Arg-Arg-Nal-Cys-Tyr-Arg-Lys-DCit-Pro-Tyr-Arg-Cit-Cys-Arg-NH$_2$ (TN14005)

TN14005 was manufactured by the same method as Manufacturing Example 9. However, Arg(Pbf) replaced Cit of the 6-position during the introduction of the amino acids from the 13-postion through the 1-position.

MANUFACTURING EXAMPLE 52

Manufacturing of Polypeptide AcTN14003

Ac-Arg-Arg-Nal-Cys-Tyr-Cit-Lys-DLys-Pro-Tyr-Arg-Cit-Cys-Arg-NH$_2$ (AcTN14003)

AcTN14003 was manufactured by the same method as Manufacturing Example 50.
However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1 M TMSBr-thioanisole/TFA (trifluoroacetic acid) mixture (in the presence of m-cresol (100 eq), ethanedithiol (300 eq)) at 25° C. for 3 hours.

MANUFACTURING EXAMPLE 53

Manufacturing of Polypeptide AcTN14005

Ac-Arg-Arg-Nal-Cys-Tyr-Arg-Lys-DCit-Pro-Tyr-Arg-Cit-Cys-Arg-NH$_2$ (AcTN14005)

AcTN14005 was manufactured by the same method as Manufacturing Example 51. However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1 M TMSBr-thioanisole/TFA (trifluoroacetic acid) mixture (in the presence of m-cresol (100 eq), ethanedithiol (300 eq)) at 25° C. for 3 hours.

MANUFACTURING EXAMPLE 54

Manufacturing of Polypeptide 4F-benzoyl-TN14003

4F-benzoyl-Arg-Arg-Nal-Cys-Tyr-Cit-Lys-DLys-Pro-Tyr-Arg-Cit-Cys-Arg-NH$_2$ (4F-benzoyl-TN14003)

1. Synthesis of 4F-benzoyl-TN14003 Protected Polypeptide Resin:

After removing Fmoc group from Fmoc-Rink amide resin (0.34 mmol/g) 2.94 g (1 mmol) by 20% piperidine/DMF, Fmoc-Arg(Pbf)-OH (2.5 eq) corresponding to the 14-position was added, and condensation reaction by DIPCDI-HOBt method was conducted in DMF. The progress of the condensation reaction was monitored by ninhydrin test of Kaiser, E. et al. (Anal. Biochem. 34: 595 (1970)).

2. Introduction of Amino Acids of the 13-Position to 1 Position:

Similarly to the foregoing, Cys(Trt), Cit, Arg(Pbf), Tyr(t-Bu), Pro, DLys(Boc), Lys(Boc), Cit, Tyr(t-Bu), Cys(Trt), Nal, Arg(Pbf), Arg(Pbf) residue was sequentially introduced into Rink amide resin, 4-fluorobenzoic acid (2.5 eq) was condensed at the last N-terminal by DIPCDI-HOBt method and the protected polypeptide resin was obtained.

3. Deprotection and Clearage of Polypeptide from Resin and Purification:

The protected polypeptide resin(1 mmol) was treated by 270 mL of 1 M TMSBr-thioanisole/TFA(trifluoroacetic acid) mixture (in the presence of m-cresol (100 eq), ethanedithiol (300 eq)) at 25° C. for 3 hours. The resin was separated by filtration from the reaction mixture, washed with TFA 5 mL twice, the mixture of the filtrate and the wash solution was subjected to concentration in vacuo. The remaining residue was added with 300 mL of water-cooled dry ether, the resultant sediment was separated from supernatant liquid by centrifugal sedimentation and decantation. The obtained residue was cleansed by cold ether, dissolved into 500 mL of 1 N acetic acid, and diluted to 2.5 L by distilled water.

4. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC (COSMOSIL 5C 18 AR-II column: acetonitrile water) and gel filtration chromatography (Sephadex G-15, eluate: 0.1 N AcOH), a polypeptide of a single peak was obtained and freeze-dried. The purity was confirmed by HPLC.

Yield: 551.5 mg (6 TFA salt) (19.4%) [α]D28.6=−10.25 (c 0.39, H2O) Ionspray mass spectrum (IS-MS): C97H144FN33O19S2 Calculated Value: 2159.52 Actual Measurement Value: 2161 (triple stage quadrupole mass spectrometry API-IIIE (Sciex))

MANUFACTURING EXAMPLE 55

Manufacturing of Polypeptide 4F-benzoyl-TE14011-Me 4-fluorobenzoyl-Arg-Arg-Nal-Cys-Tyr-Cit-Lys-DGlu-Pro-Tyr-Arg-Cit-Cys-Arg-NHMe (4F-benzoyl-TE 14011-Me)

1. Synthesis of 4F-benzoyl-TE14011-Me Protected Polypeptide Resin:

4-sulfamylbutyryl AM NovaGel resin was added with. Fmoc-Arg(Pbf)-OH (4 eq) corresponding to the 14-position, and, in CHCl3, condensation reaction by PyBOP (3 eq)-DIPEA (6 eq) method was conducted at 0° C. (This condensation reaction was repeated twice). After removing Fmoc group by 20% piperidine/DMF, Fmoc-Cys(Trt)-OH (2.5 eq) corresponding to the 13-position was added, and condensation reaction by DIPCDI-HOBt method was conducted in DMF. The degree of the progress of the condensation reaction was monitored by ninhydrin test of Kaiser, E. et al. (Anal. Biochem., 34: 595 (1970)).

Similarly to the foregoing for the introduction of amino acids from the 12-position to the I-position, Cit, Arg(Pbf), Tyr(t-Bu), Pro, DGlu(O-t-Bu), Lys(Boc), Cit, Tyr(t-Bu), Cys(Trt), Nal, Arg(Pbf), Arg(Pbf) residue was sequentially introduced into the sulfamylbutyryl resin, 4-fluorobenzoic acid (2.5 eq) was condensed at the last N-terminal by DIPCDI-HOBt method to yield the protected polypeptide resin.

2. C-Terminal Alkylamidation, Deprotection and Clearage of Polypeptide from Resin and Purification:

The protected polypeptide resin was cyanomethylated by ICH2CN (40 eq), DIPEA (10 eq)/NMP treatment (48 hours), then, treated by methylamine (excess) in THF/DMF, and the protected C-terminally methylamidated polypeptide was isolated from the resin. The protected polypeptide was treated by 1 M TMSBr-thioanisole/TFA(trifluoroacetic acid) mixture (in the presence of m-cresol (100 eq), ethanedithiol (300 eq)) at 25° C. for 3 hours. The reaction solution was subjected to concentration in vacuo, the remaining residue was added with water-cooled dry ether, the resultant sediment was separated from supernatant liquid by centrifugal sedimentation and decantation. The obtained residue was cleansed by cold ether, dissolved into 1N acetic acid, and diluted by distilled water.

3. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC (COSMOSIL 5C18 AR-II column: acetonitrile water) and gel filtration chromatography (Sephadex G-15, eluate: 0.1 N AcOH), a polypeptide of a single peak was obtained and freeze-dried. The purity was confirmed by HPLC.

MANUFACTURING EXAMPLE 56

Manufacturing of Polypeptide 4F-benzoyl-TE14011-Et 4-fluorobenzoyl-Arg-Arg-Nal-Cys-Tyr-Cit-Lys-DGlu-Pro-Tyr-Arg-Cit-Cys-Arg-NHEt (4F-benzoyl-TE 14011-Et)

4F-benzoyl-TE14011-Et was manufactured by the same method as Manufacturing Example 55. However, ethylamine replaced methylamine.

MANUFACTURING EXAMPLE 57

Manufacturing of Polypeptide 4F-benzoyl-TE14011-iPr 4-fluorobenzoyl-Arg-Arg-Nal-Cys-Tyr-Cit-Lys-DGlu-Pro-Tyr-Arg-Cit-Cys-Arg-NHiPr (4F-benzoyl-TE 14011-iPr)

4F-benzoyl-TE14011-iPr was manufactured by the same method as Manufacturing Example 55. However, isopropylamine replaced methylamine.

MANUFACTURING EXAMPLE 58

Manufacturing of Polypeptide 4F-benzoyl-TE14011-tyramine 4-fluorobenzoyl-Arg-Arg-Nal-Cys-Tyr-Cit-Lys-DGlu-Pro-Tyr-Arg-Cit-Cys-Arg-tyramine (4F-benzoyl-TE 14011-tyramine)

4F-benzoyl-TE14011-tyramine was manufactured by the same method as Manufacturing Example 55. However, tyramine(p-hydroxyphenylethylamine) replaced methylamine.

EXPERIMENTAL EXAMPLE 1

The Inhibitory Activity of the Peptides of the Present Invention Against CXCL12 Binding to CXCR4 Receptor 50 μL of Jurkat human T-cell leukemia cells ($6 \times 10^6$ cells/mL) suspended in buffer (Dulbecco's PBS solution (pH 7.0) containing 0.5% BSA, 20 mM HEPES), 25 μL of test compounds (Table 1: each compound being synthesized in the form of acetate salt) diluted by buffer and 25 μL of 200 pM 125I-CXCL12 solution were respectively dispensed to each well of the plate, and were subjected to fixation reaction for 1 hour at room temperature. After reaction, suction was made toward the reaction solution by 96 well GF/C filter plate, and each well's radioactivity was measured by top count. As the radioactivity index of 100% when the test compound was not added, and 0% when 100 nM of non-radioisotope-labeled CXCL12 was added, the inhibitory activity of each test compound was measured. The result is indicated in the following Table 1.

| No. | IC50 (nM) |
|---|---|
| TE14002 | 680 |
| TE14003 | 5 |// 
| TE14004 | 6.8 |
| TE14005 | 2.2 |
| TE14006 | 5.6 |
| TE14011 | 2.9 |
| TE14012 | 5.4 |
| TE14013 | 9.3 |
| 4F-benzoyl-TN14003 | 0.99 |
| TF1 | 11 |
| TF2 | 3.3 |
| TF3 | 9.6 |
| TF4 | 9.9 |
| TF5 | 2.8 |
| TF6 | 3.9 |
| TF7 | 5.7 |
| TF8 | 8.2 |
| TF9 | 250 |
| TF10 | 48 |
| TF11 | 630 |
| TF12 | 4.6 |
| TF13 | 21 |
| TF14 | 49 |
| TF15 | 95 |
| TF17 | 79 |
| TF18 | 8 |
| TF19 | 4.5 |
| TF20 | 3.5 |

The results indicated in Table 1 shows that the compounds have potent binding inhibitory activity.

EXPERIMENTAL EXAMPLE 2

The Inhibitory Activity of TE-14005 Against Breast Cancer Cell Migration Induced by CXCL12

Transwell filter (polycarbonate filter, 8 μm diameter, Costar Company) was treated at 37° C. for 6 hours in 10 μg/mL fibronectin solution and air-dried. 100 nM of CXCL12 (R&D System Company) and 600 μL/well of buffer-A (0.1% bovine serum albumin, DMEM (GibcoBRL) containing 12 mM HEPES) containing the test compound were added to the lower chamber of the Transwell. The test compound and human breast cancer MDA-MB-231 cells (purchased from American Tissue Culture Collection), and 100 μL/well of buffer A containing $2 \times 10^6$ cells/mL were added to the upper chamber. After 15 hours' incubation at 37° C. in 5% $CO_2$ incubator, the upper surface of the filter was wiped and the cell was removed, and then the cell on the lower surface of the filter was fixed and stained with 25% methanol solution containing 0.5% crystal violet (Wako Pure Chemical Ind.), washed by distilled water and air-dried. Cutting off the filter part, adding 0.1 M sodium citrate/50% ethanol solution, and eluting crystal violet absorption at 550 nm was measured. The result is indicated in FIG. 1. Control (−) indicates the migration when CXCL12 was not added. By adding CXCL12, the migration of MDA-MB-231 cells was enhanced. This CXCL12-induced migration of MDA-MB-231 cells was inhibited by 10 nM of the antagonist, TE14005.

EXPERIMENTAL EXAMPLE 3

The Inhibitory Activity of TC14012 and TN14003 Against CXCL12 Binding to CXCR4 Receptor 50 μL of Jurkat human T-cell leukemia cells ($6 \times 10^6$ cells/mL) suspended in buffer (Dulbecco's PBS solution (pH 7.0)

containing 0.5% BSA, 20 mM HEPES), 25 μL of test compounds (Table 2: each compound being synthesized in the form of acetate salt) diluted by buffer and 25 μL of 200 p M 125I-CXCL12 solution were respectively dispensed to each well of the plate, and were subjected to fixation reaction for 1 hour at room temperature. After reaction, suction was made toward the reaction solution by 96 well GF/C filter plate, and each well's radioactivity was measured by top count. As the radioactivity index of 100% when the test compound was not added, and 0% when 100 nM of non-radioisotope-labeled CXCL12 was added, the inhibitory activity of each test compound was measured. The result is indicated in the following Table 2.

| No. | IC50 (nM) |
|---|---|
| TC14012 | 2.7 |
| TN14003 | 2.6 |

The result indicated in Table 2 shows that the compounds have potent binding inhibitory activity.

EXPERIMENTAL EXAMPLE 4

The Inhibitory Activity of TC-14012 Against Breast Cancer Cell Migration Induced by CXCL12

Figure 2:
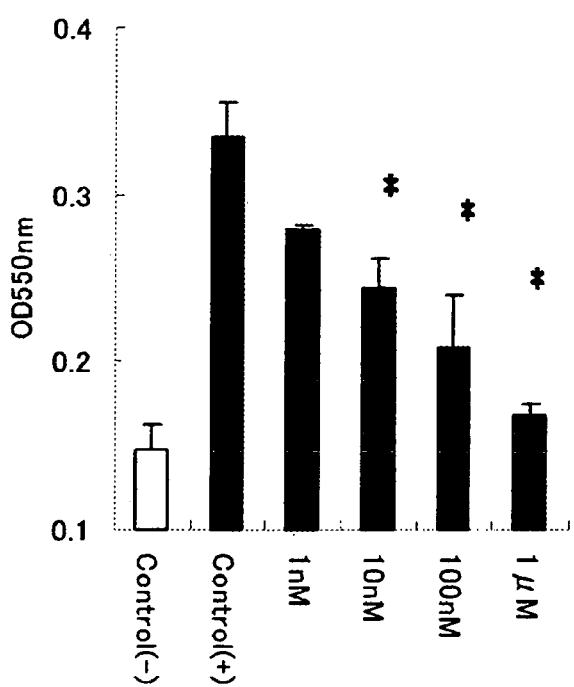
FIG. 2 shows the inhibitory activity of TC-14012 against the migration of breast cancer cells induced by CXCL12. The vertical axis shows the migration of cells (absorption of light: OD550 nm). From the left, it shows the result (mean value±standard deviation, n=2) obtained respectively when CXCL12 was not added (negative control), when CXCL12 was added (positive control), when CXCL12 and TC-14012 1 nM were added, when CXCL12 and TC-14012 10 nM were added, when CXCL12 and TC-14012 100 nM were added, and when CXCL12 and TC-14012 1 µM were added. * indicates the significance of each TC-14012 added group compared with the positive control group (Williams' test, p 0.025).

Transwell filter (polycarbonate filter, 8 μm diameter, Costar Company) was treated at 37° C. for 6 hours in 10 μg/mL fibronectin solution and air-dried. 100 nM of CXCL12 (R&D System Company) and 600 μL/well of buffer-A (0.1% bovine serum albumin, DMEM (GibcoBRL) containing 12 mM HEPES) containing the test compound were added to the lower chamber of the Transwell. The test compound and human breast cancer MDA-MB-231 cells (purchased from American Tissue Culture Collection), and 100 μL/well of buffer A containing $2\times10^6$ cells/mL were added to the upper chamber. After 15 hours' incubation at 37° C. in 5% $CO_2$ incubator, the upper surface of the filter was wiped and the cell was removed, and then the cell on the lower surface of the filter was fixed and stained with 25% methanol solution containing 0.5% crystal violet (Wako Pure Chemical Ind.), washed by distilled water and air-dried. Cutting off the filter part, adding 0.1 M sodium citrate/50% ethanol solution, and eluting crystal violet absorption at 550 nm was measured. The result is indicated in FIG. 2. Control (−) indicates the migration when CXCL12 was not added. By adding CXCL12, the migration of MDA-MB-231 cells was enhanced. This CXCL12-induced migration of MDA-MB-231 cells was inhibited by 10 nM of the antagonist, TE14005.

EXPERIMENTAL EXAMPLE 5

The Inhibitory Activity of 4Fbenzoyl-TN-14003 Against T-Cell Derived Leukemia Cell Migration Induced by CXCL12

30 nM of CXCL12 (R&D System Company) and 600 μL/well of buffer-A (0.1% bovine serum albumin, DMEM (GibcoBRL) containing 12 mM HEPES) containing the test compound were added to the lower chamber of Transwell filter (polycarbonate filter, 8 μm diameter, Costar Company). The test compound and human cell-derived leukemia SUP-T1 cells (purchased from American Tissue Culture Collection), and 100 μL/well of buffer A containing $2\times10^6$ cells/mL were added to the upper chamber.

Figure 3:
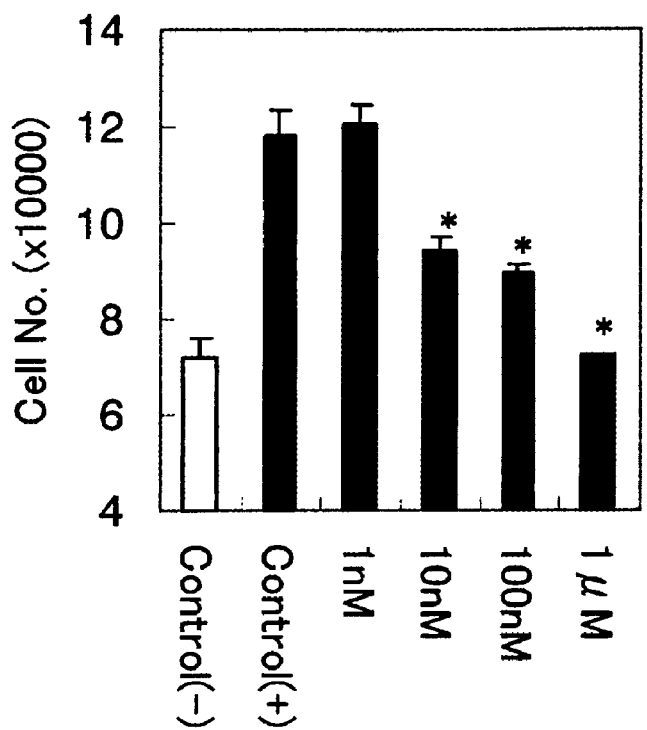
FIG. 3 shows the inhibitory activity of 4Fbenzoyl-TN-14003 against the migration of T-cell originating leukemia cells induced by CXCL12. The vertical axis shows the migration of cells (the number of cells). From the left, it shows the result (mean value±standard deviation, n=2) obtained respectively when CXCL12 was not added (negative control), when CXCL12 was added (positive control), when CXCL12 and 4Fbenzoyl-TN-14003 1 nM were added, when CXCL12 and 4Fbenzoyl-TN-14003 10 nM were added, when CXCL12 and 4Fbenzoyl-TN-14003 100 nM were added, and when CXCL12 and 4Fbenzoyl-TN-14003 1 µM were added. * indicates the significance of each 4Fbenzoyl-TN-14003 added group compared with the positive control group (Williams' test, p 0.025).

After 4 hours' incubation at 37° C. in 5% $CO_2$ incubator, the number of the cells moved to the lower chamber was counted by Coulter counter. The result is indicated in FIG. 3. Control (−) indicates the migration when CXCL12 was not added. Control (+) indicates the migration when CXCL12 was added. By adding CXCL12, the migration of SUP-T1 cells was enhanced. This CXCL12-induced migration of SUP-T1 cells was inhibited by 10 nM of the antagonist, 4Fbenzoyl-TN-14003. From the foregoing, 4Fbenzoyl-TN-14003, by inhibiting the movement of T-cells at low concentrations, is considered to be useful as an inhibitory drug for chronic rheumatoid arthritis.

EXPERIMENTAL EXAMPLE 6

The Inhibitory Activity of 4Fbenzoyl-TN-14003 Against Breast Cancer Cell Migration Induced by CXCL12

Figure 4:
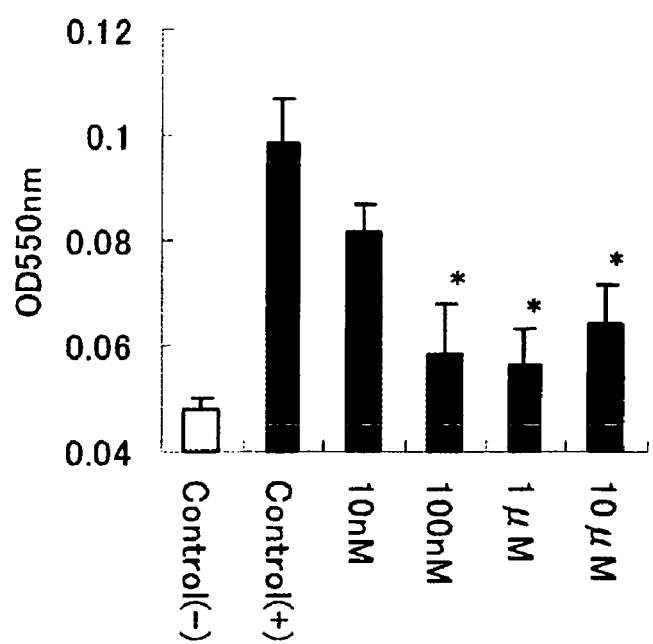
FIG. 4 shows the inhibitory activity of 4Fbenzoyl-TN-14003 against the migration of breast cancer cells induced by CXCL12. The vertical axis shows the migration of cells (absorption of light: OD550 nm). From the left, it shows the result (mean value±standard deviation, n=2) obtained respectively when CXCL12 was not added (negative control), when CXCL12 was added (positive control), when CXCL12 and 4Fbenzoyl-TN-14003 10 nM were added, when CXCL12 and 4Fbenzoyl-TN-14003 100 nM were added, when CXCL12 and 4Fbenzoyl-TN-14003 1 μM were added, and when CXCL12 and 4Fbenzoyl-TN-14003 10 μM were added. * indicates the significance of each 4Fbenzoyl-TN-14003 added group compared with the positive control group (Williams' test, p 0.025).

Transwell filter (polycarbonate filter, 8 μm diameter, Costar Company) was treated at 37° C. overnight in 10 mg/mL fibronectin solution and air-dried. 100 nM of CXCL12 (R&D System Company) and 600 μL/well of buffer-A (0.1% bovine serum albumin, DMEM (GibcoBRL) containing 12 mM HEPES) containing 4Fbenzoyl-TN-14003 were added to the lower chamber of Transwell. 4Fbenzoyl-TN-14003 and human breast cancer MDA-MB-231 cells (purchased from American Tissue Culture Collection), and 100 μL/well of buffer A containing $2\times10^6$ cells/mL were added to the upper chamber. The test compound and human breast cancer MDA-MB-231 cells (purchased from American Tissue Culture Collection), and 100 mL/well of buffer A containing $2\times10^6$ cells/mL were added to the upper chamber. After 15 hours' incubation at 37° C. in 5% $CO_2$ incubator, the upper surface of the filter was wiped and the cell was removed, and then the cell on the lower surface of the filter was fixed and stained with 25% methanol solution containing 0.5% crystal violet (Wako Pure Chemical Ind.), washed by distilled water and air-dried. Cutting off the filter part, adding 0.1 M sodium citrate/50% ethanol solution, and eluting crystal violet absorption at 550 nm was measured. The result is indicated in FIG. 4. Control (−) indicates the migration when CXCL12 was not added. Control (+) indicates the migration when CXCL12 was added. By adding CXCL12, the migration of MDA-MB-231 cells was enhanced. This CXCL12-induced migration of MDA-MB-231 cells was inhibited by 10 nM of the antagonist, 4Fbenzoyl-TN-14003.

EXPERIMENTAL EXAMPLE 7

Anti-Metastatic Activity of 4Fbenzoyl-TN-14003

Figure 5:
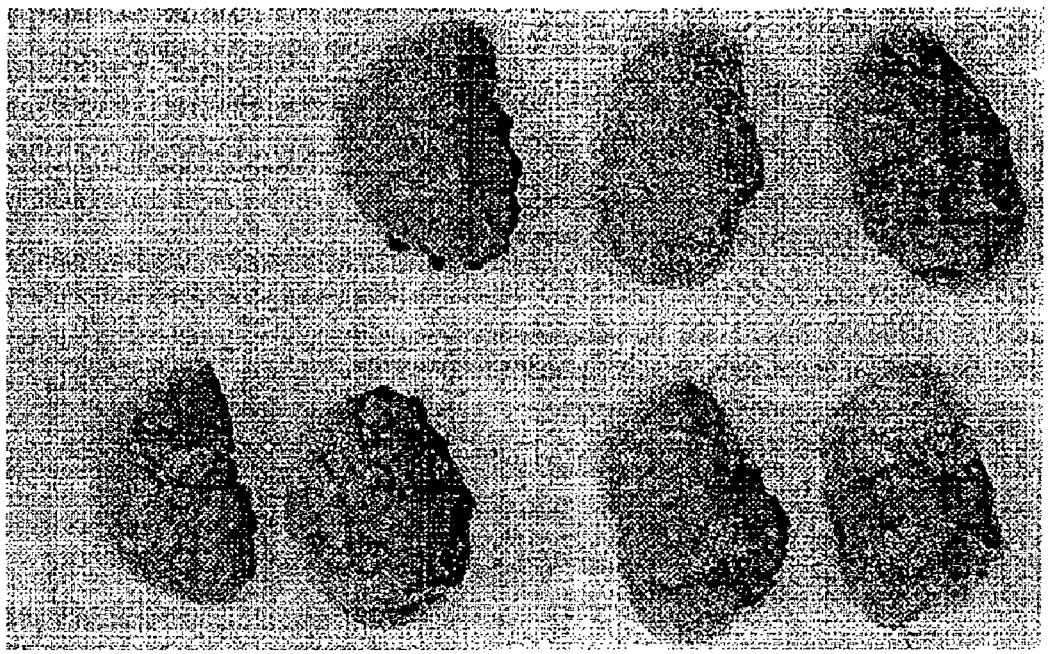
FIG. 5 is a chromatic figure of lung tissue displaying the inhibitory activity of 4Fbenzoyl-TN-14003 in a mouse transplanted with human breast cancer cells.
Figure 5:
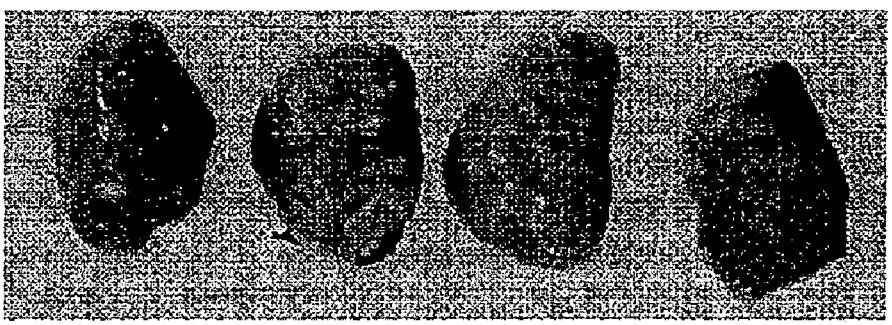

MDA-MB-231 human breast cancer cells ($10^6$ cells) were implanted intravenously into the tails of five week-old female CB-17 SCID mice (Crea Japan, Inc.). 4Fbenzoyl-TN-14003 was prepared at 80 mg/mL in physiologic saline solution, was included into sustained-releasing osmotic pumps (Alzet pump, Alza Corporation, usable for 2 week sustained-release; the dose was equivalent to 18.2 mg/kg/day), and was intradermally loaded to the backs of the mice on the date immediately preceding the implantation. Further, 14 days after the implantation, Alzet pumps containing an equal dose of the drug were additionally loaded. To the control group, Alzet pumps injected with physiological saline solution were additionally loaded. 28 days after the implantation, the mice were dissected, about 2 mL of 0.2% Evans' Blue solution was injected through windpipes, and lungs were stained. The lungs were taken out, soaked in Bouin's liquid, stained and fixed. By eye observation of metastatic focus (yellow stained potion), the evaluation was conducted to determine whether or not the compound exhibited more evident anti-metastatic activity. The result is indicated in FIG. 5. In the lungs of the control group, the yellow stained portions were evenly seen, and lung metastasis was observed. On the other hand, in the 4Fbenzoyl-TN-14003 administration group, yellow stained specimens were less. Comperatively, the metastasis was inhibited by 4Fbenzoyl-TN-14003.

EXPERIMENTAL EXAMPLE 8

The Inhibitory Activity of 4Fbenzoyl-TN-14003 Against CXCL12-Induced Migration of Human Cell Lines (Jurkat) and Mouse Splenocytes 1. Effects on the Migrating Reaction of Human T-Cell Lines:
RPMI-1640 and fetal calf serum (FCS) was purchased from BioWhittaker, penicillin-streptomycin solution, RPMI-1640 (without phenol red) and HEPES from Invitrogen, BSA from Sigma, and, human SDF-1α (CXCL12) from Genzyme. Jurkat human T lymphocyte cell lines were purchased from ATCC and incubated in RPMI-1640 10% FCS. 4Fbenzoyl-TN14003 was dissolved to PBS and used for experiments.

Using 24-wells Transwell (Costar, polycarbonate membrane, pore size 5 μm), migrating reaction was performed. 600 μL of SDF-1α (final concentration 1 ng/mL) was added to the lower layer of Transwell, $5 \times 10^5$ cells (200 mL) was added to the insert, and was reacted at 37° C. for 4 hours. The cells were pre-incubated with drugs at 37° C. for 30 minutes. The migrating reaction was made in RPMI-1640 culture media containing 20 mmol/L HEPES, 0.5% BSA. The cells migrated to the lower layer were recovered, and the number of the cells was counted by Coulter Counter. The inhibitory rate (%) against the migration by the drug of each concentration was calculated by the following formula, and $IC_{50}$ value was calculated from such inhibitory rate.

$$\text{inhibition rate}(\%) = 100 \times \left(1 - \frac{\begin{pmatrix}\text{the number of migrated cells} \\ \text{at the presence of a drug} \\ \text{of each concentration}\end{pmatrix} - \begin{pmatrix}\text{the number of migrated} \\ \text{cells without } SDF - 1\alpha\end{pmatrix}}{\text{the number of migrated} \atop \text{cells without a drug} - \text{the number of migrated} \atop \text{cells without } SDF - 1\alpha}\right)$$

Figure 6:
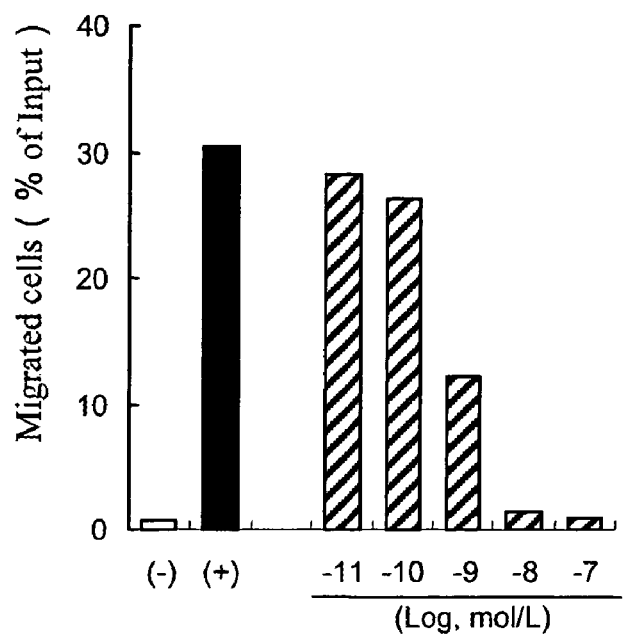
FIG. 6 shows the inhibitory activity of 4Fbenzoyl-TN-14003 against migration of Jurkat cells induced by SDF-1α (CXCL12). The vertical axis shows cell migration (the ratio of migrating cells to the input). From the left, it shows the result obtained respectively when SDF-1α was not added, when SDF-1α was added, when SDF-1α and 4Fbenzoyl-TN-14003 10 pM were added, when SDF-1α and 4Fbenzoyl-TN-14003 100 pM were added, when SDF-1α and 4Fbenzoyl-TN-14003 1 nM were added, when SDF-1α and 4Fbenzoyl-TN-14003 10 nM were added, and when SDF-1α and 4Fbenzoyl-TN-14003 100 nM were added.

As a result, as indicated in FIG. 6, Jurkat cells exhibited strong cell migration reactivity against SDF-1α. 4F-benzoyl-TN14003 inhibited this reaction in a dose-dependent manner, and its $IC_{50}$ value was 0.65 nmol/L.

2. Effects on the Migrating Reaction of Mouse Splenocytes:
Spleens were isolated from BALB/c mice (male, Charles River Japan, Inc.), converted to single cell suspensions, and splenocytes were prepared by crushing red blood cells.

SDF-1α (Peprotech, final concentration 100 ng/mL) was added to the lower layer of Transwell (pore size 5 μm), $1 \times 10^6$/well of the cells (100 μL) were added to the insert, and reacted at 37° C. for 2.5 hours. The cells were incubated with the drug at 37° C. for 30 minutes. Migrating reaction was made in RPMI-1640 culture media containing 20 mmol/L HEPES, 0.5% BSA. The number of the cells migrated to the lower layer was counted by Coulter Counter. Similarly to the preceding clause, the inhibitory rate against the migration by the drug of each concentration and $IC_{50}$ value were calculated.

Figure 7:
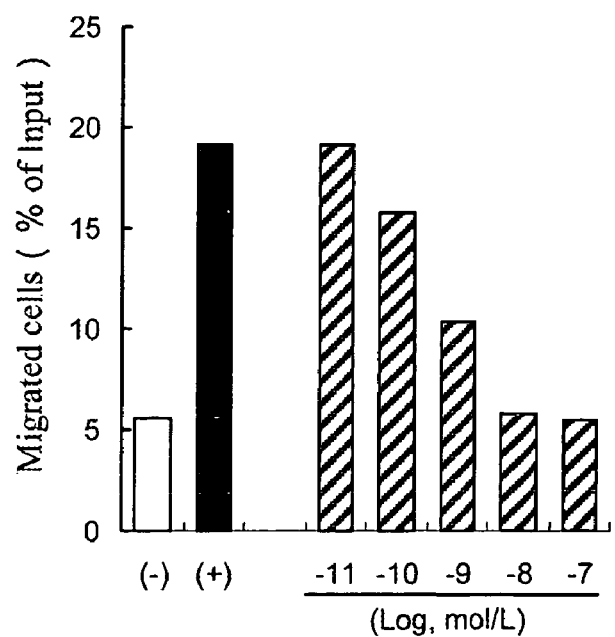
FIG. 7 shows the inhibitory activity of 4Fbenzoyl-TN-14003 against migration of mouse splenocytes induced by SDF-1α (CXCL12). The vertical axis shows cell migration (the ratio of migrating cells to the input). From the left, it shows the result obtained respectively when SDF-1α was not added, when SDF-1α was added, when SDF-1α and 4Fbenzoyl-TN-14003 10 pM were added, when SDF-1α and 4Fbenzoyl-TN-14003 100 pM were added, when SDF-1α and 4Fbenzoyl-TN-14003 1 nM were added, when SDF-1α and 4Fbenzoyl-TN-14003 10 nM were added, and when SDF-1α and 4Fbenzoyl-TN-14003 100 nM were added.

As a result, as indicated in FIG. 7, 4Fbenzoyl-TN14003 inhibited strong migration reactivity of mouse splenocytes induced by SDF-1 in a dose-dependent manner. Its $IC_{50}$ value was 0.54 mmol/L, and it exhibited inhibitory activity comparable to the case of human cells. This means in turn that little species difference was identified between humans and mice with respect to this peptide.

EXPERIMENTAL EXAMPLE 9

Effects of 4Fbenzoyl-TN-14003 on Mouse Delayed-Type Hypersensitivity Reaction (DTH)

Preserved blood of sheep was purchased from Nippon Bio-Supp. Center. The preserved sheep blood was cleansed twice in physiological saline solution, suspended in physiological saline solution, and used as sheep red blood cells (SRBC). As OD541 nm value of oxyhemoglobin at the time of hemolyzation of $1.0 \times 10^9$ cells/mL of the SRBC suspension by 14 parts distilled water is considered to be nearly 0.700, SRBC density was accordingly fixed.

$2 \times 10^7$ cells/50 μl of SRBC were administered subcutaneously to the ankles of the left hindlimbs of BALB/c mice (male, 6 week-old, Charles River Japan, Inc.) and sentisized. After 5 days, $10^8$ cells/50 μl of SRBC were administered subcutaneously to the ankles of the right hindlimbs and DTH reaction was induced. Immediately prior to and 24 hours after the induction of antigens, the thickness of the ankles of the right hindlimbs was measured by a digital micrometer (Mitutoyo Corporation CD-15B), and the increase (mm) in the thickness of ankles was adopted as the indicator of DTH reaction.

4Fbenzoyl-TN14003 was dissolved to PBS, and continuously administered using Alzet osmotic pumps (Alza, 0.5 μL/hr, 7 days persistent type). The osmotic pumps were implanted intradermally to the backs under ether anesthesia on the day before the sensitization. As the control, pumps injected with PBS were similarly implanted. 4F-benzoyl-TN14003 was administered at the doses of 4.8, 24 and 120 μg/day.

Data were expressed as mean value±standard margin of error (n=7). By Williams test, p 0.025 was valued as significant.

Figure 8:
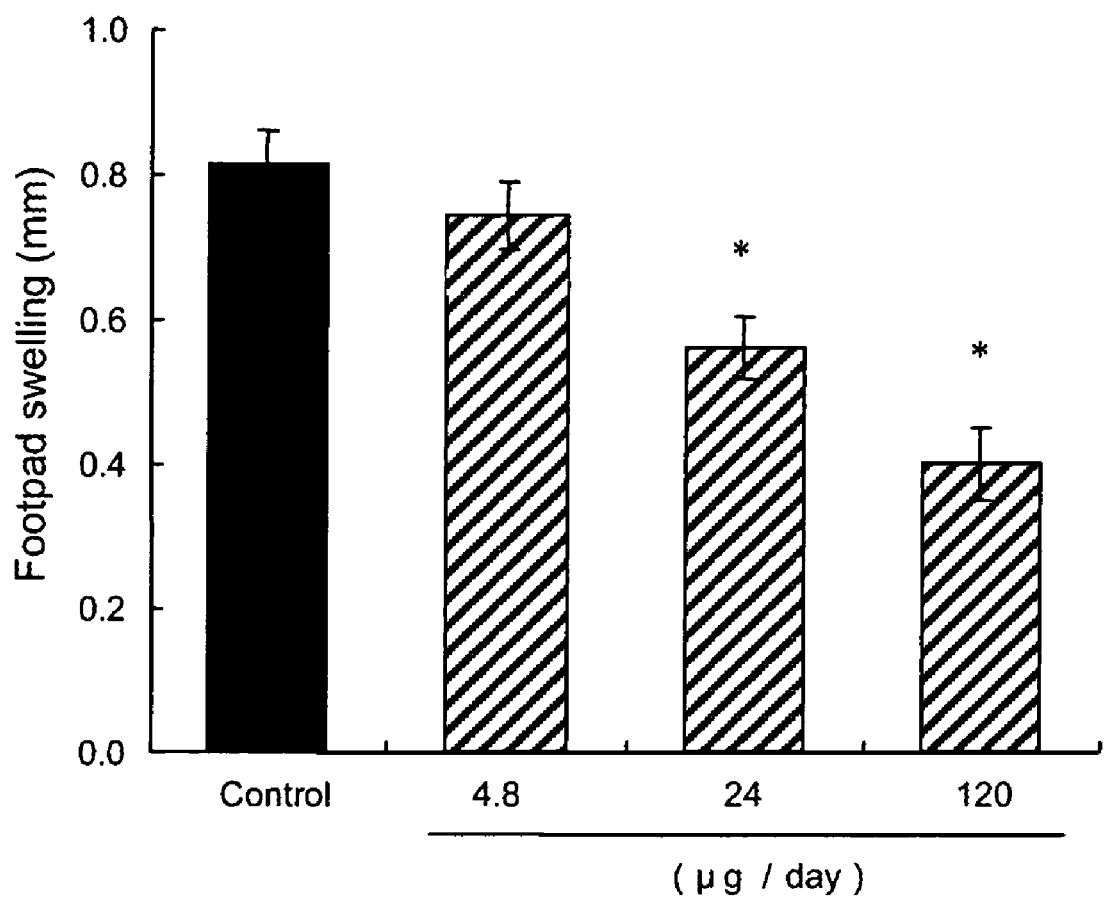
FIG. 8 shows the inhibitory activity of 4Fbenzoyl-TN-14003 against mouse DTH reaction induced by SRBC. The vertical axis shows the increase of footpad thickness of by swelling (mean value±standard margin of error, n=7). From the left, it shows the result each of PBS administration (control) group, 4Fbenzoyl-TN-14003 48 μg per-day administration group, 4Fbenzoyl-TN-14003 24 μg per-day administration group, and 4Fbenzoyl-TN-14003 120 μg per-day administration group. * is P 0.025 (comparison with PBS administration group; Williams' test).

As a result, as indicated in FIG. 8, 4F-benzoyl-TN14003 (4.8, 24 and 120 μg/day) inhibited footpad edema dose-dependently and significantly, and the inhibitory rates were 9, 31 and 51%, respectively. This suggests that CXCR4 plays an important role in cellular immunity such as DTH reaction.

EXPERIMENTAL EXAMPLE 10

Therapeutic Effects of 4Fbenzoyl-TN-14003 on Mouse Collagen-induced Arthritis

FK-506 was purified by a known method (Kino T. et al., J. Antibiot., 1987 40(9): 1249-55). Methotrexate was purchased from Wako Pure Chemical Ind., indomethacin from Sigma, bovine type II collagen from Collagen Research Center (Tokyo, Japan), Freund's complete adjuvant (FCA from Difco), and anti-mouse IgG2a antibody from Zymed, respectively.

Bovine type II collagen was dissolved to the 2 mg/mL concentration by 0.05 mol/L of acetic acid solution, emulsion was prepared with an equal volume of FCA. 50 μL of the emulsion was injected intradermally at the base of the tail DBA/1JN mouse (male, 6 week old, Charles River Japan, Inc.) and sensitized. 21 days after the injection, additional immunization was made similarly. For 2 weeks after the additional immunization, body weights and hindlimb thickness were measured and arthritis scoring was made. Arthritis scores were scored at 0-3 points of each limb, and evaluated by the total of the same (12 points being the full points; 0, normal; 1, mild swelling or swelling of a single digit; 2, moderate swelling or swelling of plural digits; 3, severe swelling). Two weeks after the immunization, four limbs and sera were picked.

After coat blocking bovine type II collagen (10 µg/mL PBS solution) on the immunoplate, 100 µL of 1000 times diluted mouse serum was added, and kept at room temperature for 2 hours. After cleansing, anti-mouse IgG2a antibody (1000 times dilution) was added. After cleansing, TMB was added, kept at room temperature for 30 minutes, $H_2SO_4$ of equal amount was added, and A450 nm was measured.

Indomethacin (1 mg/kg), methotrexate (3 mg/kg) and FK-506 (10 mg/kg) were suspended to 0.5% methyl cellulose, and orally administered every day for 2 weeks from the day of the additional immunization at the dose of 0.1 mL/10 g body weight. 0.5% methyl cellulose solution of the equal dose was orally administered to the control group. 4Fbenzoyl-TN14003 was dissolved to PBS, and continuously administered using Alzet osmotic pumps (Alza, 0.5 µL/hr 2 weeks). The osmotic pumps were implanted intradermally to the backs of the mice under ether anesthesia on the day before the additional immunization. As the control, pumps injected with PBS were similarly implanted. Evaluation of each drug was made for the value obtained 2 weeks after the additional immunization.

Data were expressed as mean value±standard margin of error (n=8-12). Comparison between 2 groups was made by Student's t-test, p 0.05 was valued as significant. Multiple comparison was made by Dunnett test, p 0.05 was valued as significant.

Figure 9:
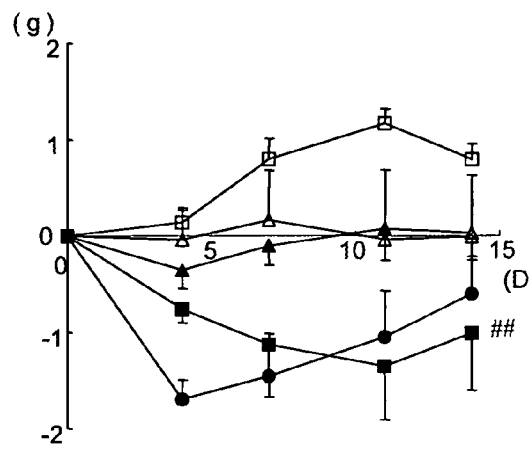
FIG. 9 shows the effects of known medicines against mouse collagen arthritis.
Figure 9:
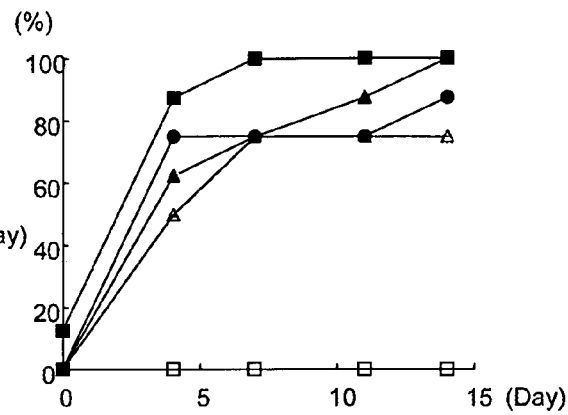
Figure 9:
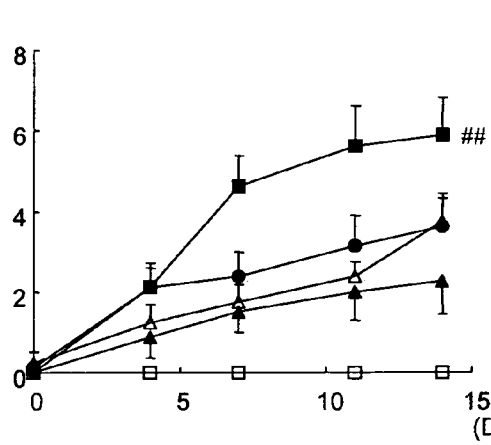
Figure 9:
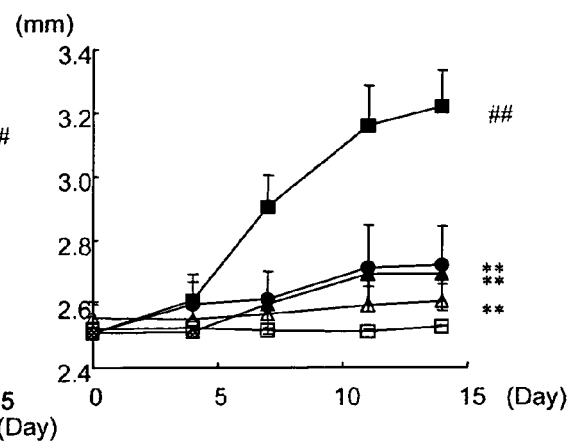
Figure 9:
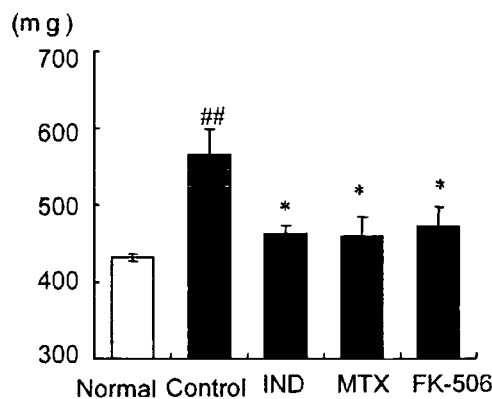
Figure 9:
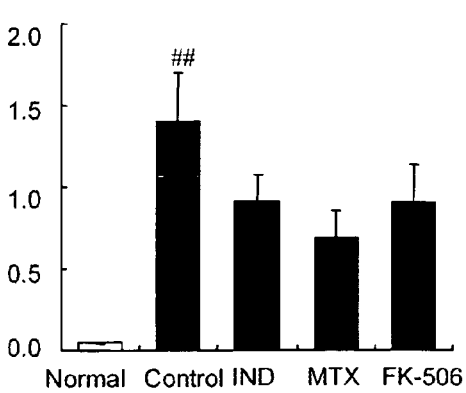
Figure 10A:
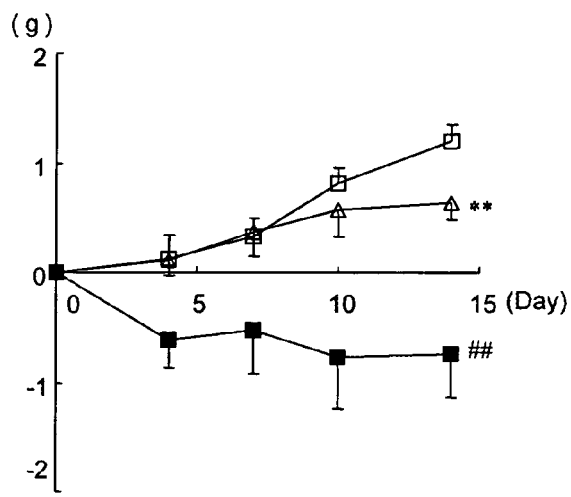
FIG. 10A shows fluctuations of the body weight [vertical axis: body weight (g) (mean value±standard margin of error), horizontal axis: post-booster days]
Figure 10B:
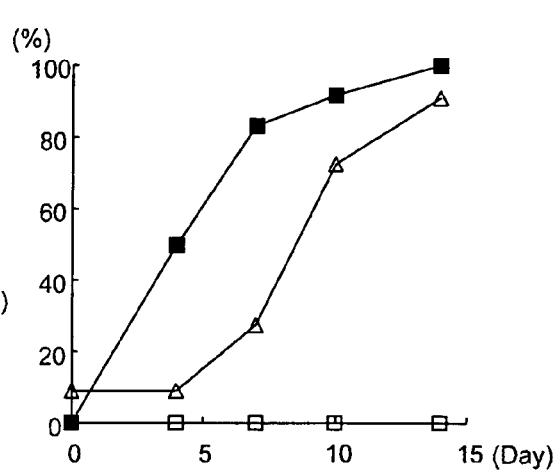
FIG. 10B shows fluctuations of the disease incidence [vertical axis: incidence (%), horizontal axis: post-booster days]
Figure 10C:
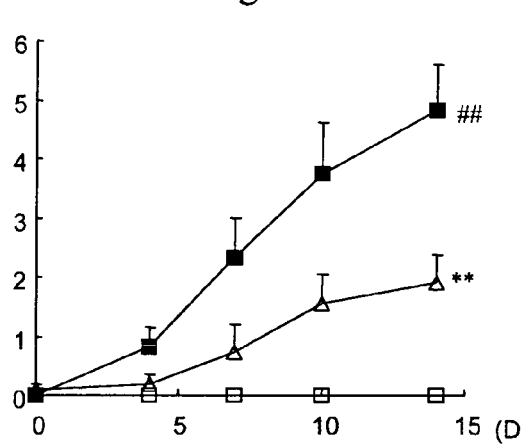
FIG. 10C shows fluctuations of arthritis score [vertical axis: arthritis score (mean value±standard margin of error), horizontal axis: post-booster days]
Figure 10D:
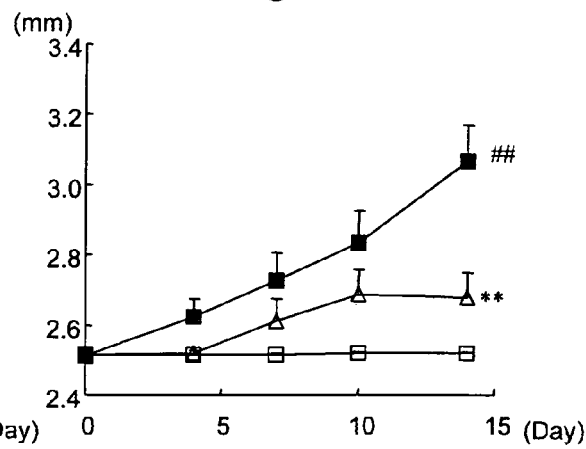
FIG. 10D shows the fluctuations of ankle thickness [vertical axis: ankle thickness (mm) (mean value±standard margin of error), horizontal axis: post-booster days]. : normal mice group (n=8), : drug non-administration (control) group (n=12), Δ: 4Fbenzoyl-TN-14003 administration group (n=11)
Figure 10E:
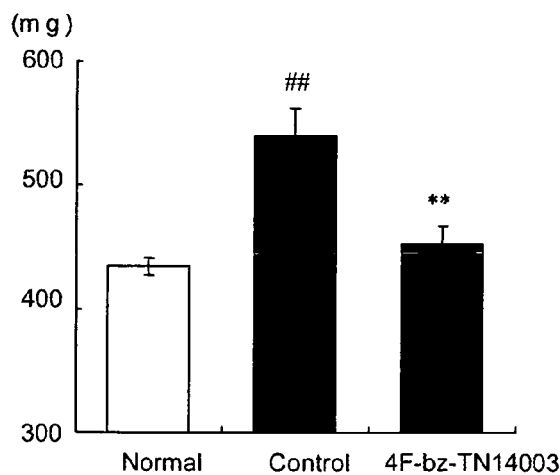
FIG. 10E shows the effects of 4Fbenzoyl-TN-14003 on hindlimb swelling 2 weeks after the booster [vertical axis: hindlimb weight (mg) (mean value±standard margin of error)]
Figure 10F:
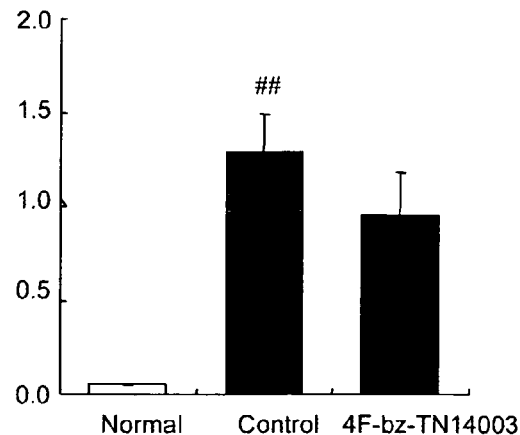
FIG. 10F shows the effects of 4Fbenzoyl-TN-14003 on the anti-bovine II collagen IgG2a antibody value 2 weeks after the booster [vertical axis: antibody value (A450) (mean value±standard margin of error)]. From the left, it shows normal mouse group (n=8), drug non-administration (control) group (n=12), 4Fbenzoyl-TN-14003 administration group (n=11)]. ## shows P 0.01 (comparison with normal mice group; t-test), and ** shows P 0.01 (comparison with drug non-administration group; t-test).

As a result, all of Indomethacin (1 mg/kg, p.o.), methotrexate (3 mg/kg, p.o.) and FK-506 (10 mg/kg, p.o.) significantly inhibited hindlimb swelling, and exhibited significant or evident inhibitory activity against arthritis score (FIG. 9).

4F-benzoyl-TN14003 (120 µg/day) exhibited significant inhibitory activity against hindlimb swelling, arthritis score and body weight loss. It also showed an inhibitory tendency against increase of anti-type II collagen specific IgG2a antibody value (FIG. 10). These inhibitory effects were equivalent to or better than those of the above-mentioned known drugs.

INDUSTRIAL APPLICABILITY

The peptidic compounds of the present invention having CXCR4 antagonistic activity can inhibit the interaction of CXCR4 and CXCL12/SDF-1α, and accordingly, can inhibit the migrating reaction of cancerous cells of cancers impressing CXCR4, for example, oral cancer, throat cancer, lip cancer, lingual cancer, gingival cancer, nasopharyngeal cancer, esophageal cancer, gastric cancer, small intestinal cancer, large intestinal cancer including colorectal cancer, liver cancer, gallbladder cancer, pancreatic cancer, nasal cancer, lung cancer, bone cancer, soft tissue cancer, skin cancer, melanoma, breast cancer, uterine cancer, ovarian cancer, prostate cancer, testicular cancer, penile cancer, bladder cancer, kidney cancer, brain cancer, thyroid cancer, lymphoma, leukemia, etc., and are useful as drugs for the prevention and/or therapy of these cancers. Also, the peptidic compounds of the present invention can inhibit the migrating reaction of immunocytes induced by CXCL12/SDF-1α and are useful as drugs for the prevention and/or therapy of chronic rheumatoid arthritis.

SEQUENCE LISTING

```
<160> NUMBER OF SEQ ID NOS: 68

<210> SEQ ID NO 1
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, ornithine, citrulline, Ala
      or Glu which may be derived at the N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derived at the N-terminal, Xaa
      is Arg or Glu, and when Xaa of (1) is deleted, Xaa is Arg or Glu
      which may be
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
```

```
<223> OTHER INFORMATION: Cys at 4-position and Cys at 13-position may be
      linked by disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg.
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derived at the C-terminal.

<400> SEQUENCE: 1

Xaa Xaa Xaa Cys Tyr Xaa Xaa Xaa Xaa Xaa Xaa Xaa Cys Xaa
1               5                   10

<210> SEQ ID NO 2
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Glu which may be derived at the
      N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Glu which may be derived at
      the N-terminal, Xaa is Arg or Glu, and when Xaa of (1) is deleted,
      Xaa is Arg or Glu which may be derived at the N-terminal.
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
<223> OTHER INFORMATION: Cys at 4-position and Cys at 13-position may be
      linked by disulfid bond.
```

```
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline,  Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg.
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is citrulline, Glu, Arg or Lys.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derived at the C-terminal.

<400> SEQUENCE: 2

Xaa Xaa Xaa Cys Tyr Xaa Xaa Xaa Xaa Xaa Xaa Xaa Cys Xaa
 1               5                   10

<210> SEQ ID NO 3
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derived at the N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derived at the N-terminal, Xaa
      is Glu, and when Xaa of (1) is deleted, Xaa is Glu which may be
      derived at the
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
<223> OTHER INFORMATION: Cys at 4-position and Cys at 13-position may be
      linked by disulfid bond.
<220> FEATURE:
<221> NAME/KEY: MISC_FEATURE
```

```
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg.
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is citrulline, Glu, Arg or Lys.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derived at the C-terminal.

<400> SEQUENCE: 3

Xaa Xaa Xaa Cys Tyr Xaa Xaa Xaa Xaa Xaa Xaa Xaa Cys Xaa
1               5                   10

<210> SEQ ID NO 4
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derived at the N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derived at the N-terminal, Xa
      a is Arg or Glu, and when Xaa of (1) is deleted, Xaa is Arg or Gl
      u which may be
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
<223> OTHER INFORMATION: Cys at 4-position and Cys at 13-position may be
      linked by disulfid bond.
<220> FEATURE:
<221> NAME/KEY: MISC_FEATURE
<222> LOCATION: (6)..(6)
<223> OTHER INFORMATION: Xaa is
```

```
                                 -continued

Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg.
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is citrulline, Glu, Arg or Lys.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derived at the C-terminal.

<400> SEQUENCE: 4

Xaa Xaa Xaa Cys Tyr Xaa Xaa Xaa Xaa Xaa Xaa Xaa Cys Xaa
1               5                   10

<210> SEQ ID NO 5
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derived at the N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derived at the N-terminal, Xa
      a is Arg or Glu, and when Xaa of (1) is deleted, Xaa is Arg or Gl
      u which may be
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
<223> OTHER INFORMATION: Cys at 4-position and Cys at 13-position may be
      linked by disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
```

```
<221> NAME/KEY: MISC_FEATURE
<222> LOCATION: (7)..(7)
<223> OTHER INFORMATION: Xaa is Arg or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg.
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is citrulline, Glu, Arg or Lys.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derived at the C-terminal.

<400> SEQUENCE: 5

Xaa Xaa Xaa Cys Tyr Xaa Xaa Xaa Xaa Xaa Xaa Xaa Cys Xaa
1               5                   10

<210> SEQ ID NO 6
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derived at the N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derived at the N-terminal, Xa
      a is Arg or Glu, and when Xaa of (1) is deleted, Xaa is Arg or Gl
      u which may be
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
<223> OTHER INFORMATION: Cys at 4-position and Cys at 13-position may be
      linked by disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
```

```
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORM
      ATION: Xaa is Glu. FEATURE:
<221> NAME/KEY: MISC_FEATURE
<222> LOCATION: (9)..(9)
<223> OTHER INFORMATION: Xaa is Pro, Gly, ornithine, Lys, Ala, citrulline or Arg.

<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline or Glu.
<220> FE
      ATURE:
<221> NAME/KEY: MISC_FEATURE
<222> LOCATION: (11)..(11)
<223> OTHER INFORMATION: Xaa is Arg, Lys, ornithine, citrulline, Ala or Glu.
<220> FEATU
      RE:
<221> NAME/KEY: MISC_FEATURE
<222> LOCATION: (12)..(12)
<223> OTHER INFORMATION: Xaa is citrulline, Glu, Arg or Lys.
<220> FEATURE:
<221> NAME/KEY: MISC_FEATURE
<222> LOCATION: (14)..(14)
<223> OTHER INFORMATION: Xaa is Arg, Glu, Lys or citrulline which may be derived at
      the C-term
<400> SEQUENCE: 6

Xaa Xaa Xaa Cys Tyr Xaa Xaa Xaa Xaa Xaa Xaa Xaa Cys Xaa
1               5                   10

<210> SEQ ID NO 7
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derived at the N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derived at the N-terminal, Xa
      a is Arg or Glu, and when Xaa of (1) is deleted, Xaa is Arg or Gl
      u which may be
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
<223> OTHER INFORMATION: Cys at 4-position and Cys at 13-position may be
      linked by disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
```

```
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg.
<220> FEATURE:
<221> NAME/KEY: MISC_FEATURE
<222> LOCATION: (10)..(10)
<223> OTHER INFORMATION: Xaa i
      s Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is citrulline, Glu, Arg or Lys.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derived at the C-terminal.

<400> SEQUENCE: 7

Xaa Xaa Xaa Cys Tyr Xaa Xaa Xaa Xaa Xaa Xaa Xaa Cys Xaa
1               5                   10

<210> SEQ ID NO 8
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derived at the N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derived at the N-terminal, Xa
      a is Arg or Glu, and when Xaa of (1) is deleted, Xaa is Arg or Gl
      u which may be
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
<223> OTHER INFORMATION: Cys at 4-position and Cys at 13-position may be
      linked by disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
```

-continued

```
        citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
        citrulline or Arg.
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
        or Glu.
<220> FEATURE:
<221> NAME/KEY: MISC_FEATURE
<222> LOCATION: (11)..(11)
<223> OTHER INFORMATION: Xaa is
        Glu.
<220> FEATURE:
<221> NAME/KEY: MISC_FEATURE
<222> LOCATION: (12)..(12)
<223> OTHER INFORMATION: Xaa is citrulline, Glu, Arg or Lys.
<220> FEATURE:
<221> NAME/KEY: MISC_FEATURE
<222> LOCATION: (14)..(14)
<223> OTHER INFORMATION: Xaa is Arg, Glu, Lys or citrulline which may be
        derived at the C-terminal.

<400> SEQUENCE: 8

Xaa Xaa Xaa Cys Tyr Xaa Xaa Xaa Xaa Xaa Xaa Xaa Cys Xaa
1               5                   10

<210> SEQ ID NO 9
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
        Glu which may be derived at the N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
        citrulline, Ala or Glu which may be derived at the N-terminal, Xa
        a is Arg or Glu, and when Xaa of (1) is deleted, Xaa is Arg or Gl
        u which may be
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
<223> OTHER INFORMATION: Cys at 4-position and Cys at 13-position may be
        linked by disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
        Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
        Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
        citrulline, Arg or Glu.
<220> FEATURE:
```

```
<221> NAME/KEY: MISC_FEATURE
<222> LOCATION: (9)..(9)
<223> OTHER INFORMATION: Xaa is Pro, Gly, ornithine, Lys, Ala,
      citrulline or Arg.
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Glu, Arg or Lys.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derived at the C-terminal.

<400> SEQUENCE: 9

Xaa Xaa Xaa Cys Tyr Xaa Xaa Xaa Xaa Xaa Xaa Xaa Cys Xaa
1               5                   10

<210> SEQ ID NO 10
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derived at the N-terminal, or is deleted.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derived at the N-terminal, Xa
      a is Arg or Glu, and when Xaa of (1) is deleted, Xaa is Arg or Gl
      u which may be
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: MISC_FEATURE
<222> LOCATION: (4)..(13)
<223> OTHER INFORMATION: Cys at 4-position and Cys at 13-position may be
      linked by disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
```

```
<223> OTHER INFORMATION: Xaa is Pro, Gly, ornithine, Lys, Ala,
      citrulline or Arg.
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is citrulline, Glu, Arg or Lys.
<220> FEATURE:
<221> NAME/KEY: MISC_FEATURE
<222> LOCATION: (14)..(14)
<223> OTHER INFORMATION: Xaa is Glu, Lys or citrulline which may be deri
      ved at the C-terminal.

<400> SEQUENCE: 10

Xaa Xaa Xaa Cys Tyr Xaa Xaa Xaa Xaa Xaa Xaa Xaa Cys Xaa
1               5                   10

<210> SEQ ID NO 11
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is Dlys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 11

Xaa Arg Arg Xaa Cys Tyr Xaa Lys Xaa Pro Tyr Arg Xaa Cys Arg Xaa
1               5                   10                  15

<210> SEQ ID NO 12
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (4)..(4)
<223> OTHER INFORMATION: Xaa is Nal
```

```
<220> FEATURE:
<221> NAME/KEY: MISC_FEATURE
<222> LOCATION: (9)..(9)
<223> OTHER INFORMATION: Xaa is DCit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 12

Xaa Arg Arg Xaa Cys Tyr Arg Lys Xaa Pro Tyr Arg Xaa Cys Arg Xaa
1               5                   10                  15

<210> SEQ ID NO 13
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DCit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 13

Xaa Arg Arg Xaa Cys Tyr Xaa Lys Xaa Pro Tyr Arg Xaa Cys Arg Xaa
1               5                   10                  15

<210> SEQ ID NO 14
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is Dlys
<220> FEATURE:
```

<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 14

Xaa Arg Arg Xaa Cys Tyr Xaa Lys Xaa Pro Tyr Xaa Xaa Cys Arg Xaa
1               5                   10                  15

<210> SEQ ID NO 15
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (2)..(2)
<223> OTHER INFORMATION: Xaa is Cit
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is Dlys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 15

Xaa Xaa Arg Xaa Cys Tyr Xaa Lys Xaa Pro Tyr Arg Xaa Cys Arg Xaa
1               5                   10                  15

<210> SEQ ID NO 16
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (2)..(2)
<223> OTHER INFORMATION: Xaa is Cit
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE

```
<222> LOCATION: (9)..(9)
<223> OTHER INFORMATION: Xaa is DCit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 16

Xaa Xaa Arg Xaa Cys Tyr Arg Lys Xaa Pro Tyr Arg Xaa Cys Arg Xaa
1               5                   10                  15

<210> SEQ ID NO 17
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DCit
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 17

Xaa Arg Arg Xaa Cys Tyr Arg Lys Xaa Pro Tyr Xaa Xaa Cys Arg Xaa
1               5                   10                  15

<210> SEQ ID NO 18
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (2)..(2)
<223> OTHER INFORMATION: Xaa is Cit
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DCit
<220> FEATURE:
<221> NAME/KEY: MISC_FEATURE
<222> LOCATION: (12)..(12)
```

<223> OTHER INFORMATION: Xaa is Cit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 18

Xaa Xaa Arg Xaa Cys Tyr Arg Lys Xaa Pro Tyr Xaa Xaa Cys Arg Xaa
1               5                   10                  15

<210> SEQ ID NO 19
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DCit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 19

Xaa Arg Arg Xaa Cys Tyr Xaa Lys Xaa Pro Tyr Arg Xaa Cys Arg Xaa
1               5                   10                  15

<210> SEQ ID NO 20
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is Dlys
<220> FEATURE:
<221> NAME/KEY: MISC_FEATURE
<222> LOCATION: (12)..(12)
<223> OTHER INFORMATION: Xaa is Cit

```
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 20

Xaa Arg Arg Xaa Cys Tyr Xaa Lys Xaa Pro Tyr Xaa Xaa Cys Arg Xaa
1               5                   10                  15

<210> SEQ ID NO 21
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (2)..(2)
<223> OTHER INFORMATION: Xaa is Cit
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is Dlys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 21

Xaa Xaa Arg Xaa Cys Tyr Xaa Lys Xaa Pro Tyr Arg Xaa Cys Arg Xaa
1               5                   10                  15

<210> SEQ ID NO 22
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (2)..(2)
<223> OTHER INFORMATION: Xaa is Cit
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DCit
<220> FEATURE:
```

```
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 22

Xaa Xaa Arg Xaa Cys Tyr Arg Lys Xaa Pro Tyr Arg Xaa Cys Arg Xaa
1               5                   10                  15

<210> SEQ ID NO 23
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DCit
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 23

Xaa Arg Arg Xaa Cys Tyr Arg Lys Xaa Pro Tyr Xaa Xaa Cys Arg Xaa
1               5                   10                  15

<210> SEQ ID NO 24
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (2)..(2)
<223> OTHER INFORMATION: Xaa is Cit
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
```

```
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 24

Xaa Xaa Arg Xaa Cys Tyr Arg Lys Xaa Pro Tyr Xaa Xaa Cys Arg Xaa
1               5                   10                  15

<210> SEQ ID NO 25
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (2)..(2)
<223> OTHER INFORMATION: Xaa is DGlu
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 25

Xaa Xaa Arg Xaa Cys Tyr Arg Lys Xaa Pro Tyr Arg Xaa Cys Arg Xaa
1               5                   10                  15

<210> SEQ ID NO 26
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 26
```

Xaa Arg Glu Xaa Cys Tyr Arg Lys Xaa Pro Tyr Arg Xaa Cys Arg Xaa
1               5                   10                  15

<210> SEQ ID NO 27
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 27

Xaa Arg Arg Xaa Cys Tyr Glu Lys Xaa Pro Tyr Arg Xaa Cys Arg Xaa
1               5                   10                  15

<210> SEQ ID NO 28
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 28

Xaa Arg Arg Xaa Cys Tyr Arg Glu Xaa Pro Tyr Arg Xaa Cys Arg Xaa
1               5                   10                  15

<210> SEQ ID NO 29
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)

<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (8)..(8)
<223> OTHER INFORMATION: Xaa is DGlu
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 29

Xaa Arg Arg Xaa Cys Tyr Arg Lys Xaa Pro Tyr Arg Xaa Cys Arg Xaa
1               5                   10                  15

<210> SEQ ID NO 30
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 30

Xaa Arg Arg Xaa Cys Tyr Arg Lys Xaa Pro Tyr Glu Xaa Cys Arg Xaa
1               5                   10                  15

<210> SEQ ID NO 31
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DLys

```
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 31

Xaa Arg Arg Xaa Cys Tyr Arg Lys Xaa Pro Tyr Arg Xaa Cys Glu Xaa
1               5                   10                  15

<210> SEQ ID NO 32
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH
<220> FEATURE:
<221> NAME/KEY: MISC_FEATURE
<222> LOCATION: (16)..(16)
<223> OTHER INFORMATION: Xaa is NH2

<400> SEQUENCE: 32

Xaa Arg Arg Xaa Cys Tyr Xaa Lys Xaa Pro Tyr Arg Xaa Cys Arg Xaa
1               5                   10                  15

<210> SEQ ID NO 33
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is DGlu
<220> FEATURE:
<221> NAME/KEY: MISC_FEATURE
<222> LOCATION: (9)..(9)
<223> OTHER INFORMATION: Xaa is DCit
<220> FEATURE:
```

```
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH
<220> FEATURE:
<221> NAME/KEY: MISC_FEATURE
<222> LOCATION: (16)..(16)
<223> OTHER INFORMATION: Xaa is NH2

<400> SEQUENCE: 33

Xaa Arg Arg Xaa Cys Tyr Xaa Lys Xaa Pro Tyr Arg Xaa Cys Arg Xaa
1               5                   10                  15

<210> SEQ ID NO 34
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is DGlu
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 34

Xaa Arg Arg Xaa Cys Tyr Xaa Lys Xaa Pro Tyr Arg Xaa Cys Arg Xaa
1               5                   10                  15

<210> SEQ ID NO 35
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (2)..(2)
<223> OTHER INFORMATION: Xaa is DGlu
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
```

```
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 35

Xaa Xaa Arg Xaa Cys Tyr Xaa Lys Xaa Pro Tyr Arg Xaa Cys Arg Xaa
1               5                   10                  15

<210> SEQ ID NO 36
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (11)..(11)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 36

Xaa Arg Arg Xaa Cys Tyr Xaa Lys Xaa Pro Xaa Arg Xaa Cys Arg Xaa
1               5                   10                  15

<210> SEQ ID NO 37
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
```

```
<223> OTHER INFORMATION: Xaa is DGlu
<220> FEATURE:
<221> NAME/KEY: MISC_FEATURE
<222> LOCATION: (13)

```
<220> FEATURE:
<221> NAME/KEY: MISC_FEATURE
<222> LOCATION: (11)..(11)
<223> OTHER INFORMATION: X

<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 41

Xaa Arg Arg Xaa Cys Tyr Xaa Lys Xaa Pro Tyr Arg Xaa Cys Arg Xaa
1               5                   10                  15

<210> SEQ ID NO 42
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is guanyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 42

Xaa Arg Arg Xaa Cys Tyr Xaa Lys Xaa Pro Tyr Arg Xaa Cys Arg Xaa
1               5                   10                  15

<210> SEQ ID NO 43
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is TMguanyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE

```
<222> LOCATION: (16)..(16)
<223> OTHER INFORMATION: Xaa is NH2

<400> SEQUENCE: 43

Xaa Arg Arg Xaa Cys Tyr Xaa Lys Xaa Pro Tyr Arg Xaa Cys Arg Xaa
1               5                   10                  15

<210> SEQ ID NO 44
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is TMguanyl
<220> FEATURE:
<221> NAME/KEY: MISC_FEATURE
<222> LOCATION: (3)..(3)
<223> OTHER INFORMATION: Xaa is Nal
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (8)..(8)
<223> OTHER INFORMATION: Xaa is DGlu
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (15)..(15)
<223> OTHER INFORMATION: Xaa is NH2

<400> SEQUENCE: 44

Xaa Arg Xaa Cys Tyr Xaa Lys Xaa Pro Tyr Arg Xaa Cys Arg Xaa
1               5                   10                  15

<210> SEQ ID NO 45
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 4F-benzoyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 45
```

Xaa Arg Arg Xaa Cys Tyr Xaa Lys Xaa Pro Tyr Arg Xaa Cys Arg Xaa
1               5                   10                  15

<210> SEQ ID NO 46
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 2F-benzoyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 46

Xaa Arg Arg Xaa Cys Tyr Xaa Lys Xaa Pro Tyr Arg Xaa Cys Arg Xaa
1               5                   10                  15

<210> SEQ ID NO 47
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is APA
<220> FEATURE:
<221> NAME/KEY: MISC_FEATURE
<222> LOCATION: (3)..(3)
<223> OTHER INFORMATION: Xaa is Nal
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (8)..(8)
<223> OTHER INFORMATION: Xaa is DGlu
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (15)..(15)
<223> OTHER INFORMATION: Xaa is NH2

<400> SEQUENCE: 47

Xaa Arg Xaa Cys Tyr Xaa Lys Xaa Pro Tyr Arg Xaa Cys Arg Xaa
1               5                   10                  15

<210> SEQ ID NO 48

```
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is desamino-R
<220> FEATURE:
<221> NAME/KEY: MISC_FEATURE
<222> LOCATION: (3)..(3)
<223> OTHER INFORMATION: Xaa is Nal
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (8)..(8)
<223> OTHER INFORMATION: Xaa is DGlu
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (15)..(15)
<223> OTHER INFORMATION: Xaa is NH2

<400> SEQUENCE: 48

Xaa Arg Xaa Cys Tyr Xaa Lys Xaa Pro Tyr Arg Xaa Cys Arg Xaa
1               5                   10                  15

<210> SEQ ID NO 49
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is guanyl
<220> FEATURE:
<221> NAME/KEY: MISC_FEATURE
<222> LOCATION: (3)..(3)
<223> OTHER INFORMATION: Xaa is Nal
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (8)..(8)
<223> OTHER INFORMATION: Xaa is DGlu
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (15)..(15)
<223> OTHER INFORMATION: Xaa is NH2

<400> SEQUENCE: 49

Xaa Arg Xaa Cys Tyr Xaa Lys Xaa Pro Tyr Arg Xaa Cys Arg Xaa
1               5                   10                  15

<210> SEQ ID NO 50
<211> LENGTH: 15
<212> TYPE: PRT
<213> ORGANISM: Artificial
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: Xaa is succinyl
<220> FEATURE:
<221> NAME/KEY: MISC_FEATURE
<222> LOCATION: (3)..(3)
<223> OTHER INFORMATION: Xaa is Nal
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (8)..(8)
<223> OTHER INFORMATION: Xaa is DGlu
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (15)..(15)
<223> OTHER INFORMATION: Xaa is NH2

<400> SEQUENCE: 50

Xaa Arg Xaa Cys Tyr Xaa Lys Xaa Pro Tyr Arg Xaa Cys Arg Xaa
1               5                   10                  15

<210> SEQ ID NO 51
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaryl
<220> FEATURE:
<221> NAME/KEY: MISC_FEATURE
<222> LOCATION: (3)..(3)
<223> OTHER INFORMATION: Xaa is Nal
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (8)..(8)
<223> OTHER INFORMATION: Xaa is DGlu
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (15)..(15)
<223> OTHER INFORMATION: Xaa is NH2

<400> SEQUENCE: 51

Xaa Arg Xaa Cys Tyr Xaa Lys Xaa Pro Tyr Arg Xaa Cys Arg Xaa
1               5                   10                  15

<210> SEQ ID NO 52
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is deaminoTMG
<220> FEATURE:
```

-continued

```
<221> NAME/KEY: MISC_FEATURE
<222> LOCATION: (2)..(2)
<223> OTHER INFORMATION: Xaa is APA
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 52

Xaa Xaa Arg Xaa Cys Tyr Xaa Lys Xaa Pro Tyr Arg Xaa Cys Arg Xaa
1               5                   10                  15

<210> SEQ ID NO 53
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is nelfinaviryl
<220> FEATURE:
<221> NAME/KEY: MISC_FEATURE
<222> LOCATION: (2)..(2)
<223> OTHER INFORMATION: Xaa is succinyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 53

Xaa Xaa Arg Xaa Cys Tyr Xaa Lys Xaa Pro Tyr Arg Xaa Cys Arg Xaa
1               5                   10                  15

<210> SEQ ID NO 54
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: Xaa is AZT
<220> FEATURE:
<221> NAME/KEY: MISC_FEATURE
<222> LOCATION: (2)..(2)
<223> OTHER INFORMATION: Xaa is glutaryl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 54

Xaa Xaa Arg Xaa Cys Tyr Xaa Lys Xaa Pro Tyr Arg Xaa Cys Arg Xaa
1               5                   10                  15

<210> SEQ ID NO 55
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is R-CH2
<220> FEATURE:
<221> NAME/KEY: MISC_FEATURE
<222> LOCATION: (3)..(3)
<223> OTHER INFORMATION: Xaa is Nal
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (8)..(8)
<223> OTHER INFORMATION: Xaa is DGlu
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (15)..(15)
<223> OTHER INFORMATION: Xaa is NH2

<400> SEQUENCE: 55

Xaa Arg Xaa Cys Tyr Xaa Lys Xaa Pro Tyr Arg Xaa Cys Arg Xaa
1               5                   10                  15

<210> SEQ ID NO 56
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: Xaa is H
<220> FEATURE:
<221> NAME/KEY: MISC_FEATURE
<222> LOCATION: (3)..(3)
<223> OTHER INFORMATION: Xaa is Nal
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (8)..(8)
<223> OTHER INFORMATION: Xaa is DGlu
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (15)..(15)
<223> OTHER INFORMATION: Xaa is NH2

<400> SEQUENCE: 56

Xaa Arg Xaa Cys Tyr Xaa Lys Xaa Pro Tyr Arg Xaa Cys Arg Xaa
1               5                   10                  15

<210> SEQ ID NO 57
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is TMguanyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DCit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 57

Xaa Arg Arg Xaa Cys Tyr Xaa Lys Xaa Pro Tyr Arg Xaa Cys Arg Xaa
1               5                   10                  15

<210> SEQ ID NO 58
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is ACA
<220> FEATURE:
<221> NAME/KEY: MISC_FEATURE
<222> LOCATION: (4)..(4)
<223> OTHER INFORMATION: Xaa is Nal
```

```
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DCit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 58

Xaa Arg Arg Xaa Cys Tyr Xaa Lys Xaa Pro Tyr Arg Xaa Cys Arg Xaa
1               5                   10                  15

<210> SEQ ID NO 59
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is ACA
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is OH

<400> SEQUENCE: 59

Xaa Arg Arg Xaa Cys Tyr Arg Lys Xaa Pro Tyr Arg Xaa Cys Arg Xaa
1               5                   10                  15

<210> SEQ ID NO 60
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DLys
<220> FEATURE:
```

<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 60

Xaa Arg Arg Xaa Cys Tyr Xaa Arg Xaa Pro Tyr Arg Xaa Cys Arg Xaa
1               5                   10                  15

<210> SEQ ID NO 61
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is AC
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 61

Xaa Arg Arg Xaa Cys Tyr Xaa Arg Xaa Pro Tyr Arg Xaa Cys Arg Xaa
1               5                   10                  15

<210> SEQ ID NO 62
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is AC
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 62

Xaa Arg Arg Xaa Cys Tyr Xaa Lys Xaa Pro Tyr Arg Xaa Cys Arg Xaa
1               5                   10                  15

<210> SEQ ID NO 63
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is AC
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (9)..(9)
<223> OTHER INFORMATION: Xaa is DCit
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 63

Xaa Arg Arg Xaa Cys Tyr Arg Lys Xaa Pro Tyr Arg Xaa Cys Arg Xaa
1               5                   10                  15

<210> SEQ ID NO 64
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 4F-benzoyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DLys
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NH2

<400> SEQUENCE: 64

Xaa Arg Arg Xaa Cys Tyr Xaa Lys Xaa Pro Tyr Arg Xaa Cys Arg Xaa
1               5                   10                  15

```
<210> SEQ ID NO 65
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 4F-benzoyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NHMe

<400> SEQUENCE: 65

Xaa Arg Arg Xaa Cys Tyr Xaa Lys Xaa Pro Tyr Arg Xaa Cys Arg Xaa
1               5                  10                  15

<210> SEQ ID NO 66
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 4F-benzoyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NHEt

<400> SEQUENCE: 66

Xaa Arg Arg Xaa Cys Tyr Xaa Lys Xaa Pro Tyr Arg Xaa Cys Arg Xaa
1               5                  10                  15

<210> SEQ ID NO 67
<211> LENGTH: 16
<212> TYPE: PRT
<213> ORGANISM: Artificial
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: Xaa is 4F-benzoyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is NhiPr

<400> SEQUENCE: 67

Xaa Arg Arg Xaa Cys Tyr Xaa Lys Xaa Pro Tyr Arg Xaa Cys Arg Xaa
1               5                   10                  15

<210> SEQ ID NO 68
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 4F-benzoyl
<220> FEATURE:
<221> NAME/KEY: MISC_FEATURE
<222> LOCATION: (4)..(4)
<223> OTHER INFORMATION: Xaa is Nal
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is DGlu
<220> FEATURE:
<221> NAME/KEY: MISC_FEATURE
<222> LOCATION: (13)..(13)
<223> OTHER INFORMATION: Xaa is Cit
<220> FEATURE:
<221> NAME/KEY: MISC_FEATURE
<222> LOCATION: (16)..(16)
<223> OTHER INFORMATION: Xaa is tyramine

<400> SEQUENCE: 68

Xaa Arg Arg Xaa Cys Tyr Xaa Lys Xaa Pro Tyr Arg Xaa Cys Arg Xaa
1               5                   10                  15
```

The invention claimed is:

1. A peptide according to formula (I) Arg-Arg-Xaa$_1$-Cys-Tyr-Xaa$_2$-Lys-Xaa$_3$-Pro-Tyr-Arg-Xaa$_4$-Cys-Arg (I) (SEQ ID NO:64) or a salt thereof, wherein:
 (a) each amino acid may be a D- or L-amino acid
 (b) Xaa$_1$ is naphthylalanine;
 (c) Xaa$_2$ and Xaa$_4$ are citrulline;
 (d) Xaa$_3$ is Lys or D-Lys; and
 (e) the Arg at position 1 is derivatized at the N-terminus with a substituted benzoyl group selected from the group consisting of 2-fluorobenzoyl, 3-fluorobenzoyl, 4-fluorobenzoyl, 2-bromobenzoyl, 3-bromobenzoyl, 4-bromobenzoyl, 2-nitrobenzoyl, 3-nitrobenzoyl and 4-nitrobenzoyl.

2. The peptide or salt of claim 1 wherein the substituted benzoyl group is a 4-fluorobenzoyl or 2-fluorobenzoyl group.

3. The peptide or salt of claim 2 wherein the substituted benzoyl group is a 4-fluorobenzoyl group.

4. The peptide or salt of claim 1, wherein the Arg at position 14 is C-terminally amidated and $Xaa_3$ at position 8 is D-Lys.

5. The peptide or salt of claim 2, wherein the Arg at position 14 is C-terminally amidated and $Xaa_3$ at position 8 is D-Lys.

6. The peptide or salt of claim 3, wherein the Arg at position 14 is C-terminally amidated and $Xaa_3$ at position 8 is D-Lys.

7. A pharmaceutical composition comprising:
   (a) the peptide or salt of claim 1; and
   (b) a pharmaceutically acceptable carrier or excipient.

8. A pharmaceutical composition comprising:
   (a) the peptide or salt of claim 2; and
   (b) a pharmaceutically acceptable carrier or excipient.

9. A pharmaceutical composition comprising:
   (a) the peptide or salt of claim 3; and
   (b) a pharmaceutically acceptable carrier or excipient.

10. A pharmaceutical composition comprising:
    (a) the peptide or salt of claim 4; and
    (b) a pharmaceutically acceptable carrier or excipient.

11. A pharmaceutical composition comprising:
    (a) the peptide or salt of claim 5; and
    (b) a pharmaceutically acceptable carrier or excipient.

12. A pharmaceutical composition comprising:
    (a) the peptide or salt of claim 6; and
    (b) a pharmaceutically acceptable carrier or excipient.

13. A method for treating or ameliorating breast cancer, leukemia or chronic rheumatoid arthritis in a subject in need thereof, comprising administering to the subject a pharmaceutical composition comprising as an active ingredient a therapeutically effective amount of the peptide or salt of claim 1.

14. The method according to claim 13 for treating or ameliorating breast cancer.

15. The method of claim 14, wherein the method inhibits breast cancer metastasis.

16. The method according to claim 13, wherein said peptide or salt is a CXCR4 antagonist.

17. The method according to claim 13, wherein the substituted benzoyl group of the peptide or salt is a 4-fluorobenzoyl or a 2-fluorobenzoyl group.

18. The method of claim 14, wherein the substituted benzoyl group of the peptide or salt is a 4-fluorobenzoyl group or a 2-fluorobenzoyl group.

19. The method of claim 17, wherein the substituted benzoyl group of the peptide or salt is a 4-fluorobenzoyl group.

20. The method of claim 13 wherein, in the peptide or salt, the Arg at position 14 is C-terminally amidated and $Xaa_3$ at position 8 is D-Lys.

21. The method of claim 14 wherein, in the peptide or salt, the Arg at position 14 is C-terminally amidated and $Xaa_3$ at position 8 is D-Lys.

22. The method of claim 17 wherein, in the peptide or salt, the Arg at position 14 is C-terminally amidated and $Xaa_3$ at position 8 is D-Lys.

23. The method of claim 19 wherein, in the peptide or salt, the Arg at position 14 is C-terminally amidated and $Xaa_3$ at position 8 is D-Lys.

* * * * *